(12) United States Patent  
Grimes

(10) Patent No.: US 6,740,120 B1  
(45) Date of Patent: May 25, 2004

(54) BONE PROSTHESIS AND METHOD OF ACCESS

(76) Inventor: James B. Grimes, 1921 18th St., Bakersfield, CA (US) 93301

( * ) Notice: Subject to any disclaimer, the term of this patent is extended or adjusted under 35 U.S.C. 154(b) by 0 days.

(21) Appl. No.: 09/913,926

(22) PCT Filed: Feb. 19, 1999

(86) PCT No.: PCT/US99/03709

§ 371 (c)(1),
(2), (4) Date: Aug. 20, 2001

(87) PCT Pub. No.: WO00/48535

PCT Pub. Date: Aug. 24, 2000

(51) Int. Cl.⁷ .................................................. A61F 2/32
(52) U.S. Cl. .................. 623/22.12; 623/908; 623/23.33
(58) Field of Search ........................... 623/22.11, 22.12, 623/22.13, 22.4, 22.42, 22.15, 23.18, 23.21, 23.33, 23.31, 23.44, 908

(56) References Cited

U.S. PATENT DOCUMENTS

| | | |
|---|---|---|
| 2,622,592 A | 12/1952 | Rosenstein |
| 2,650,588 A | 9/1953 | Drew |
| 2,679,245 A | 5/1954 | Timmermans |
| 2,785,673 A | 3/1957 | Anderson |
| 4,795,473 A | 1/1989 | Grimes |
| 5,376,125 A | 12/1994 | Winkler |
| 5,571,195 A | 11/1996 | Johnson |
| 5,725,595 A | 3/1998 | Gustilo |
| 5,960,797 A | * 10/1999 | Kramer et al. ............... 128/898 |

FOREIGN PATENT DOCUMENTS

| | | |
|---|---|---|
| DE | 37 04 089 A1 | 8/1988 |
| EP | 0 434 604 A1 | 11/1990 |
| GB | 764600 | 12/1956 |
| WO | WO 91/11148 | 8/1991 |
| WO | WO 93/11721 | 6/1993 |
| WO | WO 98/06359 | 2/1998 |

OTHER PUBLICATIONS

International Search Report from the European Patent Office date Jul. 24, 2002.

* cited by examiner

*Primary Examiner*—Bruce Snow
*Assistant Examiner*—Brian E. Pellegrino
(74) *Attorney, Agent, or Firm*—Senniger, Powers, Leavitt & Roedel

(57) ABSTRACT

A bone prosthesis for implantation at a joint includes a stem having a tip generally at one end thereof. The stem is sized and shaped for reception in a bone at the joint such that the tip of the stem is exposed to locations outside of the bone. The stem has a passageway extending from a first location on the bone prosthesis to a second location on the bone prosthesis.

17 Claims, 61 Drawing Sheets

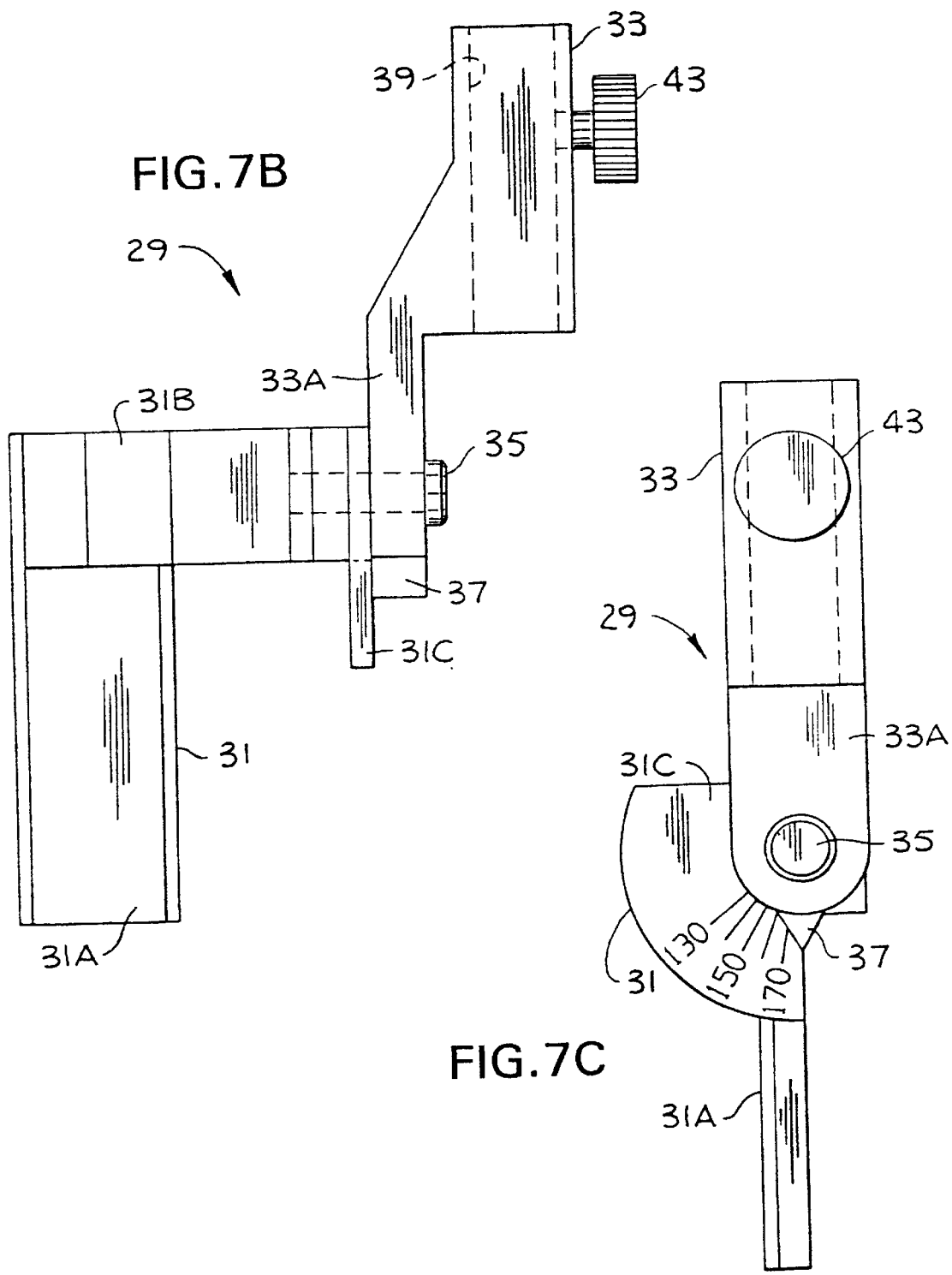

FIG.12A
FIG.12B
FIG.12C
FIG.12D
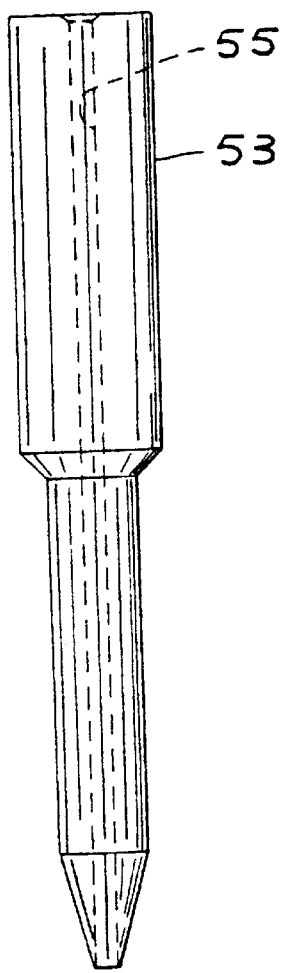
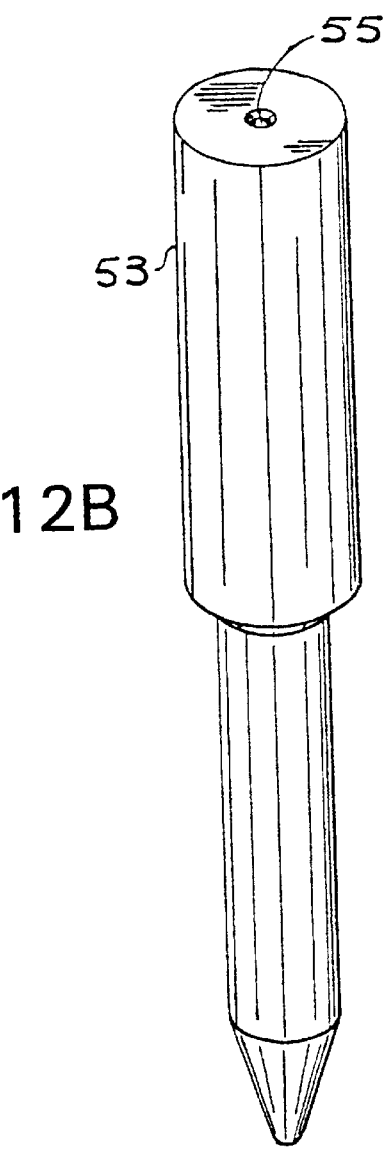
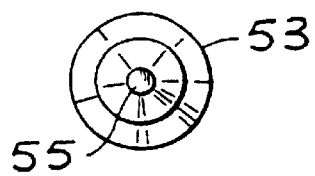
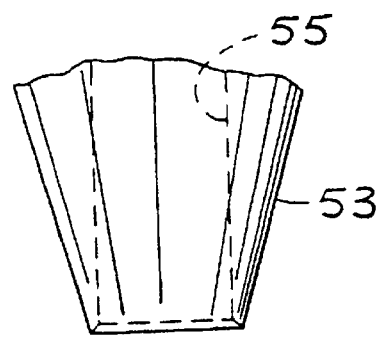

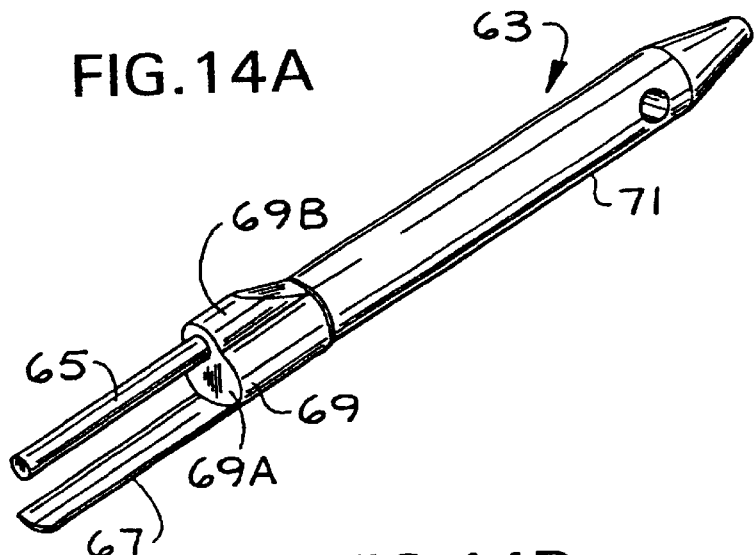
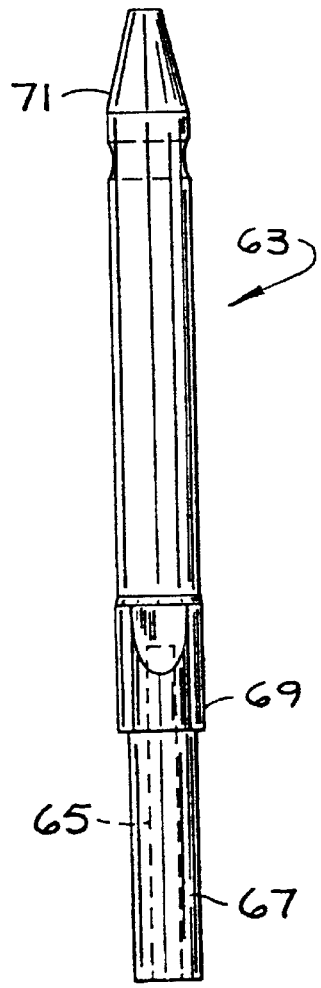
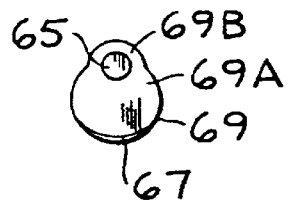
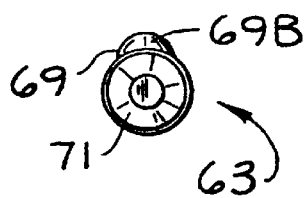
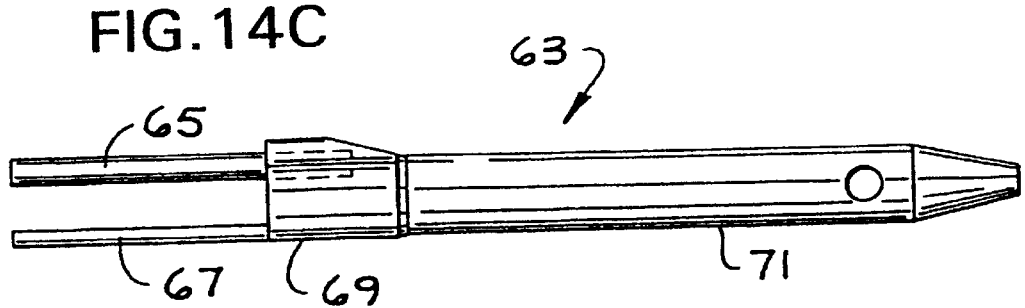

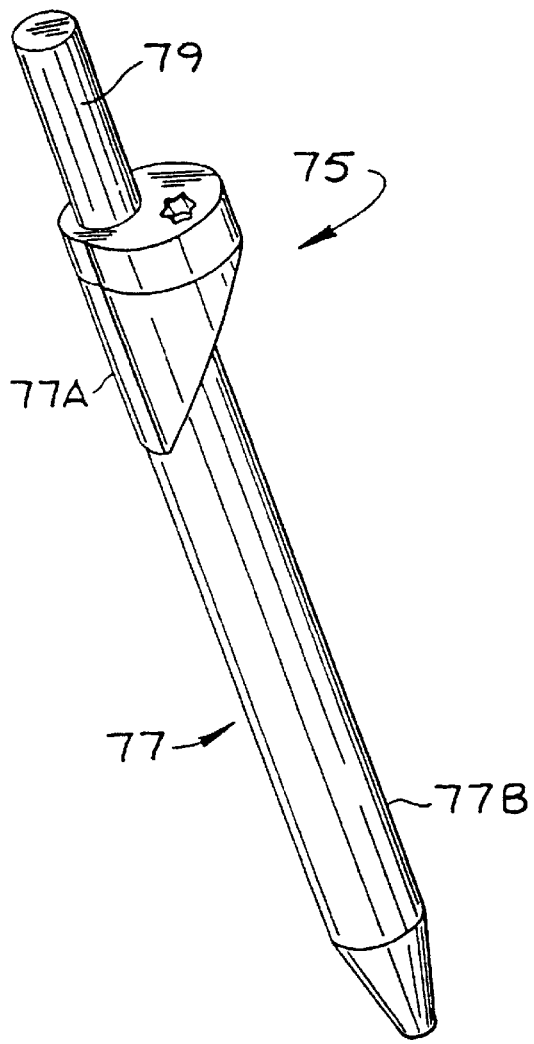
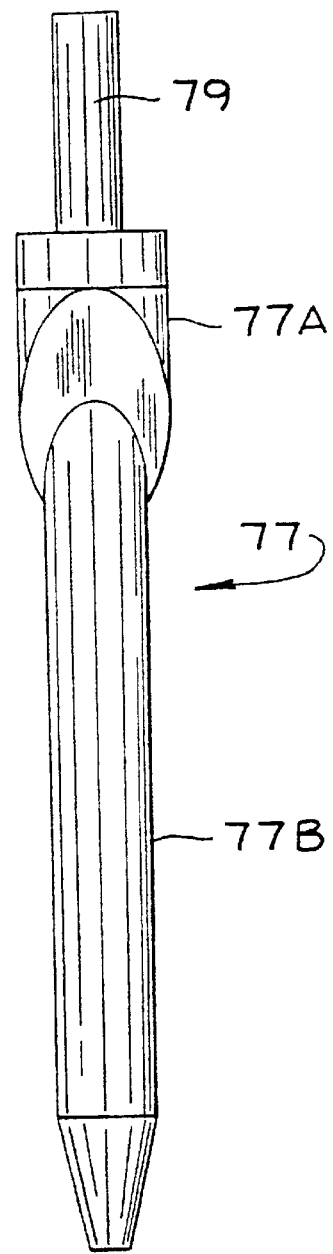
FIG. 16A
FIG. 16B

FIG.17A
FIG.17B
FIG.17C
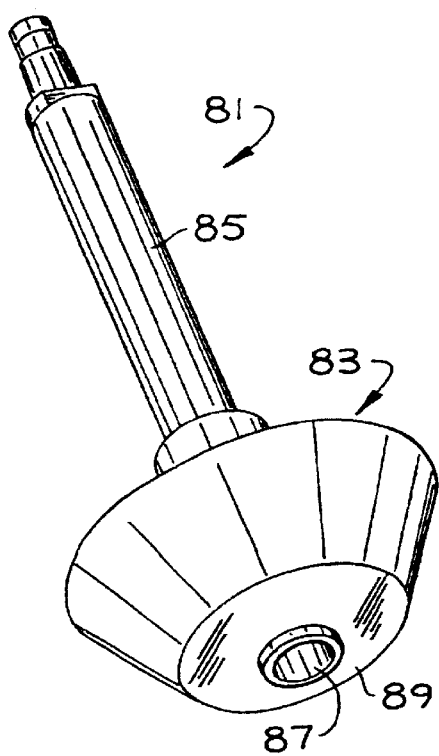
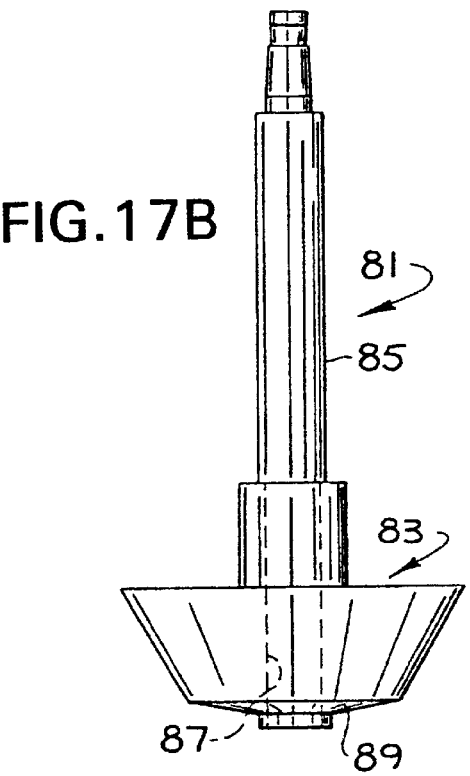
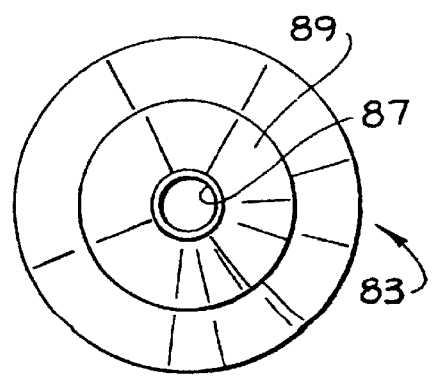

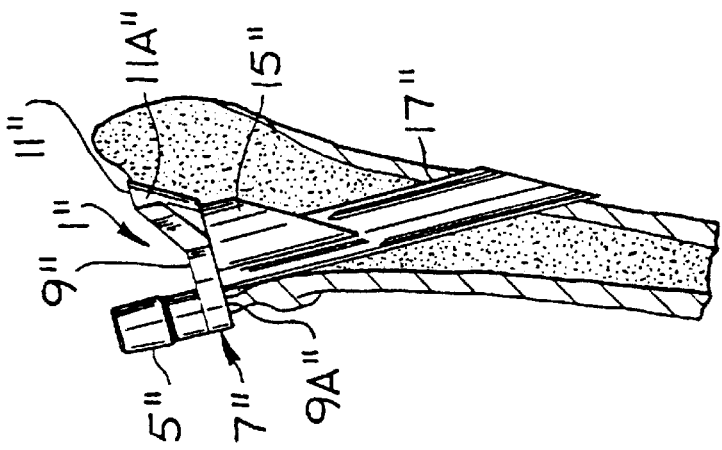
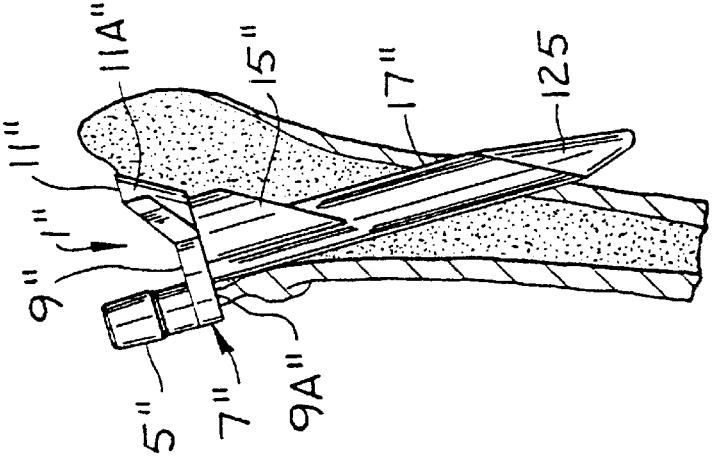
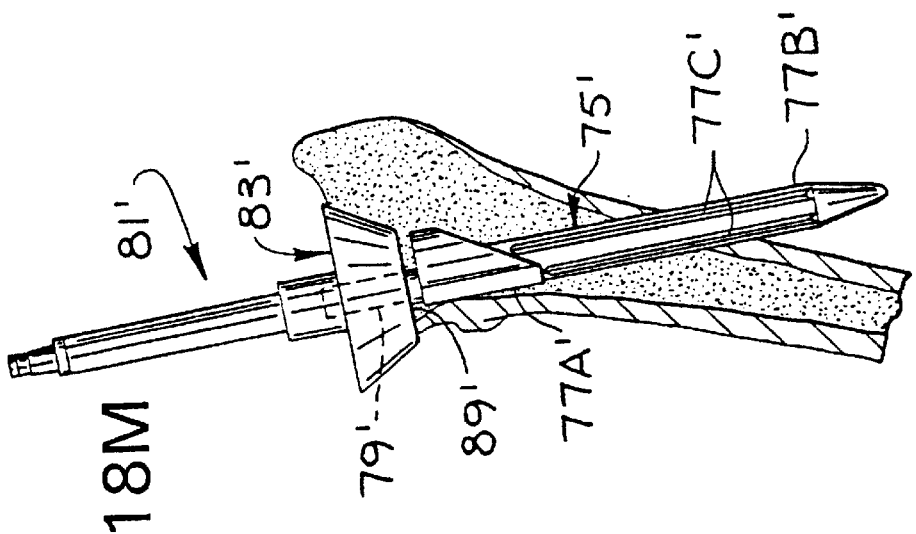

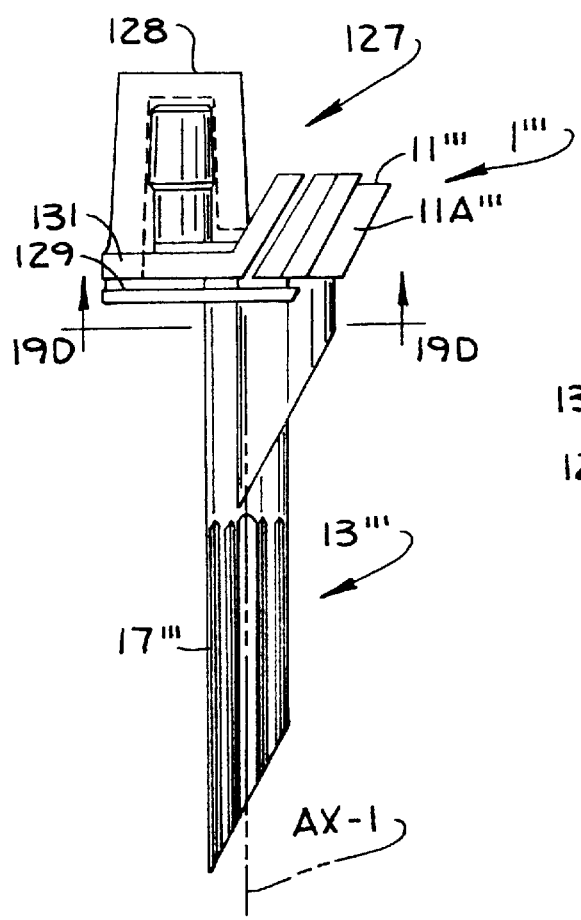
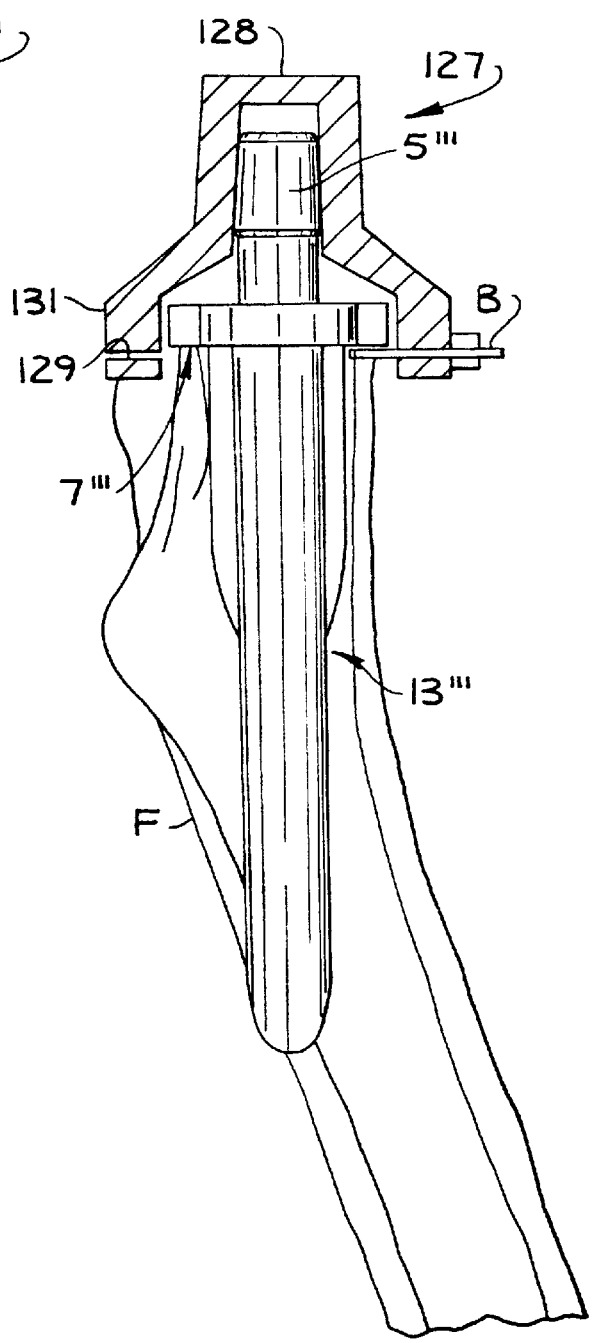

FIG.36A
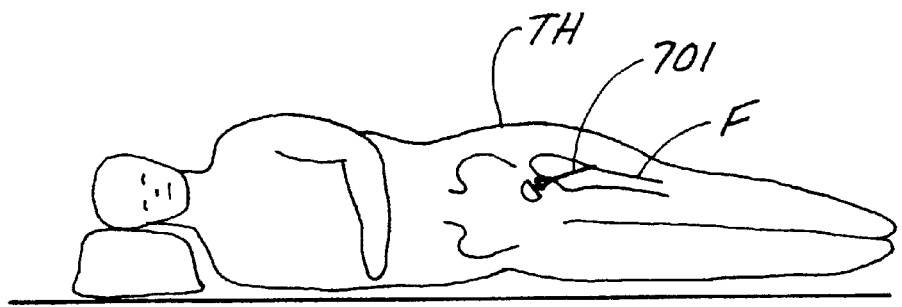
FIG.36B
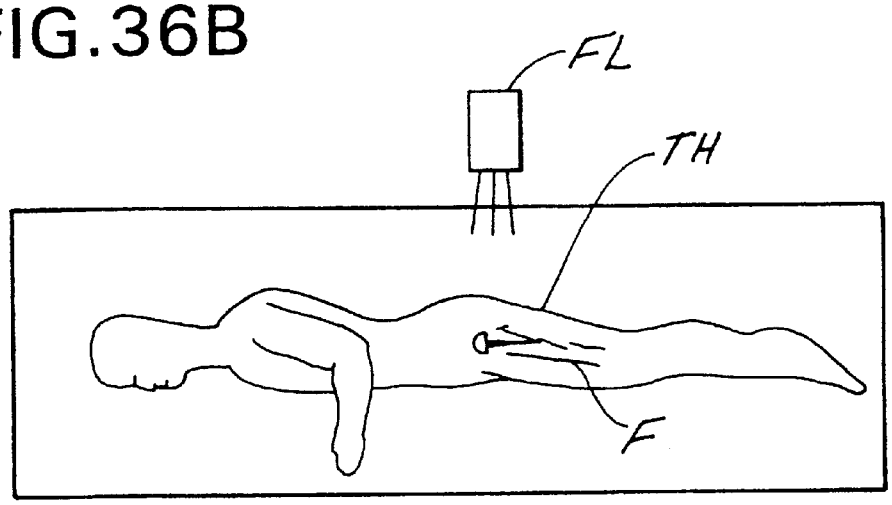
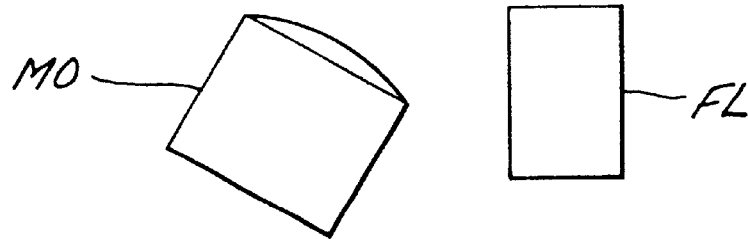

BONE PROSTHESIS AND METHOD OF ACCESS

BACKGROUND OF THE INVENTION

This invention relates generally to femoral prostheses and methods for their implantation.

Total hip replacement became a clinical reality for the first time in November, 1962. The femoral head and neck were removed, the upper marrow canal of the femur was cleaned out (i.e., marrow contents removed), and the metal femoral component was inserted into the femur. Total hip replacement using a femoral component or implant is generally successful for the short term (ten years), however in the long run, deterioration of the bone occurs and the implant may loosen.

Bone deterioration adjacent femoral implants is a multi-factored process which includes at least two elements, strain deprivation and osteolysis. Bone loss due to strain deprivation (or what is commonly but incorrectly referred to as "stress shielding") occurs in association with substantially all conventional intramedullary femoral components and is caused by the implant splinting the upper femur, preventing the upper femur from being subjected to natural bending. My prior application, PCT Application Serial No. US97/14233, includes features directed to alleviating splinting. Osteolysis is a late complication of joint replacement surgery in which the bone adjacent the implant develops lesions, either "scooped out" (focal) or diffuse (linear) areas. Osteolysis is somewhat less common than bone loss due to strain deprivation, and depends on the type of implant used. Several factors are known to contribute to osteolysis, including access of joint wear debris to a joint space JS above the collar of the component and to the area between the implant and the bone (the implant-bone interface IB). Joint wear debris carried by the fluid remains in the joint space JS and becomes concentrated. The synovial lining of the joint has limited ability to absorb and encapsulate the wear debris, resulting in osteolysis of the exposed bone. Another factor is joint fluid pressure in the implant-bone interface IB. The latter factor commonly occurs in prior art implants because fluid is able to enter the implant-bone interface IB. As the person walks, high fluid pressures are generated at the interface and within the bone cells. Recent research suggests that joint fluid pressure is a significant factor in osteolysis.

Although much less common than strain deprivation or osteolysis, the most disastrous cause of bone deterioration adjacent a femoral implant is infection. Infection may occur shortly after the total hip replacement operation (acute infection), or may occur months or years after the operation (late infection). Acute infections may be caused by bacterial contamination of the incision by airborne bacteria or from bacteria from the patient's skin. Late infections usually are caused by bacteria going through the patient's circulatory system and lodging in the bone adjacent the femoral implant.

Infection adjacent a femoral implant is a serious problem because of the pain, fever and disability it causes. The bacteria (or other organisms) cause infection in the bone and soft tissues around the implant and begin to multiply (osteomyelitis). The body's attempt to fight the infection tends to damage the bone as well.

The diagnosis of deep infection of a total joint replacement is often delayed because of the inaccessibility of the hip joint within the body. The diagnosis of infection of a total hip replacement requires aspiration of joint fluid (inserting a needle into the joint space JS (FIG. 34) and drawing infected fluid out of the joint with a syringe) or alternatively, obtaining deep tissue specimens from the joint. Tissue specimens are obtained by open surgery at the joint, or, much less commonly, by arthroscopic surgery (exploration of the joint through small incisions using fiberoptic telescopes).

An infection may be present at the implant-bone interface IB and not manifest itself in the joint fluid (false negative aspiration). It can be technically difficult to obtain fluid from the hip joint because of scarring from the previous surgery. The scar tissue which forms around a femoral implant may also make arthroscopic visualization of the joint difficult. Surgically exposing the hip to obtain tissue samples carries with it the pain and disability of open surgery as well as the risk of introducing bacteria around the implants.

Infrequently, the infection can be treated without removing the implant. The hip joint is surgically exposed and cleaned (debrided) through removal of dead and infected tissue. However, it is not possible to clean everywhere around the implant. Moreover, the interface between the bone and implant is generally inaccessible, which inhibits the introduction of antibiotics into the implant-bone interface IB. As shown in FIG. 34, antibiotics introduced into the joint space JS will generally remain in the joint space and will not flow down into the implant-bone interface IB. Intravenous systemic antibiotics are administered for several weeks or months following surgery. This method of treating an infection adjacent an implant usually is attempted only on early infections (less than three or four weeks) and is not always successful in eradicating the infection.

More commonly, infection adjacent a femoral prostheses requires complete removal of the implant and removal of bone cement (if present). The removal of cemented or non-cemented intramedullary stem femoral implants will destroy some amount of bone. In the case of removal of porous ingrowth (non-cemented) femoral implants, the destruction of bone is extensive. These components frequently require cutting the upper thigh bone (femur) in half longitudinally (extended trochanteric osteotomy), cutting the metal stem in half transversely, and using a hollow coring drill to remove the lower half of the stem (trephining). The extent of bone loss associated with removal of total hip replacement femoral implants is aggravated in cases where pre-existing bone loss from strain deprivation and osteolysis is present. Once the implant is removed, the patient is given systemic (intravenous or oral) antibiotics for two months or more. When there is evidence that the infection has been cleared, a new total hip replacement is installed in a second operation. Fixation of the new implant in the bone is frequently compromised by loss of bone stock.

In some patients, the joint replacement implants are permanently left out (Girdlestone procedure). This option is considered for patients having a weakened immune system, such as those with diabetes, rheumatoid arthritis or who require steroids. A Girdlestone procedure is also considered for patients who are too ill to withstand an additional major operation. With the hip implant absent, the hip joint tissues contract and the leg becomes significantly shorter. With no bony or mechanical connection or support, the hip is unstable and frequently painful. Most patients require the use of crutches, walker or wheelchair after a Girdlestone procedure.

Another problem in the treatment of infection is presented by the systemic administration of antibiotics, taken orally or intraveneously. Systemic antibiotics expose the entire body to the antibiotic. Potential side effects of antibiotics limit the amount that can be given. Side effects of systemic antibiotics include allergic reactions, impairment of kidney function, damage to the nerves which allow hearing and balance, gastrointestinal complications, and other problems. Additionally, bone has a relatively poor blood supply compared with other tissues, e.g., muscles or internal organs, so that achieving high enough concentrations of antibodies in the bone to eradicate the bacterial infection is difficult. The implant, acrylic bone cement (if present), nonviable bone and scar tissue may also harbor deep seated bacteria which may again begin to multiply once antibiotics are discontinued.

An alternative method of delivering antibiotics to an infected hip implant employs an antibiotic cement spacer. The infected hip replacement components are removed and the bone is thoroughly cleaned of infected tissue. A sterilized stem of a femoral implant is covered with a layer of acrylic cement which contains high concentrations of an antibiotic. The stem/antibiotic cement composite structure is placed in the marrow canal of the femur. One advantage of this method is the delivery of high local concentrations of antibiotic directly to the infected tissues. This may decrease the need for systemic antibiotics with their potential side effects. Another advantage is the maintenance of the soft tissue length about the hip which makes the later implantation of a new hip implant technically easier. One disadvantage of the antibiotic cement spacer is a significant decline in the antibiotic levels in the fluid and tissues about the hip after two or three weeks. Also, the antibiotic spacer is usually put in loosely to facilitate later removal. The resulting instability of the implant within the bone may cause pain and prevent full weight bearing. Moreover, if a spacer is left in for a long time it may be difficult to remove, which may result in additional bone loss upon removal.

A second method of delivering antibiotics directly to the infected tissues about an infected hip implant site is the infusion port method. This technique is used after removal of an infected implant to provide a renewable supply of antibiotics directly to the infection site. The port method involves placing an infusion port under the skin away from the infected joint at a location where it is readily accessible from outside the body. The infusion port is anchored with sutures to fascia (connective tissue). A length of tubing from the port is passed under the skin to the site of infection (e.g., hip, knee, shoulder). After surgically cleaning the joint and removal of the infected implants, the end of the tubing is placed in the infected joint. After the operation to insert the infusion port, a needle is passed through the skin overlying the port, through a plastic, self-sealing membrane of the port and into the port. A syringe attached to the needle contains a solution of antibiotics that is infused through the port and tubing directly into the joint. The advantage of this method over an antibiotic spacer technique is that antibiotics can be administered daily, or more often if necessary. This renewable source of antibiotics provides extremely high local concentrations of antibiotics directly to the site of the infection without the side effects associated with systemic antibiotics. These concentrations can be maintained indefinitely by repeatedly infusing antibiotics directly into the joint. A disadvantage of the infusion port method is that it usually is combined with removal of the implant to assure that the antibiotic has access to all of the potentially infected sites at the joint. Referring again to FIG. 34, when conventional intramedullary stem femoral implants are left in place, the antibiotics may not be able to reach the interface between the bone and the implant (or between the cement and the bone).

SUMMARY OF THE INVENTION

Among the several objects and features of the present invention may be noted the provision of a prosthesis and method of implantation which inhibit bone deterioration; the provision of such a prosthesis and method which reduces fluid pressure in the implant-bone interface; the provision of such a prosthesis and method which transports joint wear debris away from the joint space; and the provision of such a prosthesis which has a longer useful life.

Further objects of the invention include the provision of a method and apparatus for diagnosing and treating infections associated with a prosthesis which does not require removal of the prosthesis; the provision of such a method and apparatus which achieves high antibiotic levels at the infection site without affecting the entire system of the patient; and the provision of such a method that maintains soft tissue length adjacent the prosthesis.

Generally, a bone prosthesis for implantation at a joint comprises a stem sized and shaped for implantation in a bone at the joint such that at least a portion of the stem is received in the bone and a portion is exposed to locations outside the bone. The stem has a passageway arranged to vent fluid from a first location which is subject to elevated fluid pressures when the joint is in use after implantation of the prosthesis to a second location for venting fluid pressure from the first location to the second location thereby to inhibit fluid pressure build up between bone located at the joint and the prosthesis.

In another aspect of the invention, a bone prosthesis for implantation at a joint includes a stem having a tip generally at one end thereof. The stem is sized and shaped for reception in a bone at the joint such that the tip of the stem is exposed to locations outside of the bone. The stem has a passageway extending from a first location on the bone prosthesis to a second location on the bone prosthesis.

Another aspect of the present invention is a method for implanting a femoral head-neck prosthesis in a femur without the use of cement. The femur has a shaft and a neck at the upper end of the shaft at the medial side of the femur. The prosthesis has a longitudinal passageway for venting fluid pressure from a first location which is subject to elevated fluid pressures when the joint is in use after implantation of the prosthesis to a second location for venting fluid pressure from the first location to the second location thereby to inhibit fluid pressure build up between bone located at the joint and the prosthesis. The method comprises the steps of cutting the neck of the femur to form a seat on the femur neck, drilling a passage along a line through the shaft of the femur and inserting the stem of the prosthesis in the passage of the femur such that the longitudinal passageway for venting fluid pressure is not occluded.

Yet another aspect of the invention is a method of minimally invasively accessing the femoral head-neck prosthesis which is transosseously implanted in a femur in a thigh of a patient. The prosthesis includes a stem having a passageway extending at least partway through the stem along a longitudinal axis and opening at a tip of the stem. The passageway is in fluid communication with a prosthesis-bone interface. The stem is implanted such that the opening of the passageway in the stem is accessible from a location external to the femur. The method includes examining the prosthesis using an X-ray device while simultaneously rotating the femur until a viewing plane of the X-ray device is generally parallel with the longitudinal axis of the passageway. An intersection point of the longitudinal axis of the stem with skin of the thigh is determined. An incision is made at the intersection point and an instrument is inserted through the skin generally along the longitudinal axis and into the opening of the passageway.

Other objects and features of the present invention will be in part apparent and in part pointed out hereinafter.

BRIEF DESCRIPTION OF THE DRAWINGS

FIG. 4A is a view of the femur showing the axis of the medial trabecular stream;

FIG. 4R is a view showing the calcar planing guide and calcar planer for planing of the femoral neck;

FIG. 7B is a left side elevational view thereof;

FIG. 7C is a front elevational view thereof;

FIG. 12A is an elevational view of a cannulated pin guide;

FIG. 12B is a perspective view of the cannulated pin guide;

FIG. 12C is a bottom end view thereof;

FIG. 12D is a fragmentary, elevational view of the cannulated pin guide showing the bottom end;

FIG. 14A is a front view of the offset reaming guide;

FIG. 14B is a front elevational view thereof;

FIG. 14C is a left side elevational view thereof;

FIG. 14D is a top plan view of the offset reaming guide;

FIG. 14E is a bottom plan view of the offset reaming guide;

FIG. 16A is a perspective view of a calcar planing guide;

FIG. 16B is a left side elevational view thereof;

FIG. 17A is a perspective view thereof;

FIG. 17B is a front elevational view of a calcar planer;

FIG. 17C is a bottom end view thereof;

FIGS. 18A–18Q illustrate a most preferred embodiment of a method for implanting the prosthesis;

FIG. 18A is a view of the femur showing the axis of the medial trabecular stream;

FIG. 18M is a view showing the calcar planing guide and calcar planer for planing of the femoral neck;

FIG. 18N is a view illustrating installation of the prosthesis employing a removable bullet tip;

FIG. 18P is a view illustrating an installed prosthesis;

FIG. 19A is a side elevation of a prosthesis having and a saw template mounted on the prosthesis for use in seating the prosthesis;

FIG. 19B is a fragmentary cross section of an upper portion of the femur and saw template as shown in FIG. 19A, as seen from a position generally medial of the femur;

FIGS. 36A–B illustrate a step in a method for determining the axis of an implanted prosthesis;

FIG. 40A is a perspective view of the infusion assembly and wrench for installing the assembly;

FIG. 40B is a perspective view of the infusion assembly and the threaded passageway of the prosthesis;

FIG. 40C is a schematic, fragmentary cross section similar to FIG. 37 illustrating a syringe attached to the infusion assembly; and FIG. 40D is a fragmentary cross section similar to FIG. 37 illustrating the infusion port assembly and a syringe inserted in the infusion port.

Corresponding reference characters indicate corresponding parts throughout the several views of the drawings.

Figure 1:
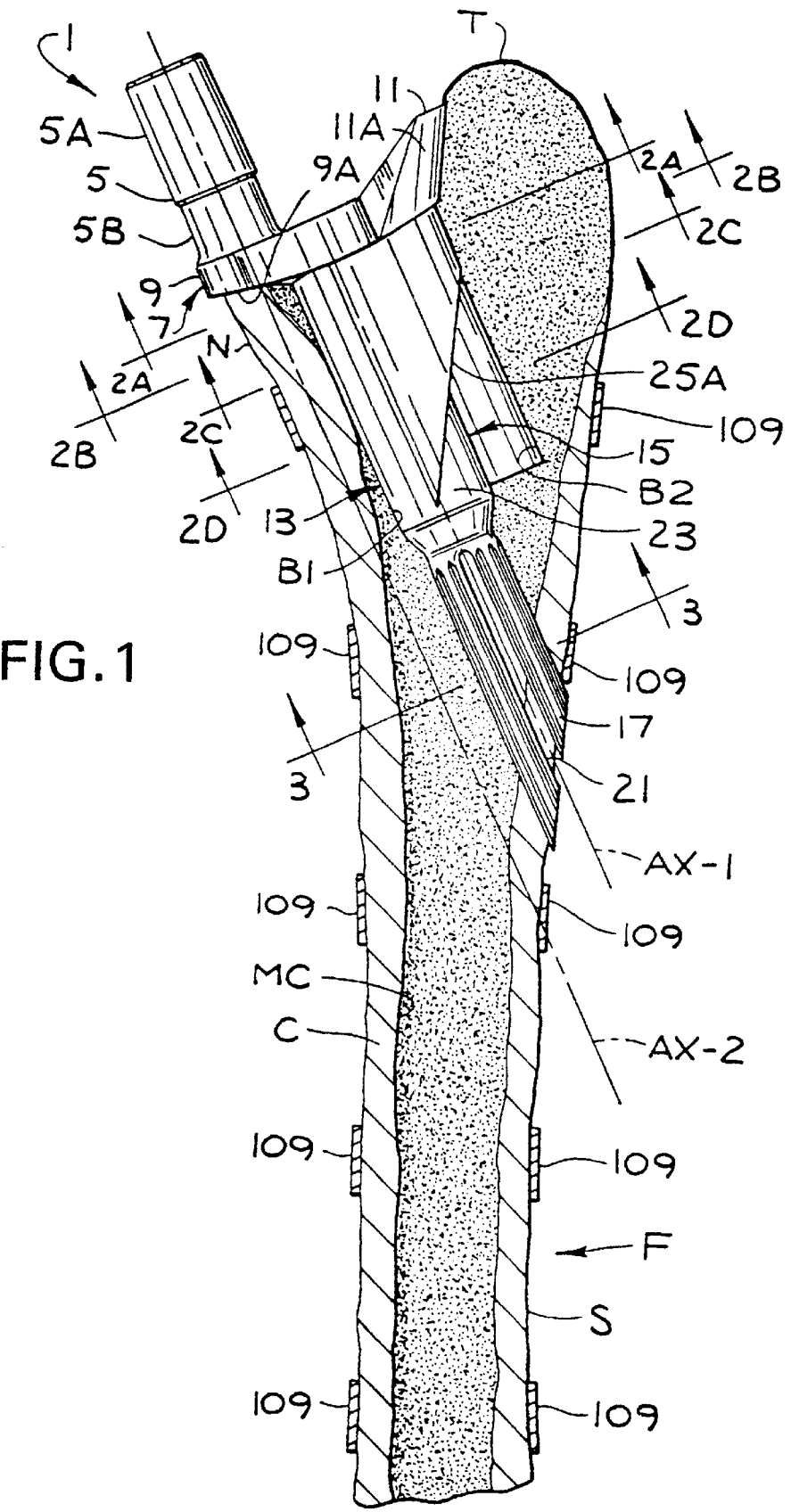
FIG. 1 is a fragmentary cross section of an upper femur showing a femoral head-neck prosthesis of the present invention implanted in the femur (the prosthesis being shown in full lines)
Figure 1A:
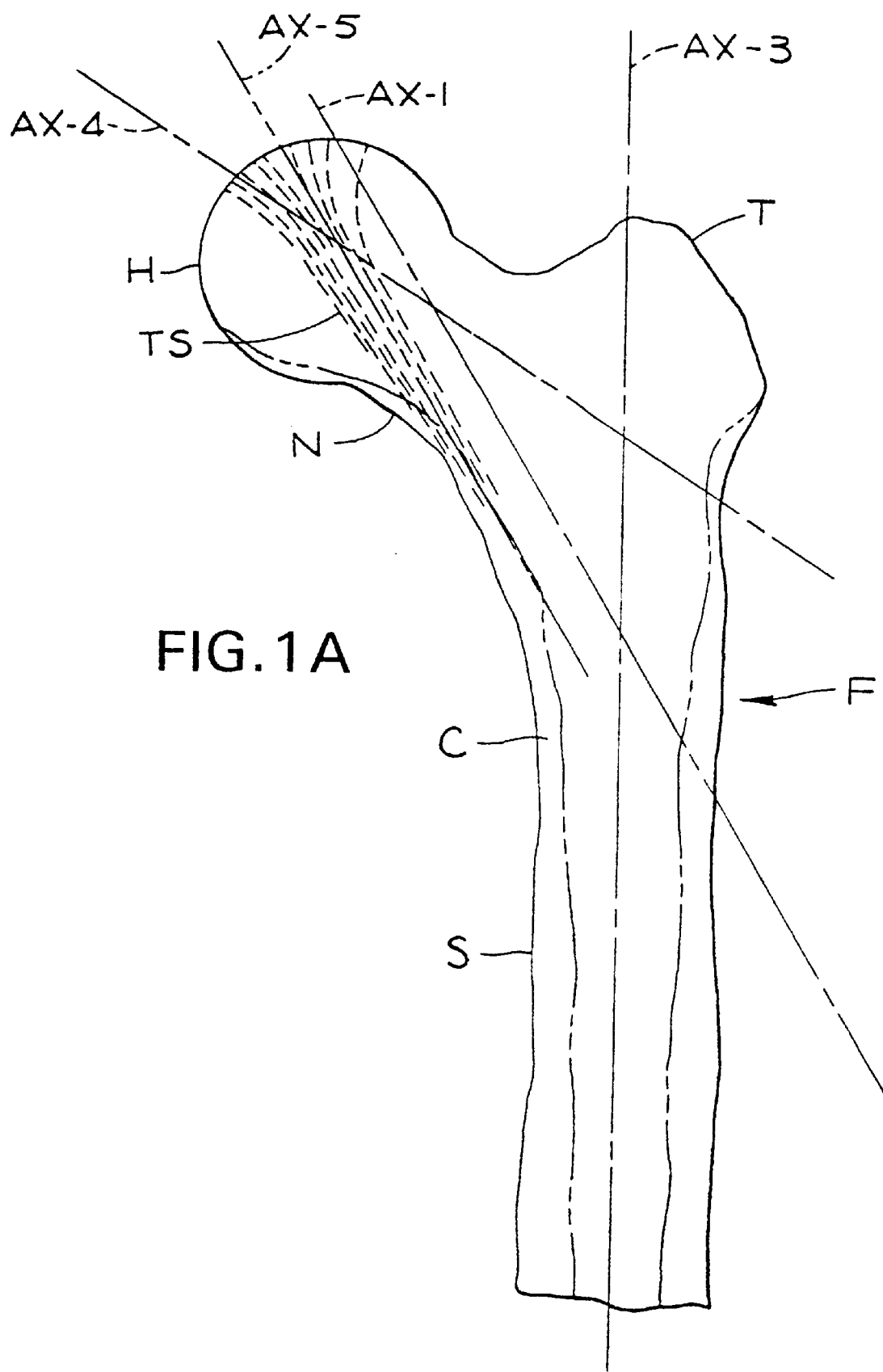
FIG. 1A is a view of an intact femur showing the medial trabecular stream of the femur and axes of the femur and prosthesis.
Figure 1B:
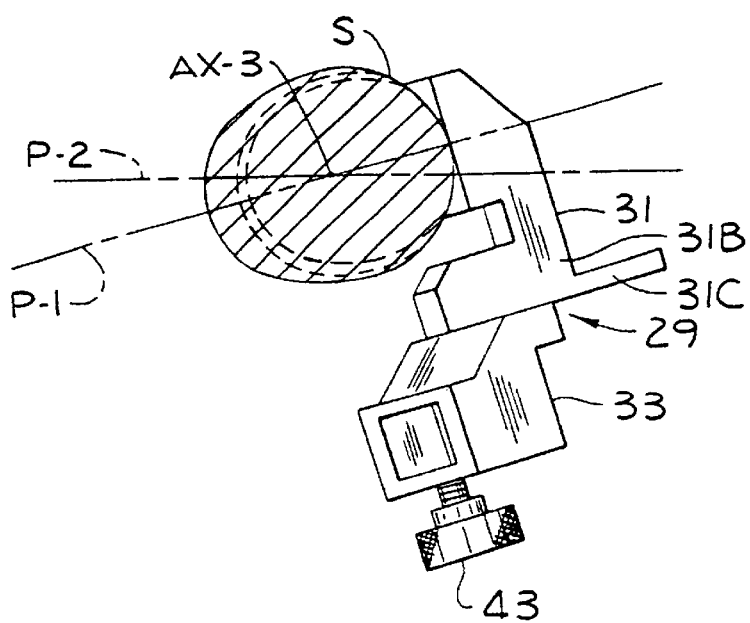
FIG. 1B is a cross-sectional view through the femoral neck illustrating the planes of the femur.

DETAILED DESCRIPTION OF THE PREFERRED EMBODIMENTS (a) The Femoral Head-Neck Prosthesis Referring now to the drawings, and in particular to FIGS. 1, 1A and 1B, a transosseous, non-cemented femoral head-neck prosthesis of the present invention (indicated generally at 1) is shown as implanted in a femur F. The femur includes a femoral shaft S, a femoral head H, neck N and a greater trochanter T at the upper end of the shaft at the lateral side of the femur. The femur F has a hard layer of cortical bone C adjacent the surface of the bone, relatively soft cancellous bone and endosteum (not shown) inside the femur. The prosthesis 1 is made of cobalt-chrome alloy, titanium or other suitable material, and has a longitudinal axis generally indicated at AX-1. As implanted, the prosthesis 1 extends generally from the resected femoral neck N diagonally across the medullary canal MC and out (posterolaterally) an opposite side of the femur. The prosthesis 1 is of the type which is not cemented into the femur F, but is secured by mechanical interconnection of the prosthesis with the bone, as described more fully hereinafter. The prosthesis 1 is constructed so that it is securely held in the bone from rotation (about its longitudinal axis AX-1) and toggling (anterior-posterior and medial-lateral) motion, while permitting axial micromotion to achieve natural bone loading condition thereby to preserve the bone.

The prosthesis 1 has a generally spherical ball 3 which is received in a cup (not shown) implanted in the hip socket (not shown) to permit movement at the hip joint. Referring now additionally to FIGS. 5A–5H, the ball 3 is fixedly attached to an upper portion 5A of a neck 5 of the prosthesis which is received in a hole (not shown) in the underside of the ball. The neck 5 is generally cylindrical in shape and includes a lower portion 5B below the upper portion 5A which is of a smaller diameter than the upper portion. The lower portion 5B of the neck is mounted on a collar (generally indicated at 7) of the prosthesis 1 which rests against the femoral neck N, as shown in FIG. 1, and transmits loads to the upper femur. As shown, the continuous, circumferential collar 7 is sized and shaped to extend outward laterally, anteriorly, medially and posteriorly to cap the medullary canal MC.

The collar 7 includes a neck platform 9 on which the neck 5 is mounted, and a curved flange 11 which engages the greater trochanter T of the femur. The underside of the neck platform 9A has a slight frustoconical shape and the underside of the flange 11A has the shape of a section of cone. In the preferred embodiment, the underside 9A of the platform makes an angle of about 10° with a plane perpendicular to the longitudinal axis AX-1 of the prosthesis. The shape of the underside 9A and its close correspondence to the shape of the seat formed on the resected neck N allow the collar 7 to cap the medullary canal MC and inhibit migration of debris and fluid into the medullary canal after implantation of the prosthesis 1. By inhibiting migration of fluid into the medullary canal, the prosthesis reduces the fluid pressure at the implant-bone interface and thereby inhibits bone deterioration. The curved underside 11A of the flange makes an angle of about 60° with the same plane. Thus, the underside (9A, 11A) of the collar 7 defines a compound angle. The flatter neck platform 9 lies on the partially resected femoral neck N, and the flange 11 rests against the greater trochanter T of the femur. The greater trochanter is the primary sight of muscle attachment to the femur F at the hip. The upstanding flange 11 permits the collar 7 to solidly support the prosthesis 1 on cortical bone C on the upper femur while allowing most of the greater trochanter T to be preserved. Use of a substantially flat collar (not shown) would require resection of a substantial portion of the trochanter T to provide room for the collar. The underside (9A, 11A) of the collar 7 of the present invention engages and is supported by the hard cortical bone C of the femur.

In the preferred embodiment, the underside 9A of the neck platform 9 and underside 11A of the flange 11 are coated with a porous material (not shown) to facilitate bone growth into the collar 7 where it rests on the upper end of the femur F. However, the remaining portions of the collar 7 and all other parts the prosthesis 1 preferably remain free of porous coating, roughening or other construction which would encourage bone growth into the prosthesis. It is to be understood that the use of porous coating or other structure to facilitate bone ingrowth into the prosthesis 1 may be other than described and still fall within the scope of the present invention.

A stem, generally indicated at 13, mounted on the underside of the collar 7 extends generally downwardly through the femur F. In the preferred embodiment, the neck 5, collar 7 and stem 13 are formed as one piece. The longitudinal axis AX-2 of the neck 5 is parallel to the longitudinal axis of the stem, which is coincident with the longitudinal axis AX-1 of the prosthesis 1. As installed, the prosthesis 1 is substantially parallel to an axis AX-5 (FIG. 1A) corresponding to the direction of the normal loading vector of the hip so that forces from the hip are applied compressively to the neck 5 which transmits those forces (via the collar 7) compressively to the femoral neck N. Axial fixation of the prosthesis 1 in the bone is achieved by bone ingrowth of the upper femur F into the collar 7. As described more fully hereinafter, axial fixation of the stem 13, caused by bone ingrowth into the stem and/or strain hardening of bone engaging the stem, is prevented by construction of the stem.

Figure 3:
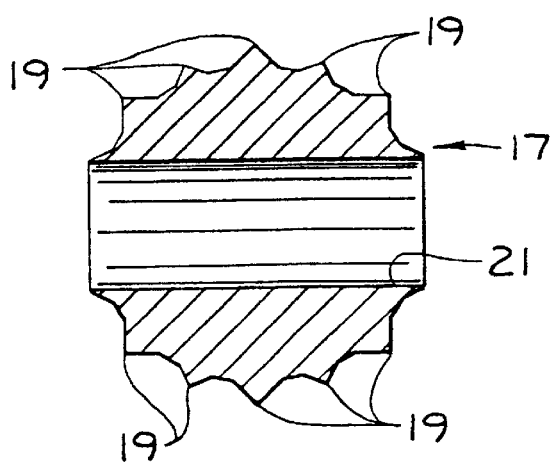
FIG. 3 is a cross-section through the splined portion of the lower stem taken in the plane of line 3—3 of FIG. 1.
Figure 2A:
FIGS. 2A–2D illustrate areas of contact between the upper prosthesis and bone at locations indicated by lines 2A—2A through 2D—2D, respectively.
Figure 2B:
Figure 2C:
Figure 2D:
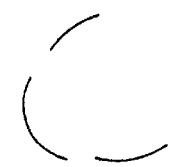

The stem 13 includes an upper portion and a lower portion (designated generally by reference numerals 15 and 17, respectively). The radially outwardly facing surfaces of the stem 13 disposed for engaging the interior of the femur F are, broadly, "fixation surfaces." The lower portion 17 is sized for a close fit within the femur F, and has longitudinally extending splines 19 (see FIGS. 3 and 5H) which penetrate the bone inside the femur to secure the prosthesis 1 in the femur. The lower portion 17 has a longitudinal split 21 to accommodate normal load deflection of the proximal femur. The splines 19 hold the prosthesis 1 securely against rotational movement about the longitudinal axis AX-1 of the prosthesis after implantation, and encourage bone growth between the splines. However, although the splines 19 resist axial displacement of the prosthesis 1 relative to the femur F, the splines do not rigidly fix the prosthesis against axial micromotion. To provide additional fixation of the prosthesis 1, splines (not shown) may also be formed on the upper portion 15 of the stem.

Figure 6:
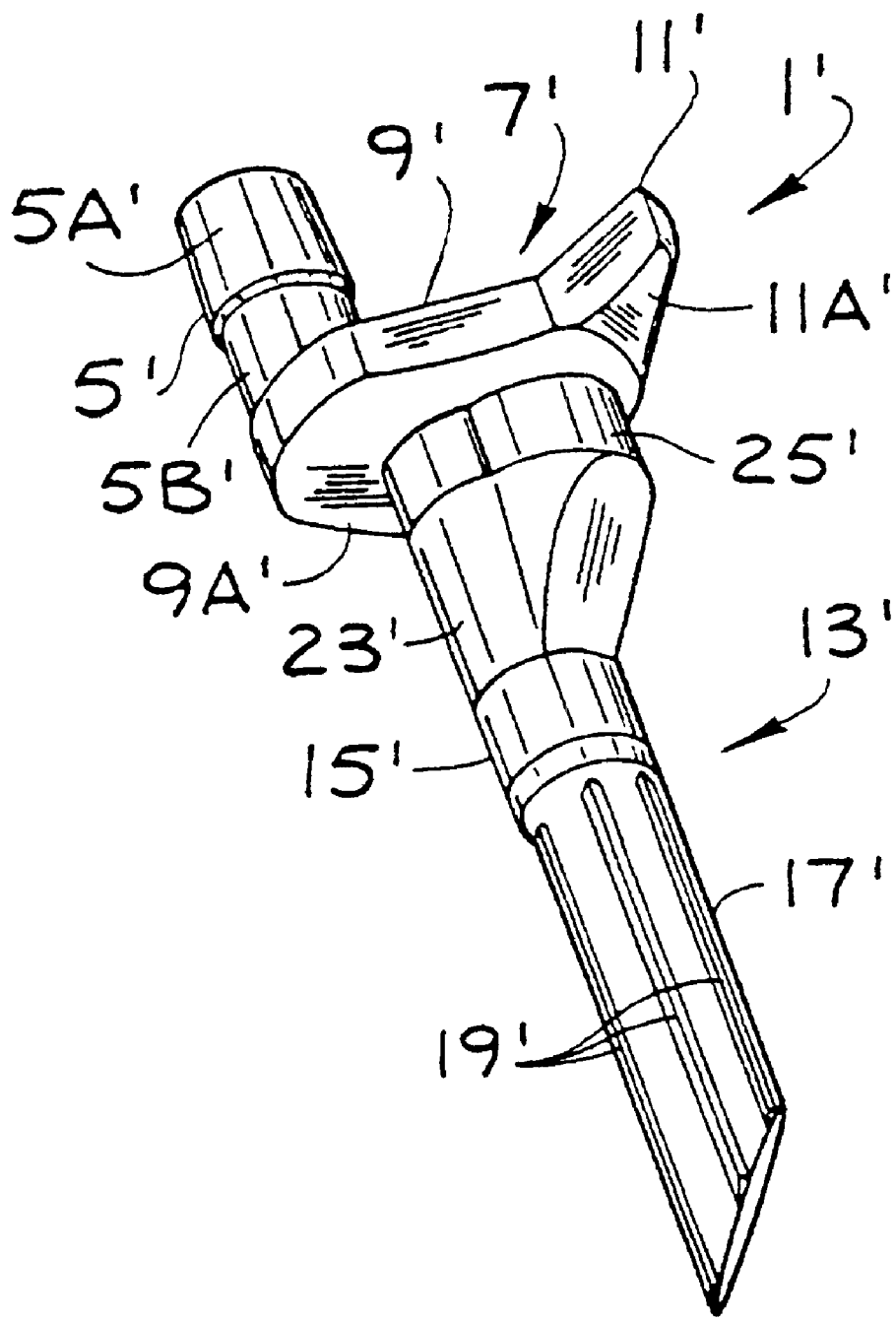
FIG. 6 is a perspective view of a solid stem prosthesis.
Figure 18B:
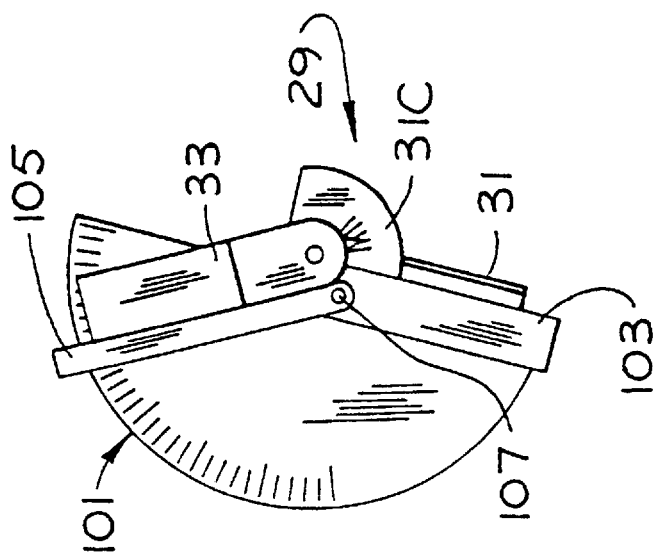
FIG. 18B is a view showing setting of the angle guide prior to mounting on the femur.

A more preferred embodiment of a prosthesis 1' is shown in FIG. 6 has a solid lower stem portion 17'. It is believed that the solid stem provides for greater accuracy in installation and prevents axial fixation which potentially might occur through ingrowth of bone into the slot 21 of the prosthesis 1. A still more preferred embodiment of a prosthesis 1" is shown in FIGS. 18P and 19 to have a flat underside 9A" of the collar 7".

The distal end of the lower portion 17 of the stem 13 is cut on an angle to the longitudinal axis, so that the distal end of the lower portion is somewhat pointed. Moreover, the distal end of the lower portion 17 is generally aligned with or parallel to the outer surface of the femur F on the posterolateral side. The lower portion 17 preferably extends outwardly from the posterolateral side of the femur F to inhibit bone growth over the distal end of the lower portion which would fix the prosthesis 1 in an axial direction and prevent the natural loading at the upper end of the femur by the collar 7. The upper portion 15 of the stem 13 generally has the shape of overlapping cylinders near the collar 7 (see FIG. 5G). A first overlapping cylindrical element of the upper portion is designated 23, and a second overlapping cylindrical element of the upper portion is designated 25. The first (smaller) cylindrical element 23 is co-axial with the longitudinal axis AX-1 of the prosthesis 1, while the second (larger) cylindrical element 25 has an axis which is parallel to the first cylindrical element and radially offset a distance from the axis AX-1 less than the sum of the radii of the first and second cylindrical elements. The first cylindrical element 23 has a diameter greater than the coaxial stem lower portion 17 of the stem. The diameter of the lower portion 17 is kept small to minimize the size of the opening formed in the posterolateral femoral cortex. As an example, if the diameter of the first element 23 were 15 mm, the diameter of the lower portion 17 would be about 12 mm. The shape of the upper portion 15 is defined by the portions of the first and second cylindrical elements 23, 25 which are not overlapping. The offset, eccentric location of the second element 25 causes the upper portion 15, as received in the bores B1, B2 to hold the prosthesis against rotation about axis AX-1. A lower end surface 25A of the second cylindrical element is cut in a plane which makes an angle of approximately 30° with respect to the longitudinal axis AX-1.

As illustrated by FIGS. 2A–D, the upper portion 15 of the stem 13 contacts the endosteal neck cortex of the femur F only in discrete areas around the circumference of the upper portion. The cross sectional views of the drawings (taken as indicated in FIG. 1) schematically illustrate the regions of engagement of the cortex and the upper portion 15 of the stem at four distinct locations along the length of the upper portion. It will be noted that engagement does occur at three spaced apart locations around the upper portion 15 so that the upper portion is able to provide good fixation against both rotation motion of the prosthesis 1 about its longitudinal axis AX-1 and toggling motion of the prosthesis about axes perpendicular to the longitudinal axis.

However, the discrete areas of contact do not rigidly fix the upper portion 15 of the stem 13 against axial movement relative to the femur F. The limited area to of contact reduces the frictional interaction of the prosthesis 1 and bone in the endosteal neck cortex. Moreover, the upper stem portion 15 has smooth exterior walls which substantially prevent bone from growing into the upper stem portion thereby to prevent axial fixation of the prosthesis by bone ingrowth. Thus, the upper stem portion 15 will not prevent loads from the hip from being applied compressively to the upper end of the femur F. This more natural loading of the femur induces more natural straining of the upper femur and prevents deterioration of the upper femur, which is important to maximizing the useful life of the implanted prosthesis 1.

(b) Instruments Used To Implant The Prosthesis

Figure 7A:
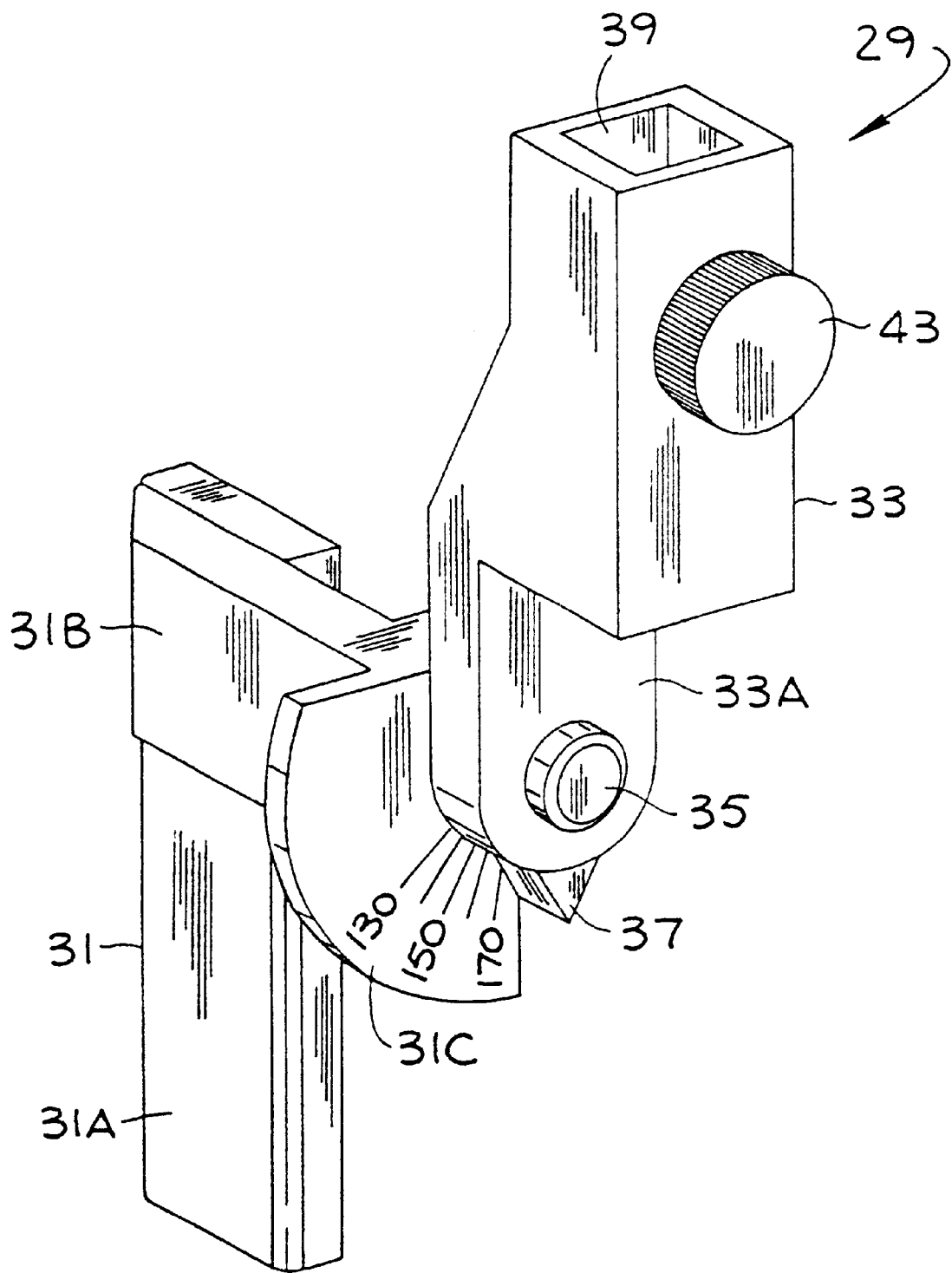
FIG. 7A is a perspective view of an angle guide.
Figure 8A:
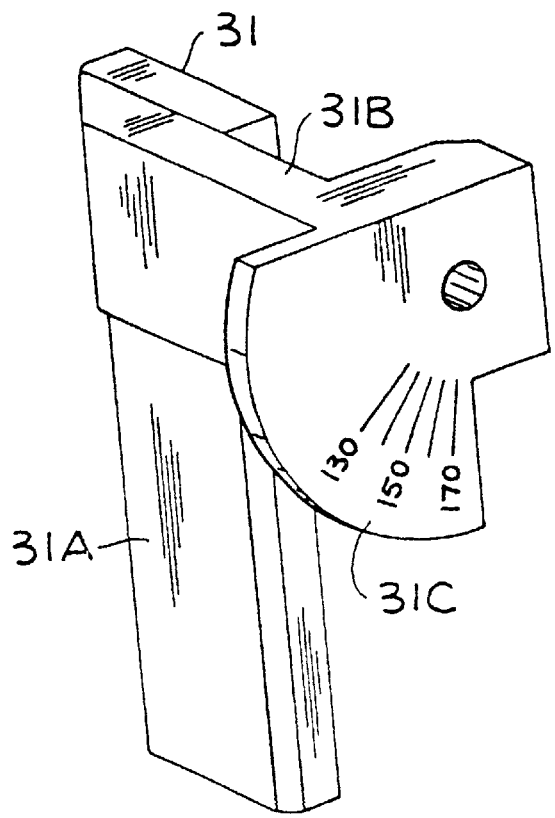
FIG. 8A is a perspective view of a bracket of an angle guide.
Figure 8B:
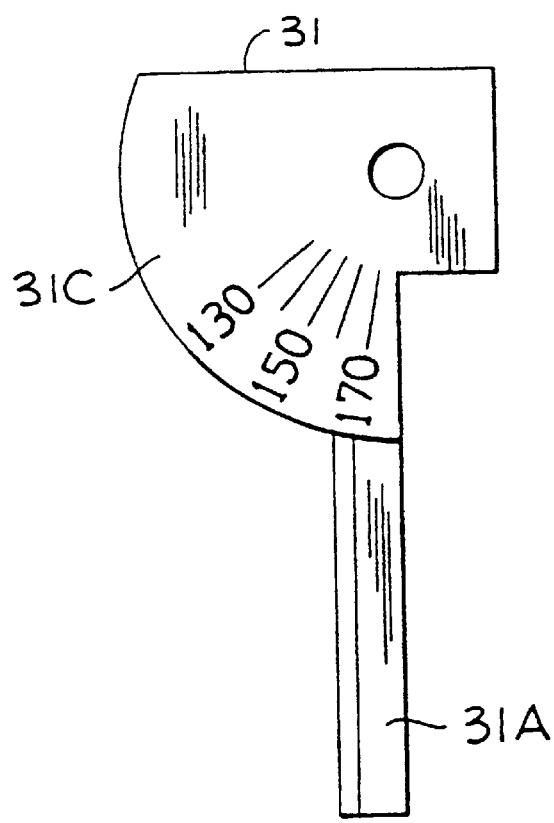
FIG. 8B is a front elevational view thereof.
Figure 8C:
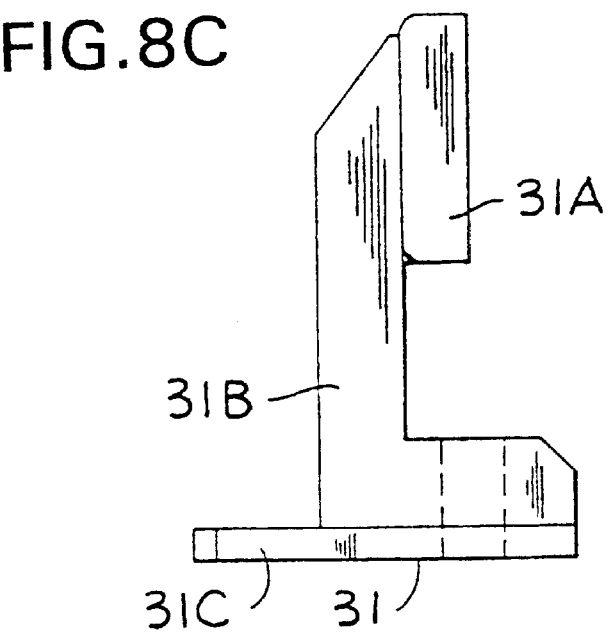
FIG. 8C is a top plan view of a bracket thereof.
Figure 8D:
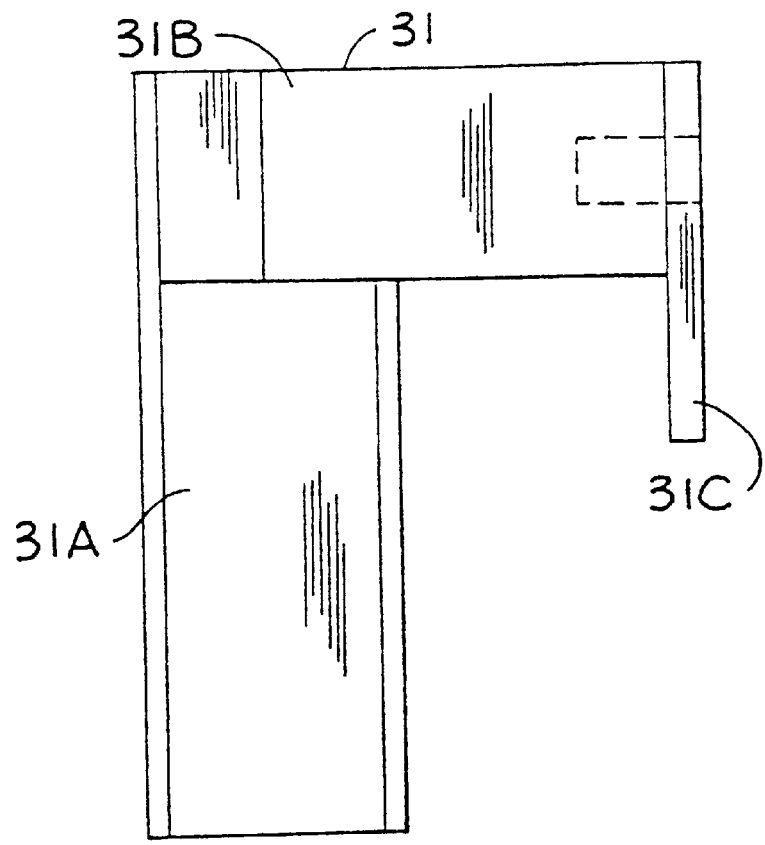
FIG. 8D is a left side elevational view thereof.
Figure 9A:
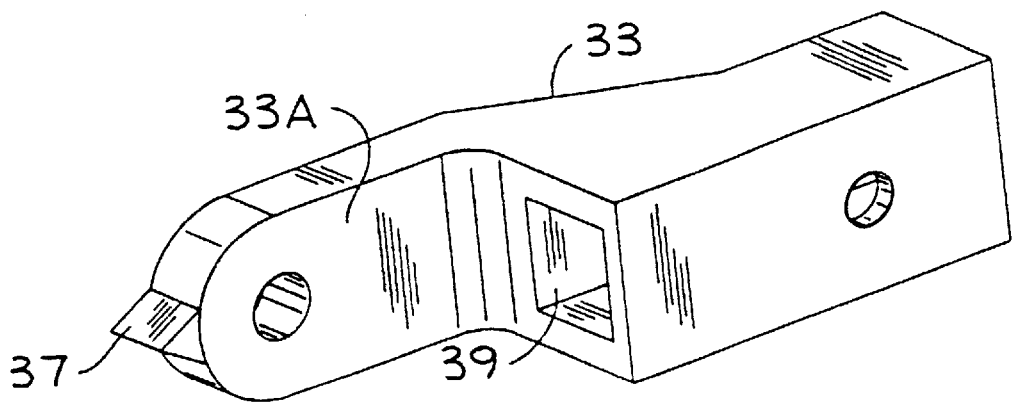
FIG. 9A is a perspective view of an arm of the angle guide.
Figure 9B:
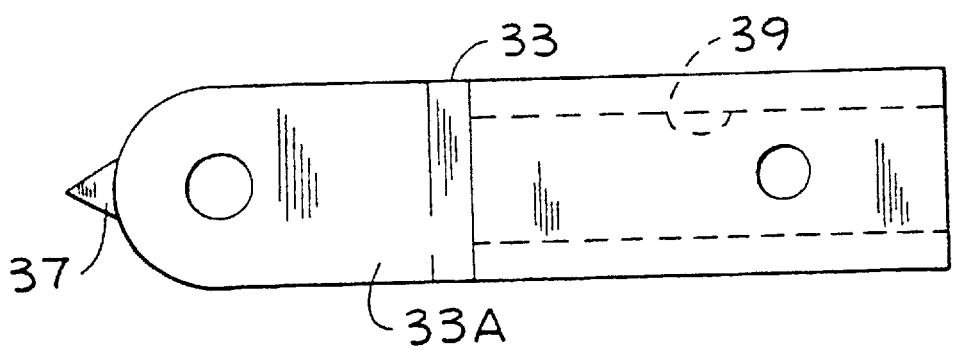
FIG. 9B is a front elevational view thereof.
Figure 9C:
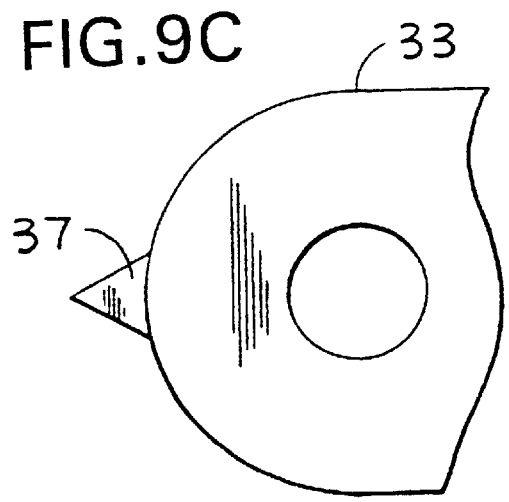
FIG. 9C is an enlarged, fragmentary front elevational view of the left end of the arm.
Figure 9D:
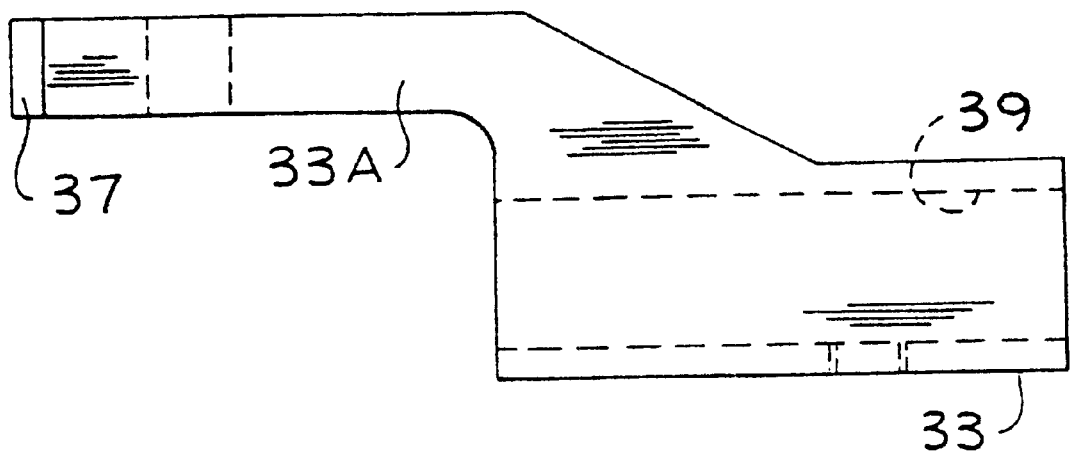
FIG. 9D is a top plan view of the arm of the angle guide.
Figure 9E:
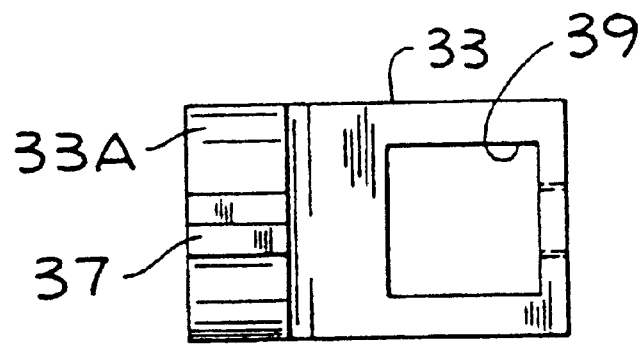
FIG. 9E is a left side elevational view thereof.
Figure 10A:
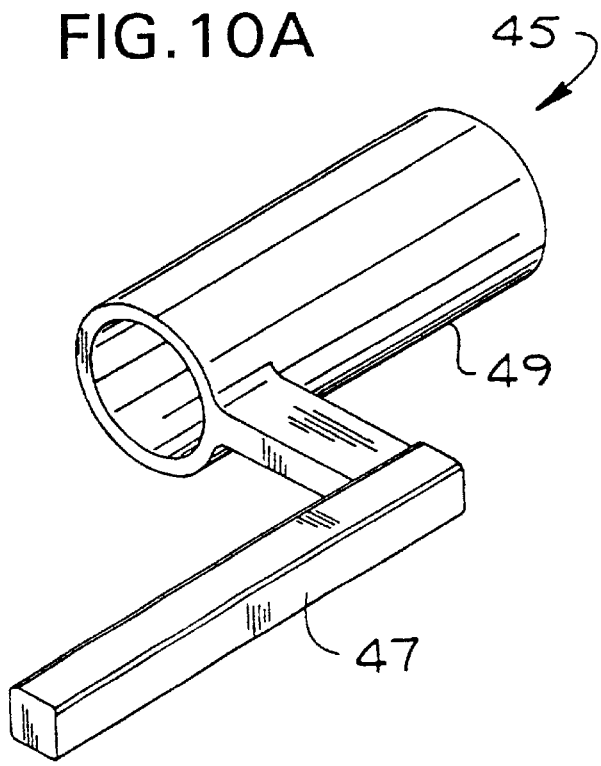
FIG. 10A is perspective view of a calcar miller guide.
Figure 10B:
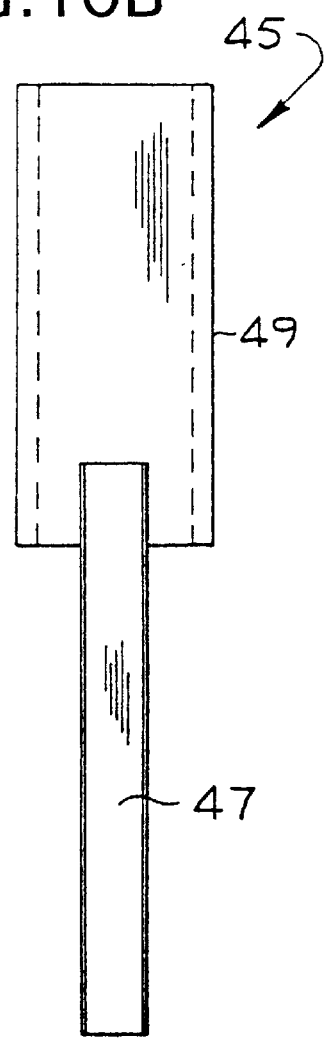
FIG. 10B is a front elevational view thereof.
Figure 10C:
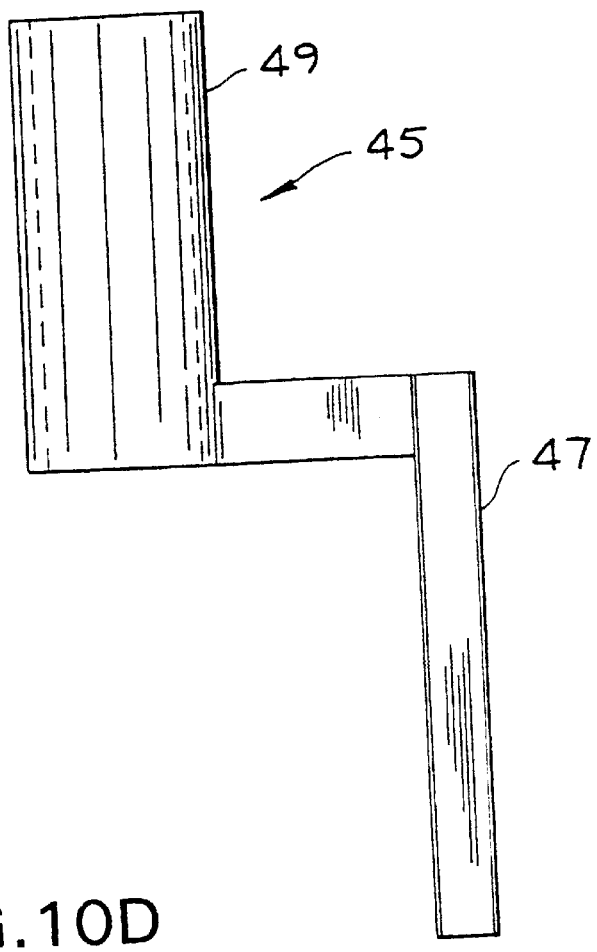
FIG. 10C is a front elevational view thereof.
Figure 10D:
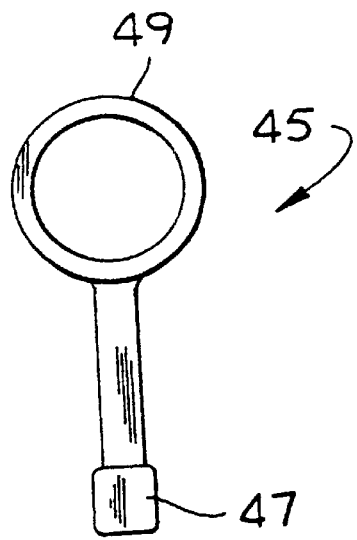
FIG. 10D is a bottom plan view thereof.

While a number of different instruments may be helpful for implanting the femoral head-neck prosthesis 1, an angle guide generally designated at 29 and shown in FIGS. 7A–7C is particularly adapted to be removably secured to the femoral shaft S for holding a plurality of cutting, drilling and reaming accessories in position with respect to the femur F. The angle guide 29 comprises a bracket 31 (see FIGS. 8A–8D) having a first member 31A adapted to be removably secured by a suitable clamp (not shown) in face-to-face engagement with the femoral shaft S. A second member 31B extends outwardly from the first member 31A and includes an arcuate faceplate 31C. A guide sleeve 33 or outrigger portion (see FIGS. 9A–9E) is capable of extending at a selected angle upwardly and outwardly from the bracket 31 at one side of the femoral shaft. The guide sleeve 33 includes a mounting member 33A attached to the bracket 31 by a screw 35. The guide sleeve 33 may be angularly adjusted relative to the bracket 31 by loosening the screw 35 and turning the guide sleeve on the screw to a selected angular position. The faceplate 31C carries indicia which are pointed to by a pointer 37 associated with the mounting member 33A to show the angle of the guide sleeve. The angle is selected so that the guide sleeve 33 extends from the bracket 31 along a line substantially parallel to the previously determined average compression loading vector (the "normal" direction in which the femur F is loaded, AX-5) for the femur of the specific patient when the bracket is attached to the femur. The guide sleeve 33 has a through hole 39 for receiving and holding other instruments in the same angular position as the guide sleeve.

As noted above, angle guide 29 is adapted for holding a variety of different instruments used in implanting the prosthesis 1 of the present invention. One such instrument is a saw guide 41 (see FIG. 4B) which can be detachably mounted in the through hole 39 of the guide sleeve 33 for guiding a saw blade (not shown) to cut the femoral neck N. The saw guide 41 has a sawcut slot 41A generally perpendicular to the central longitudinal axis of guide sleeve 33. The saw guide 41 is slidably adjustable in the through hole 39 to properly position it with respect to the femoral neck N. A set screw 43 of the angle guide 29 is provided for securing the saw guide 41 in adjusted position.

Referring now to FIGS. 10A–10D a calcar miller guide, generally indicated at 45, has an outrigger portion 47 receivable in the through hole 39 of the angle guide 29 for mounting on the angle guide in the same manner as the saw guide 41. The calcar miller guide has a guide tube 49 attached to the outrigger portion 47. Calcar miller guide 45 is slidably adjustable along guide sleeve 33 in the through hole 39 to properly position it with respect to the femoral neck seat of the femoral neck N. The calcar miller guide 45 is fixedly held from rotation with respect to the guide sleeve 33. The position of the calcar miller guide tube 49 over the femoral neck N defines the axis AX-1.

Figure 11A:
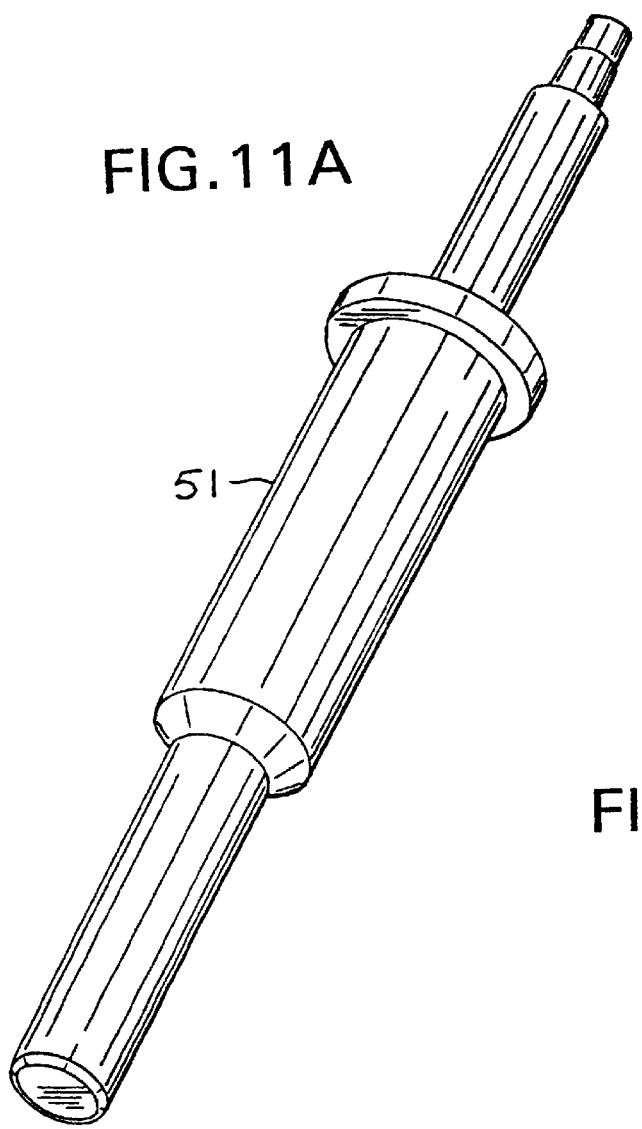
FIG. 11A is a perspective view of a calcar miller.
Figure 11B:
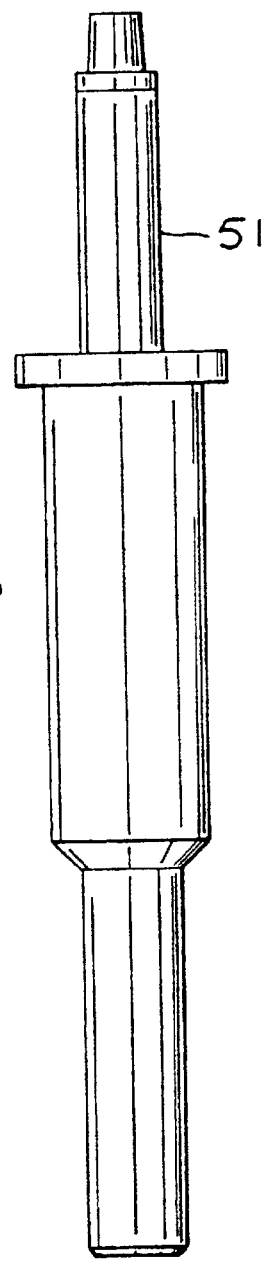
FIG. 11B is an elevational view of the calcar miller.
Figure 11C:
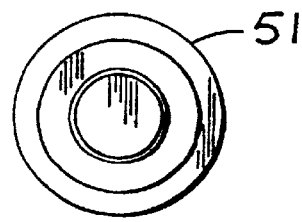
FIG. 11C is a bottom end view of the calcar miller.
Figure 13A:
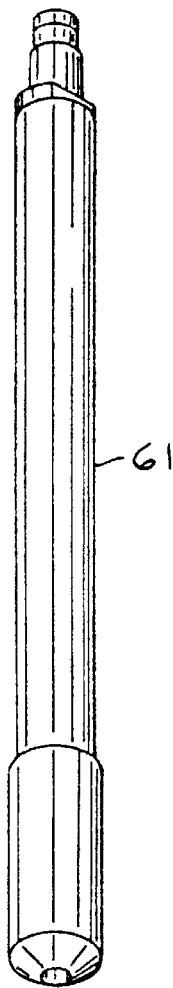
FIG. 13A is a perspective view of the cannulated cortex drill.
Figure 13B:
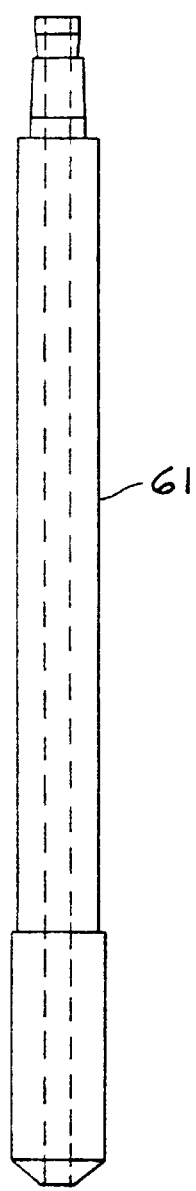
FIG. 13B is a front elevational view of a cannulated cortex drill.
Figure 13C:
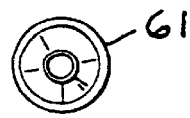
FIG. 13C is a bottom end view thereof.
Figure 13D:
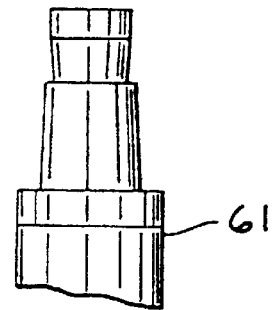
FIG. 13D is a fragmentary front elevational view of a top end of the cannulated cortex drill.
Figure 15A:
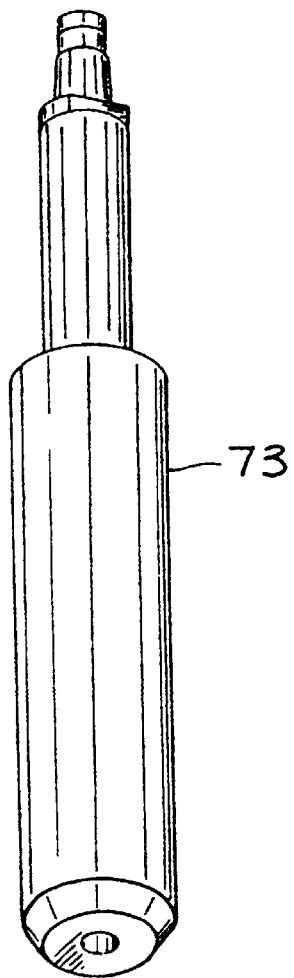
FIG. 15A is a perspective view of the cannulated reamer.
Figure 15B:
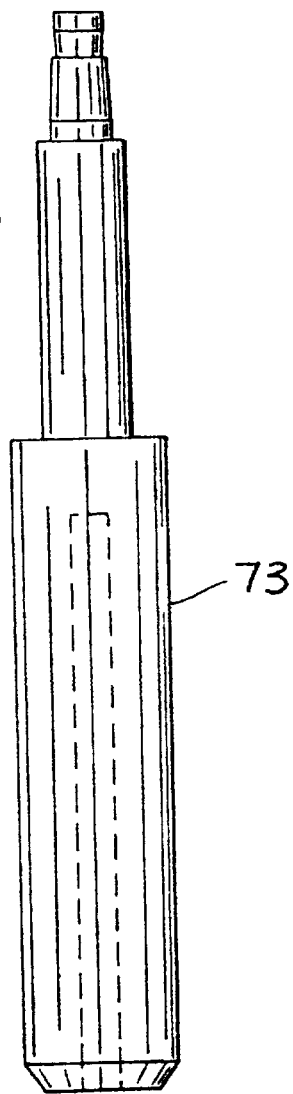
FIG. 15B is an elevational view of a cannulated reamer.
Figure 15C:
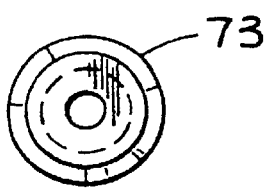
FIG. 15C is a bottom end view of the cannulated reamer.
Figure 15D:
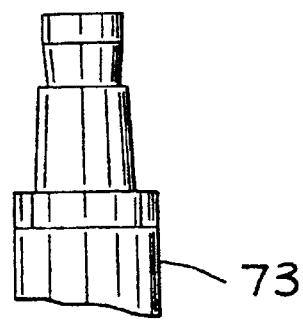
FIG. 15D is an enlarged, fragmentary elevational view of the cannulated reamer showing an upper end.

A number of calcar millers (not shown) are provided having progressively larger diameters to gradually increase the side of the hole formed in the femur F. A final calcar miller 51 (FIGS. 11A–11C) is sized to mill the first bore B1 in the medial endosteum to provide a close fit between the prosthesis 1 and the medial endosteum.

A cannulated pin guide 53 (FIGS. 12A–12D) is sized to be received through the guide tube 49 of the calcar miller guide 45 and to be slidably received in the first bore B1 created by a calcar miller 51 in the femoral neck N. The cannulated pin guide 53 has a central axial passage 55 to slidably receive a trocar point guide pin 57 (FIG. 4N) and a drill point guide pin 59 (FIG. 4P). The trocar point guide pin 57 and the drill point guide pin 59 have the same diameter, e.g., 3.5 mm.

A cannulated cortex drill 61 (FIGS. 13A–13D) is sized to be slidably received over the drill point guide pin 59. The cannulated cortex drill 61 is sized to drill a bore through the posterolateral femoral cortex C that is slightly smaller in diameter than the distal stem of the prosthesis 1 (e.g., 9 mm for a 9.5 mm diameter prosthesis stem).

An offset reaming guide, generally indicated at 63 (FIGS. 14A–14E), is sized to be slidably received in the first bore B1. The offset reaming guide 63 comprises a trunnion 65 and guide finger 67 mounted on a platform 69, and a distal end section 71. The distal end section 71 of the offset reaming guide 63 is sized (14 mm in the illustrated embodiment) to allow passage through the first bore B1 and has a bullet distal end to facilitate passage through the first bore. The exterior shape of the platform 69 (as seen from the ends of the reaming guide 63) is generally that of non-overlapping surfaces of two axially parallel, radially overlapping cylinders (see FIGS. 14C and 14E). A larger cylinder 69A of the overlapping cylinders coaxial with the axis of the distal end section 71 of the reaming guide 63 is larger than that of a smaller cylinder 69B. The smaller cylinder 69B is cut on a plane angling downwardly toward the intersection with the larger cylinder 69A. The largest transverse dimension of the platform 69 is about 15 mm to provide line-to-line fit with the first bore B1. However, it is to be understood that the transverse dimension of the platform will vary depending upon the size of the bone.

The guide finger 67 is disposed parallel to and generally in registration with the trunnion 65. The guide finger 67 engages the endosteal wall in the femur F to facilitate holding the trunnion 65 in position as a cannulated reamer 73 (see FIGS. 15A–15D) cuts the bone. The trunnion 65 is cylindrical and offset about 6 mm from the central longitudinal axis of the distal end section 71 of the offset reaming guide 63. The precise offset distance will vary depending upon the size of the bone in which the prosthesis 1 will be installed. The trunnion 65 is sized to receive the cannulated reamer 73 thereon and to permit rotation of the cannulated reamer on the trunnion for reaming the bone while guiding the reamer along a line parallel to the axis AX-1 of the first bore B1 formed in the femur F. The cannulated reamer 73 forms the second bore B2.

A calcar planing guide, generally indicated at 75, comprises a stem 77 including an upper portion 77A and a lower portion 77B, and a trunnion 79 generally coaxial with the stem (FIGS. 16A–16D). The calcar planing guide 75 has a bullet shaped distal tip to aid in passage through the first bore B1. The shape of the stem 77 is generally the same as that of the prosthesis 1 except that the lower stem portion 77B is smooth (i.e., lacking the splines 19 of the prosthesis). The upper portion 77A of the stem is received in a double bore (first B1 and second B2) arrangement formed in the femur neck. The calcar planing guide 75 fits snugly in the first and second bores B1, B2 to hold the planing guide from moving within the femur F. The exterior surface of the stem 77 is smooth in the embodiment illustrated in FIGS. 16A and 16B.

Figure 16D:
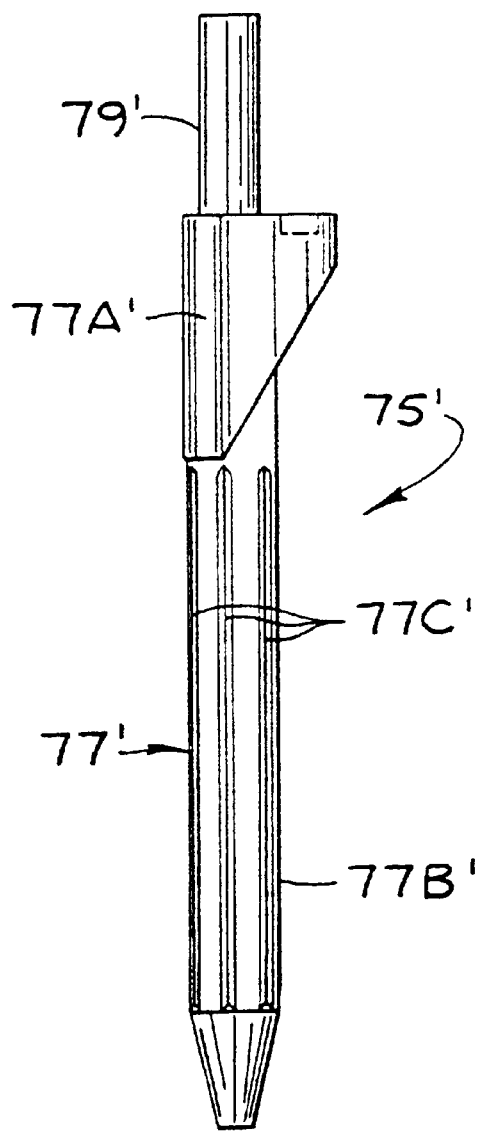
FIG. 16D is a front elevational view of a calcar planing guide of a second embodiment.
Figure 16C:
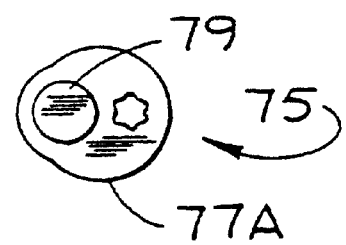
FIG. 16C is a top plan view of the calcar planing guide.

However, the calcar planing guide should preferably correspond closely to the shape of the prosthesis 1. FIG. 16D illustrates an embodiment of a calcar planing guide 75' in which the stem 77' has splines 77C' corresponding identically to the splines 19 of the prosthesis. In the event the prosthesis 1 also had splines (not shown) on the upper portion 15 of its stem 13, similar splines (not shown) would be formed on the upper portion 77A' of the planer guide stem 77'. By more precisely matching the shapes of the stems (13, 77') of the prosthesis 1 and planing guide 75', a greater congruency of the underside (9A, 11A) of the collar 7 and the seat formed on the neck N may be achieved.

A calcar planer of the present invention (generally indicated at 81) forms a seat for the collar 7 of the prosthesis 1 on the resected neck N of the femur F (see FIGS. 17A–17C). The calcar planer 81 comprises a head, generally indicated at 83, and a shaft 85 extending axially from the head. The calcar planer head has a central axial passage 87 which receives the trunnion 79 of the planing guide 75 therein to mount the planer on the planing guide for rotation relative to the planing guide on the trunnion. The bottom 89 of the head 83 has the shape of a frustum of a cone. The angle of the cone to a plane perpendicular to the central longitudinal axis AX-1 is about 10° when the planer 81 is mounted on the planer guide 75. The side 91 of the head 83 is also conical in shape, making an angle of about 60° with the plane perpendicular to the central longitudinal axis AX-1. The shape of the head 83 corresponds closely to the shape of the underside (9A, 11A) of the collar 7.

In the event the prosthesis 7" having a flat underside 9A" is to be installed, the bottom 89' of the head 83' of the calcar planer 81' is also flat. The calcar planer 81' having a flat bottom 89' is illustrated in FIG. 18M. It is believed the use of the flat bottomed calcar planer 81' and prosthesis 1" increases the chance of obtaining a very high level of congruency between the prosthesis and the seat on the neck N formed by the calcar planer.

(c) Method of Implanting the Prosthesis

Figure 18A:
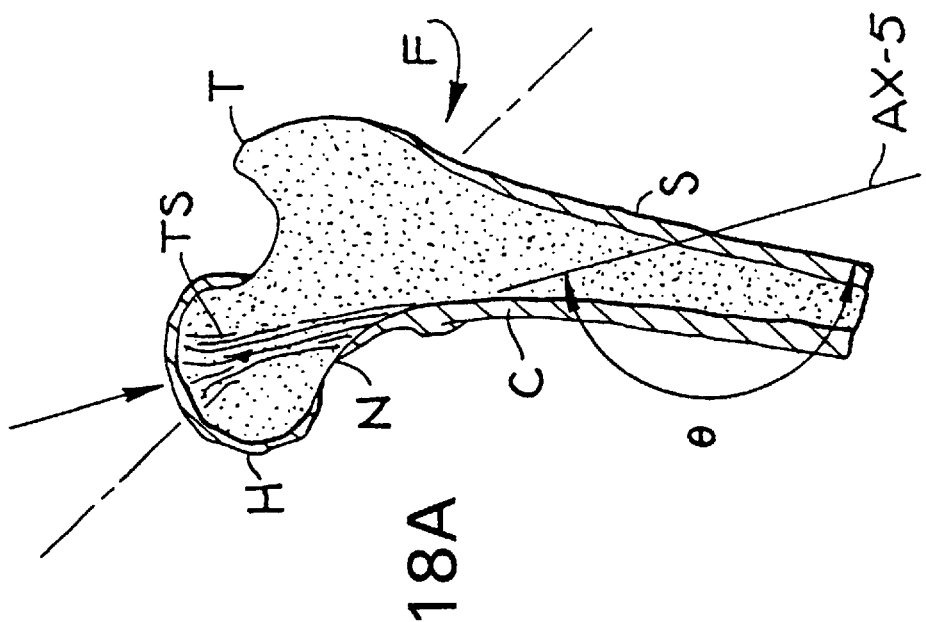

The method of the present invention for implanting the prosthesis 1 assures close replication of normal loading of the femur F (i.e., loading prior to implantation of the prosthesis). One preferred method of the present invention is illustrated in FIGS. 4A, 4B and 4M–4S. A lesser preferred method is illustrated in FIGS. 4A–4L. A most preferred method is illustrated in FIGS. 18A–18P. A femoral head-neck prosthesis which fails to replicate normal loading conditions will change the stress distribution through the femur F. As mentioned in U.S. Pat. No. 4,998,937, incorporated herein by reference, according to Wolff's law these changes in stress distribution eventually cause alterations in the internal structure of the bone. Those portions subject to a lesser stress than before are likely to deteriorate and those subject to greater stress than before are likely to thicken. Excessive increases in stress over those associated with normal loading may kill the bone cells if the stress is applied over an extended period of time. To replicate normal loading, the method of the present invention aligns the stem 13 of the prosthesis 1 with the average compression loading vector for the particular femur, which vector is variable from person to person.

Referring to FIG. 1A, the human femur F has two externally visible axes: the axis of the femoral neck AX-4 and the axis of the femoral shaft AX-3. However, the bone is not loaded along either of these two visible axes, but rather is loaded through a third axis (parallel to the average compression loading vector) which is not externally apparent. In response to compressive loading and the strain energy density experienced by the femur F, reinforcing lines of bone, which are called compression trabeculae, form within the femur. The collection of these reinforcing lines is the compression trabecular stream TS. The particular collection of compression trabeculae in the femur neck, as shown in FIG. 1A, is referred to as the medial trabecular stream TS, and the average direction of the medial trabecular stream may be referred to as the medial trabecular stream axis AX-5. Angle Θ which axis AX-5 makes with the central longitudinal axis of the femur shaft AX-3 generally ranges from 140 to 170 degrees. In practice, this angle is measured from a profile X-ray of the hip between the axis AX-5 and a lateral surface of the femur F (see FIG. 4A). The use of the medial trabecular stream TS to position the prosthesis 1 is discussed in U.S. Pat. No. 4,998,937.

To install the prosthesis 1 in the femur F in accordance with the method of this invention, the hip joint and the lateral side of the femur are first surgically exposed. A vertical plane P-1 through the central longitudinal axis AX-2 of the femoral neck is typically at an angle of approximately 15 degrees anterior to a lateral-medial plane P-2 through the central longitudinal axis AX-3 of the femoral shaft, as shown in FIG. 1B. This angle is commonly referred to as the "anteversion" of the femoral neck. Accordingly, the angle guide 29 is positioned radially on the femur F such that the vertical axis of bracket 31 lies in plane P-1 approximately 15 degrees posterior from the lateral-medial plane P-2 (since the bracket is lateral of axis AX-3 and the femoral neck 7 is medial). In this position, a vertical plane P-3 through guide sleeve 33 should be parallel to plane P-1. In addition, the angle guide 29 is positioned proximally-distally on the femur F such that the upper end of guide sleeve 33 is centered with respect to the base of the femoral neck, as shown in FIG. 1B. The angle guide 29 is then clamped on the femoral shaft S by a clamp (not shown). The guide sleeve 33 is adjusted, by loosening screw 35, relative to the bracket 31 so that its angle relative to the central axis AX-3 of the femur shaft S matches the angle e of the medial trabecular stream TS. This is accomplished by aligning pointer 37 of the guide sleeve with the appropriate angle indicated on the faceplate 31C of the bracket 31.

Figure 4B:
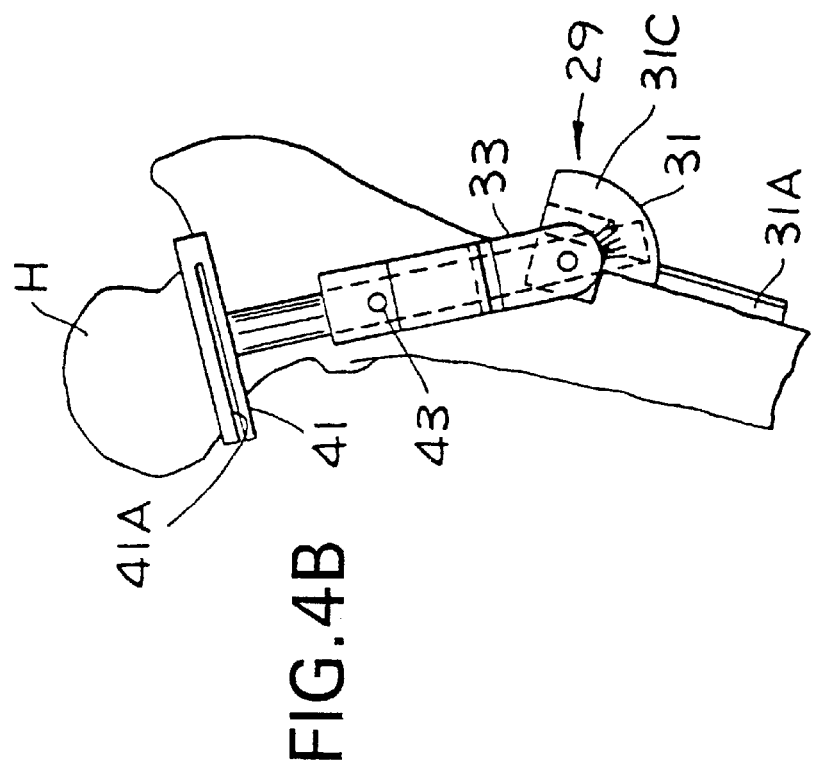
FIG. 4B is a view showing the angle guide and the saw guide around the femur for femoral neck resection.
Figure 4A:
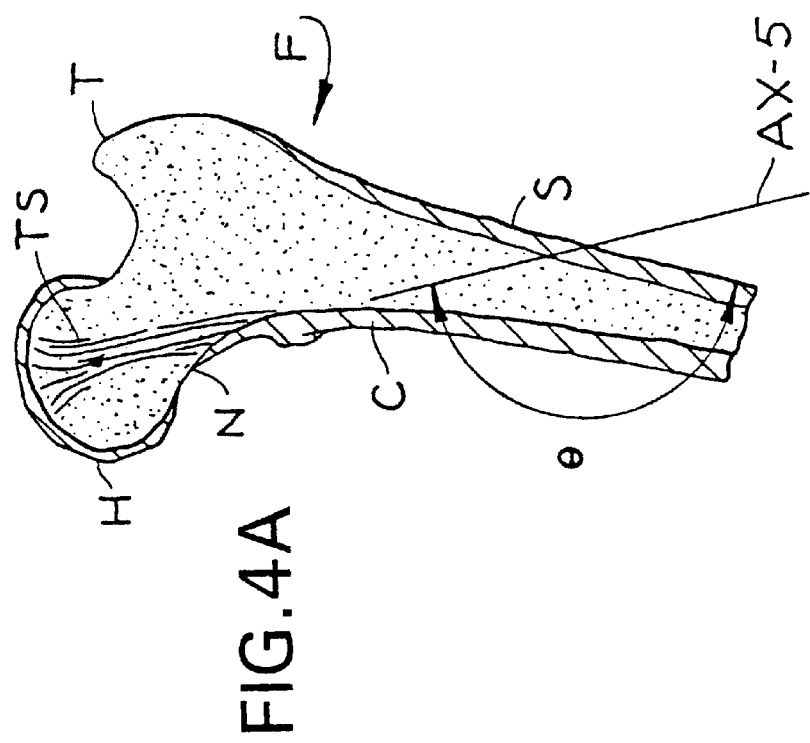
FIGS. 4A–R are schematic views of a lesser preferred embodiment and a preferred embodiment of a method of implanting the prosthesis.
Figure 4D:
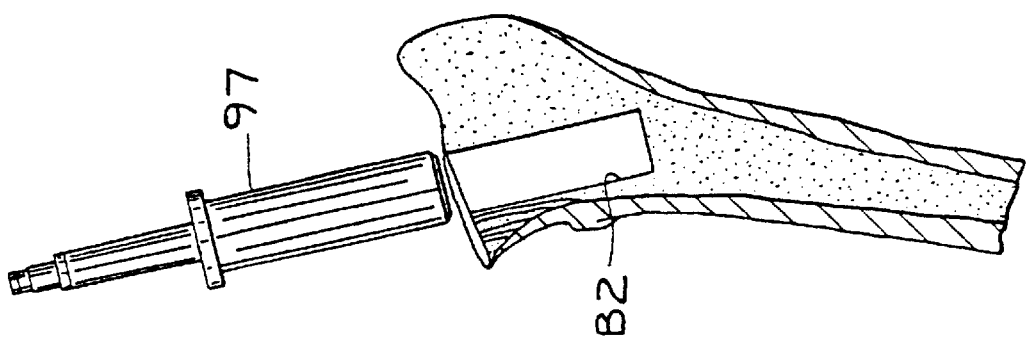
FIG. 4D is a view showing the reamer for reaming the second bore in the femoral neck.
Figure 4C:
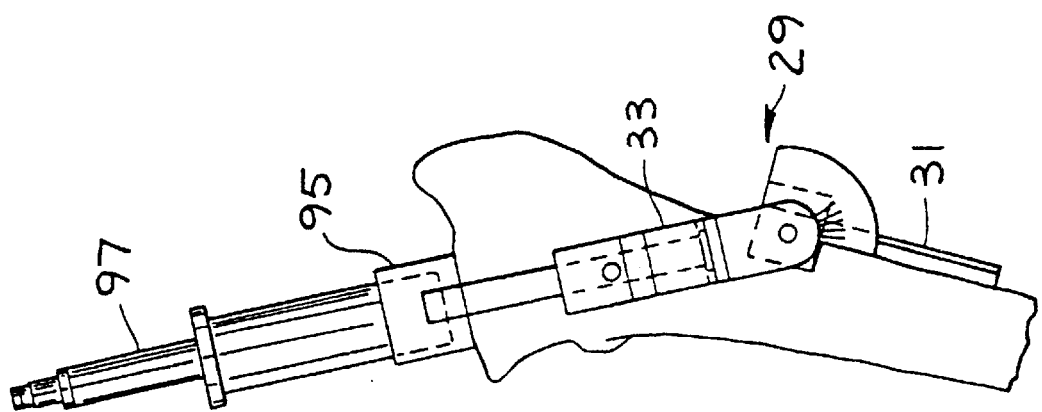
FIG. 4C is a view showing the angle guide, a reamer guide and a reamer for reaming of the second bore in the femoral neck.

The saw guide Al is positioned (proximally-distally) on guide sleeve 33 such that the sawcut slot 41A is located adjacent the base of the femoral neck N and generally aligned with the upper surface of the lateral femoral cortex of the femur F, as shown in FIG. 4B. In this position, the sawcut slot should be perpendicular to the medial trabecular stream TS. Set screw 43 is tightened to firmly attach the saw guide 41 in the guide sleeve 33 of the angle guide 29.

With the saw guide 41 in place, the femoral neck N is cut with an oscillating saw (not shown) by passing the saw through the sawcut slot 41A to form a cut surface extending from the lateral femoral cortex at an angle of approximately 60 degrees with respect to the central longitudinal axis AX-3 of the femoral shaft S. The saw guide 41 is then removed from the guide sleeve 33, leaving the angle guide 29 attached to the femoral shaft S in its original position, and the femoral head H is removed.

If a total hip replacement (i.e., replacement of the femoral head H and acetabulum (not shown) is required, the acetabulum should now be prepared.

In the first preferred embodiment, as shown in FIGS. 4A, 4B and 4M–4S, the calcar miller guide 45 is secured to the guide sleeve 33, which effectively centers the calcar miller guide with respect to the cut surface of the femoral neck N. The angle guide 29 also aligns the calcar miller guide 45 parallel to the axis AX-5. A starter hole is drilled into the femoral neck 7.

A miller (not shown) of relatively small milling diameter is slidably received in the calcar miller guide 45 to mill the femoral neck. The femoral neck N is milled by a progression of end and side cutting millers, with each succeeding miller having a larger diameter than the preceding miller. The femoral neck N has an inner lining (or surface) referred to as the endosteum. The final milling diameter is determined for the individual femur to provide an appropriate diameter of the first bore B1 adjacent to the medial endosteum. The calcar miller 51 of the appropriate diameter mills a bore in the medial endosteum to the final diameter (e.g., 15 mm). The calcar miller 51 is then removed from the calcar miller guide 45 (FIG. 4M).

Figure 4F:
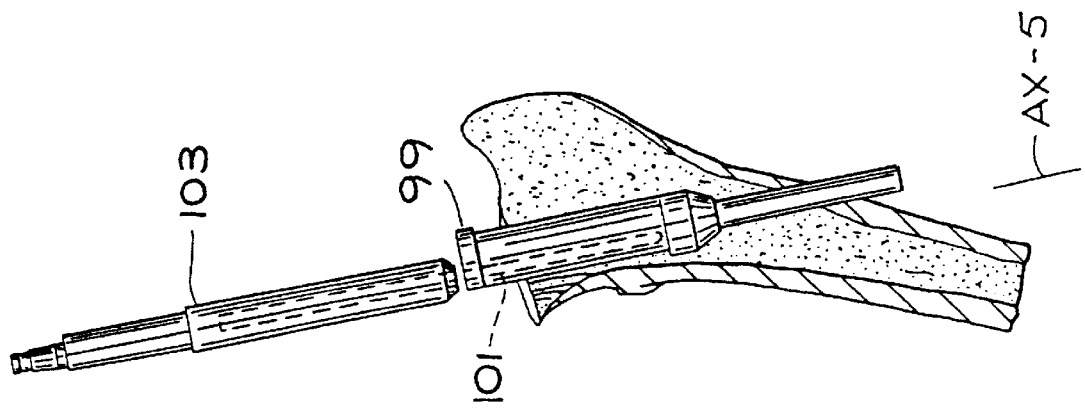
FIG. 4F is a view showing the calcar milling guide and calcar miller for milling the first bore in the femoral neck with the angle guide omitted for clarity.
Figure 4E:
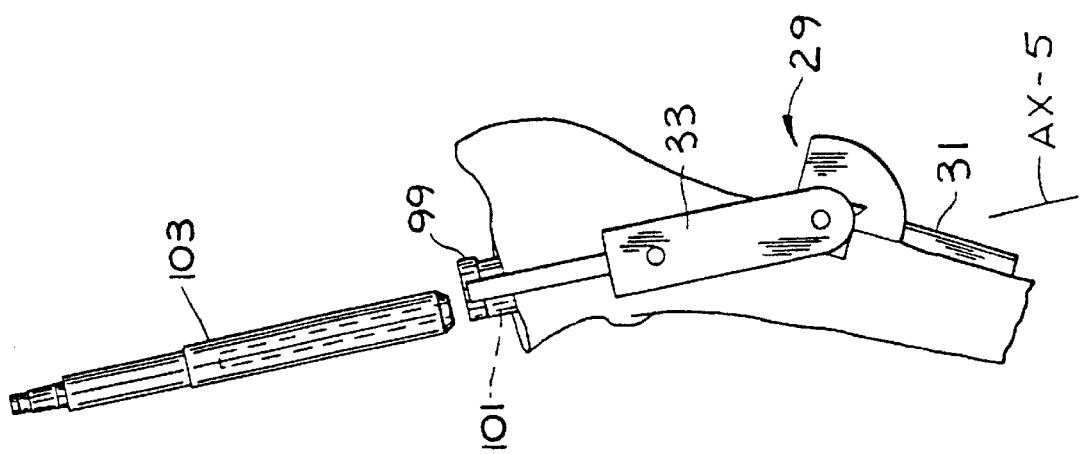
FIG. 4E is a view showing the angle guide, calcar milling guide and calcar miller for milling the first bore in the femoral neck.
Figure 4H:
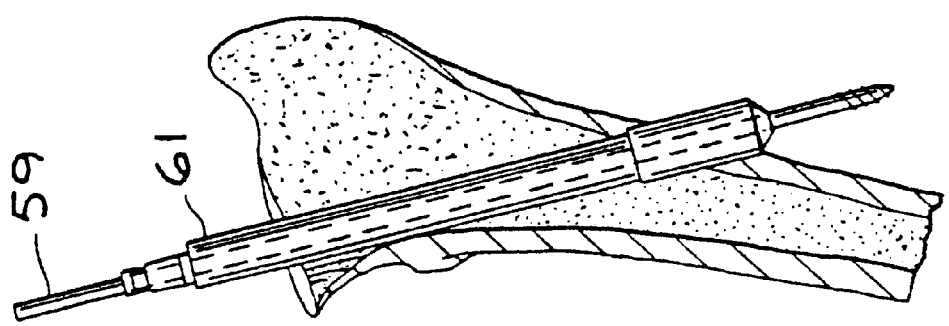
FIG. 4H is a view showing the drill point guide pin and a cannulated cortex drill for drilling through the lateral femoral cortex.
Figure 4G:
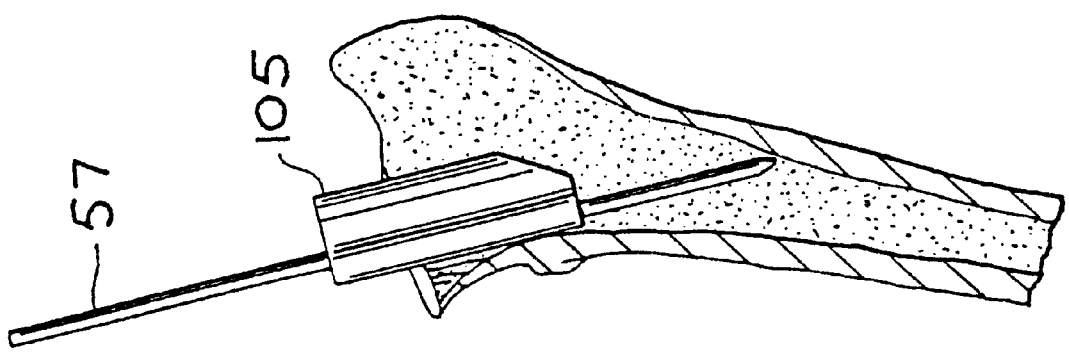
FIG. 4G is a view showing a drill pin guide, a trocar point guide pin and a drill point guide pin for drilling through the lateral femoral cortex.
Figure 4J:
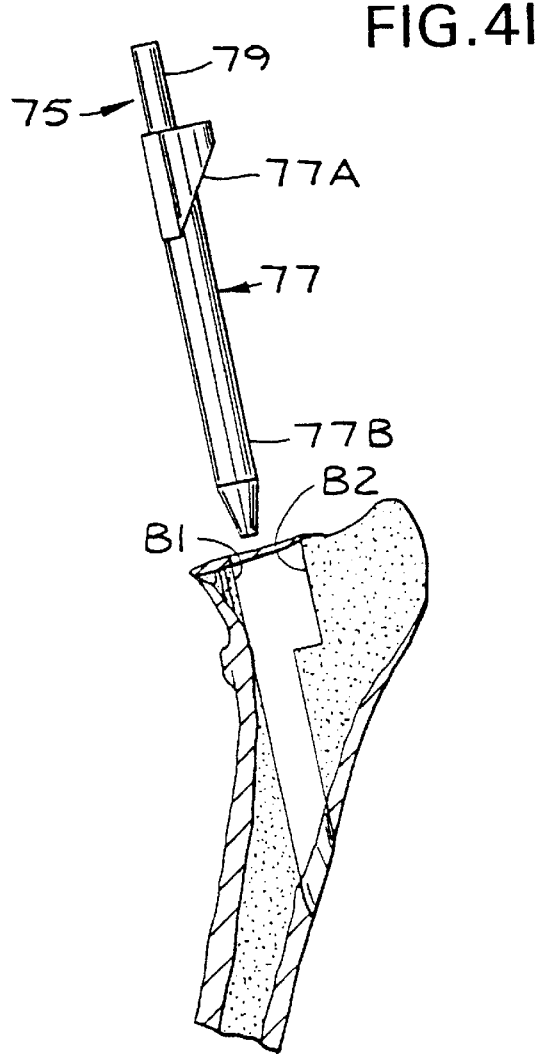
FIG. 4J is the view of FIG. 4I, but with the calcar planing guide removed.
Figure 4I:
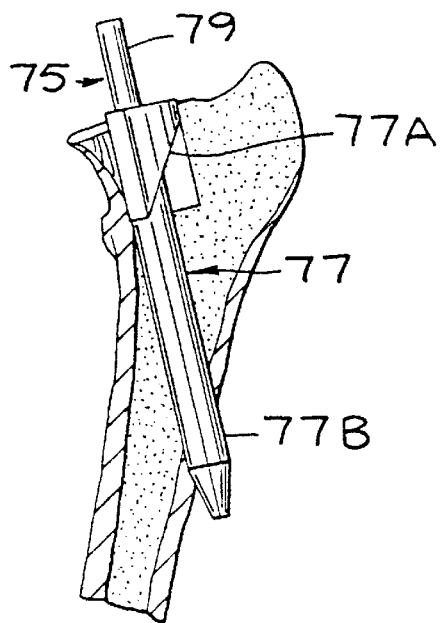
FIG. 4I is a view showing the insertion of a calcar planing guide in the femoral neck.
Figure 4K:
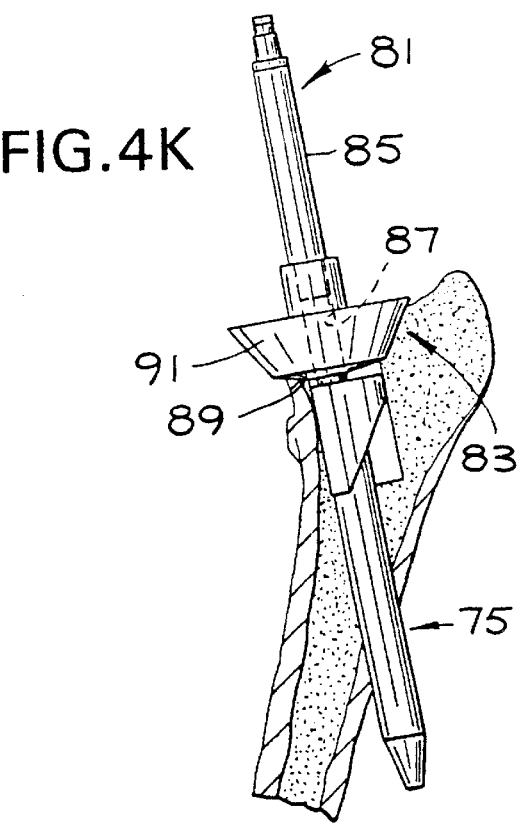
FIG. 4K is a view showing the calcar planing guide and the calcar planer for planing of the femoral neck.
Figure 4L:
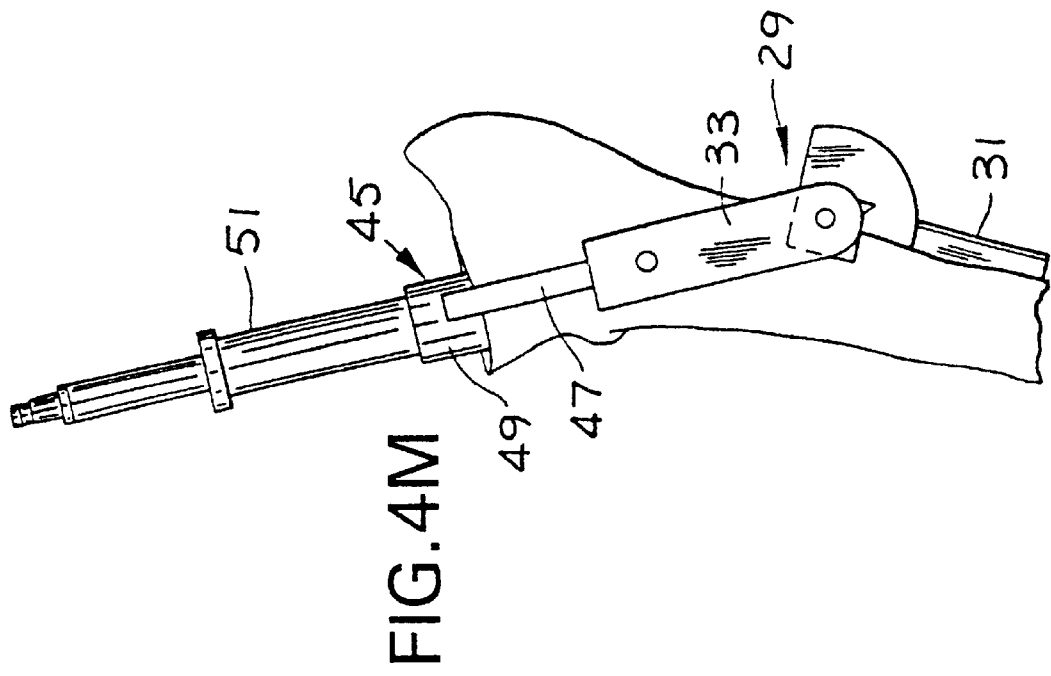
FIG. 4L is a view showing the implantation of the prosthesis.
Figure 4M:
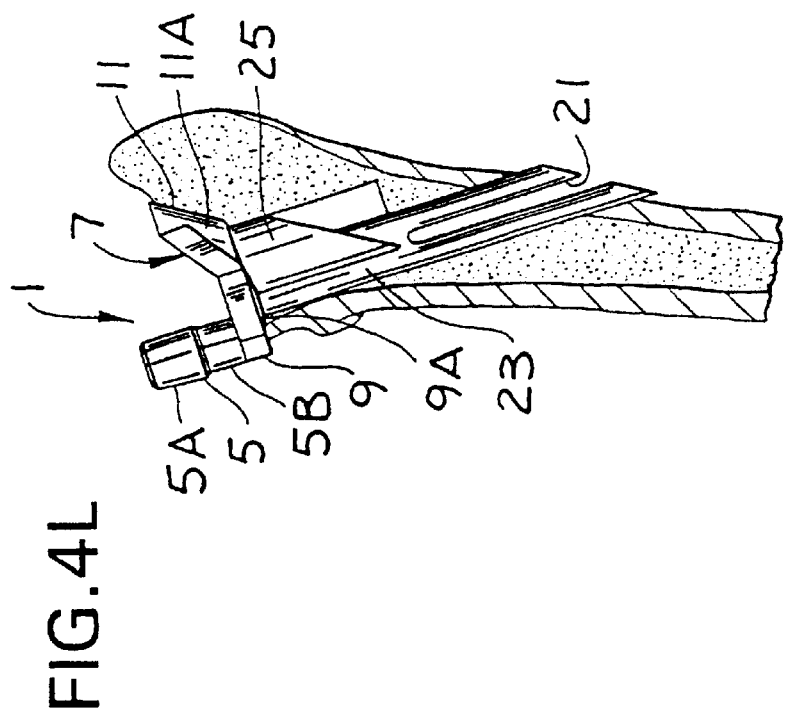
FIG. 4M shows the start of the more preferred implantation steps and is a view showing the calcar miller for milling the first bore.
Figure 4P:
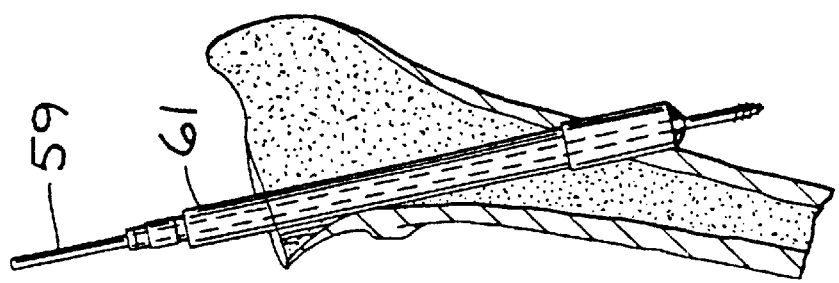
FIG. 4P is a view showing the drill point guide pin and cannulated cortex drill for drilling through the posterolateral femoral cortex.
Figure 4N:
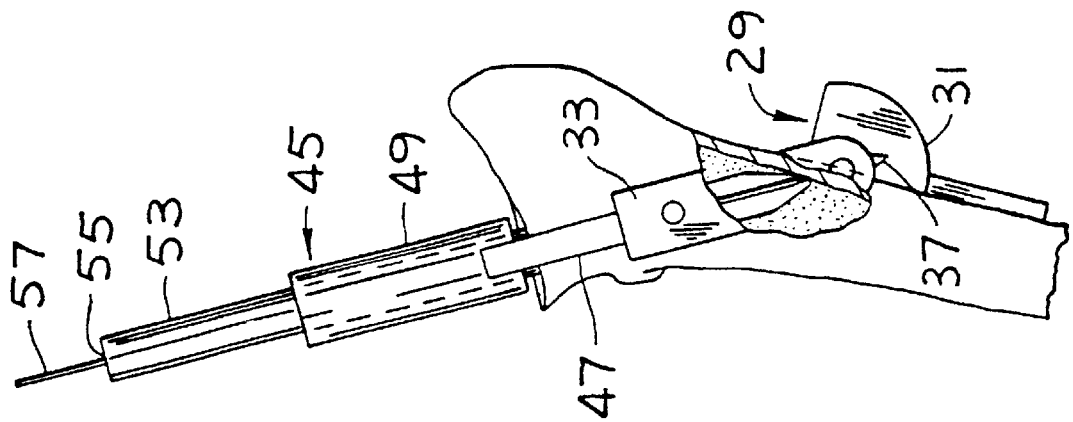
FIG. 4N is a view showing the angle guide, calcar milling guide, cannulated pin guide, trocar point guide pin and drill point guide pin for drilling through the posterolateral femoral cortex.

As shown in FIG. 4N, the cannulated pin guide 53 is received in the calcar miller guide 51 and into the first bore B1 in the medial endosteum. The trocar point guide pin 57 is received in the cannulated pin guide axial passage 55 to make a starter mark on the lateral endosteum. After the starter mark is made, the trocar point guide pin 57 is removed from the passage 55. The drill point guide pin 59 is then received in the cannulated pin guide axial passage 55 and is used to drill through the posterolateral femoral cortex C, forming an oblique hole in the posterolateral femoral cortex. The drill point guide pin 59 is left in place after drilling the oblique hole in the cortex, the cannulated pin guide 53 is removed from the femur F and the calcar miller guide 45 is removed from the guide sleeve 33 of the angle guide 29.

As shown in FIG. 4P, the cannulated cortex drill 61 is received over the drill point guide pin 59 to drill through the posterolateral femoral cortex C on the same axis as the first bore B1 milled by the calcar miller 51. Cortex drill 61 drills the oblique hole to a diameter that is smaller than the first bore B1 formed in the femur F. The cannulated cortex drill 61 and the drill point guide pin 59 are then removed from the femur 3.

Figure 4S:
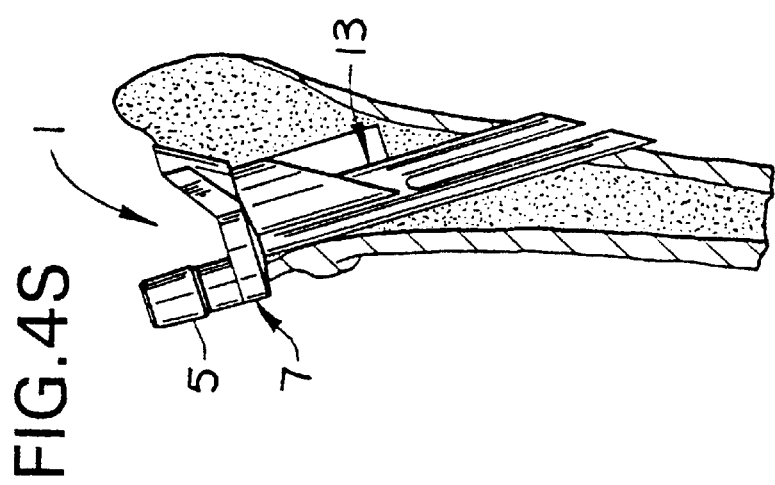
FIG. 4S is a view showing the implanted prosthesis.

The offset reaming guide 63 is then placed into the first bore B1 bullet end first. A first cannulated reamer (not shown) is received on the trunnion 65 to ream the second bore B2 in the femoral neck N which is parallel to the first bore B1. A progression of cannulated reamers (not shown) are used, with each succeeding reamer having a larger diameter. The final cannulated reamer 73 reams the second bore B2 to a diameter which achieves line-to-line contact between the prosthesis 1 and the endosteum (FIG. 4Q). After the second bore B2 is reamed to a depth to accommodate the upper stem portion 15 of the prosthesis 1, the cannulated reamer 73 and the offset reaming guide 63 are removed from the femur F.

Figure 4R:
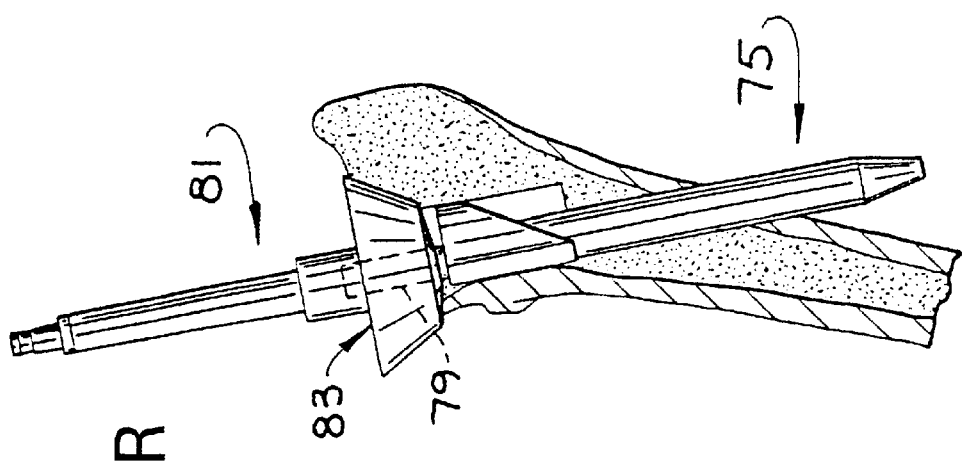
Figure 4Q:
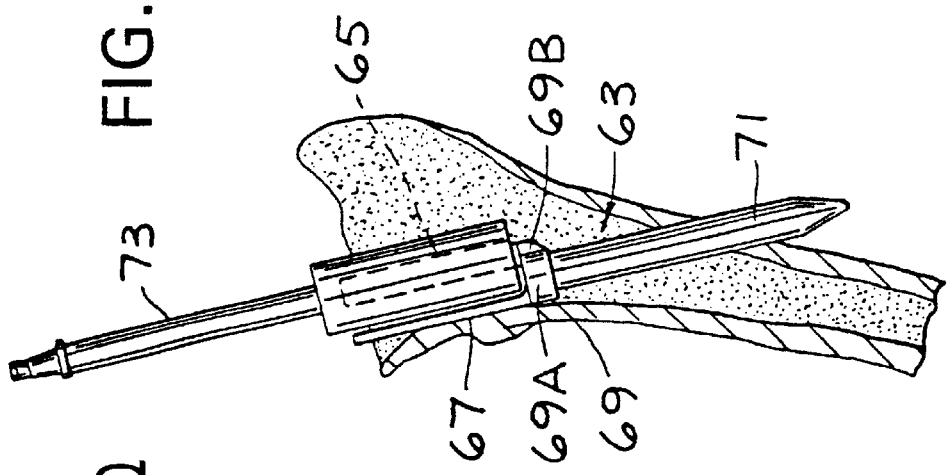
FIG. 4Q is a view showing the offset reaming guide and cannulated reamer for reaming the second bore in the femoral neck.
Figure 5C:
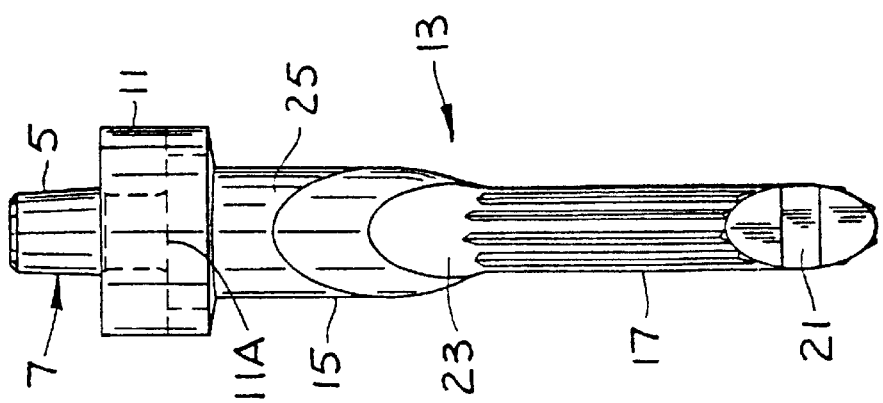
FIG. 5C is a left side elevational view thereof.
Figure 5B:
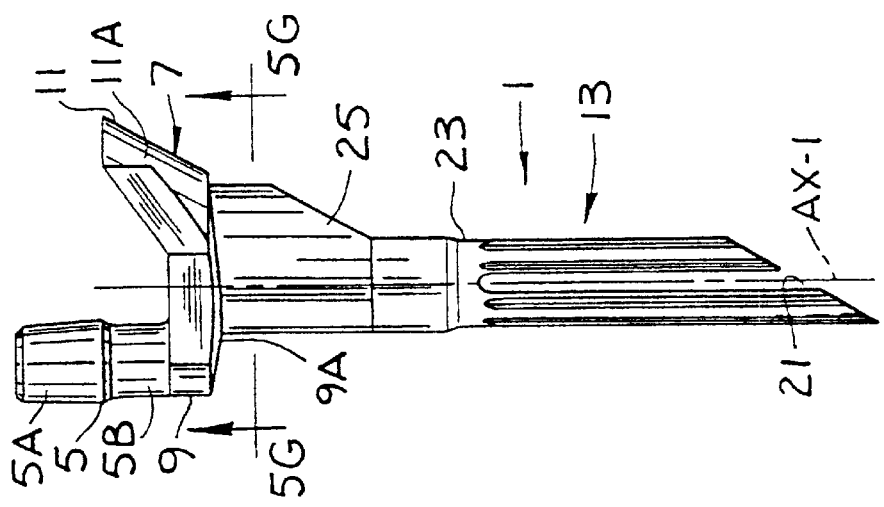
FIG. 5B is a front elevational view thereof.
Figure 5A:
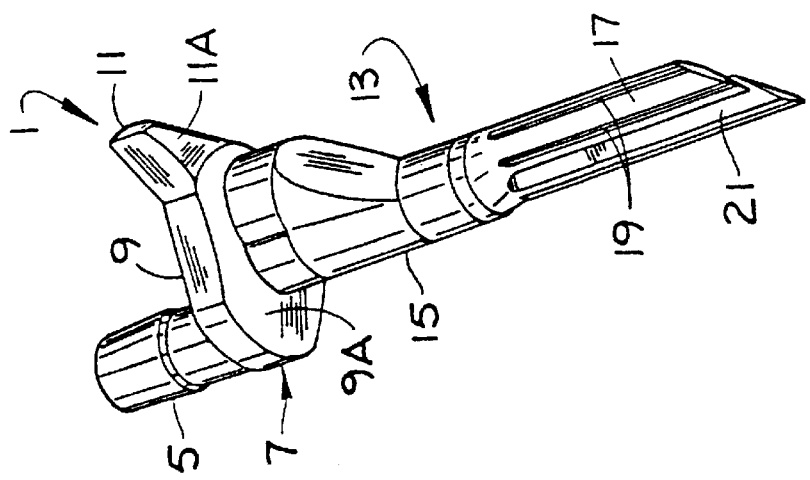
FIG. 5A is a perspective view of the split stem prosthesis of FIG. 1.
Figure 5F:
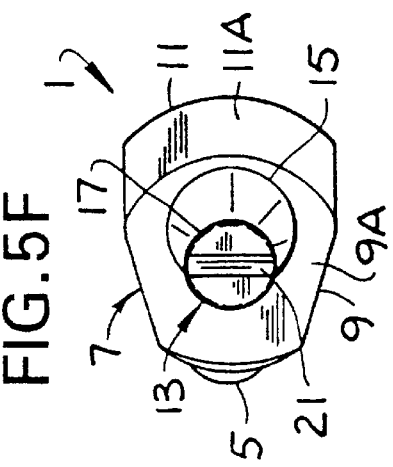
FIG. 5F is a bottom plan view of the split stem prosthesis.
Figure 5H:
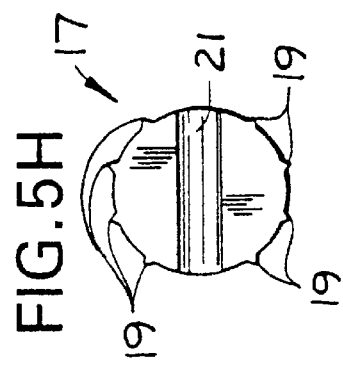
FIG. 5H is an enlarged bottom end view of the stem of the split stem prosthesis showing splines on the stem.
Figure 5E:
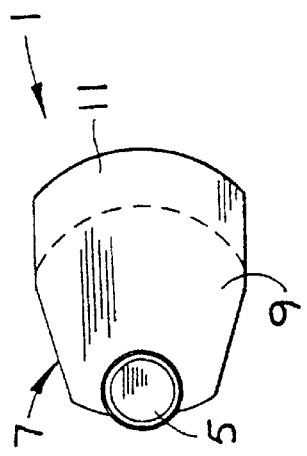
FIG. 5E is a top plan view thereof.
Figure 5G:
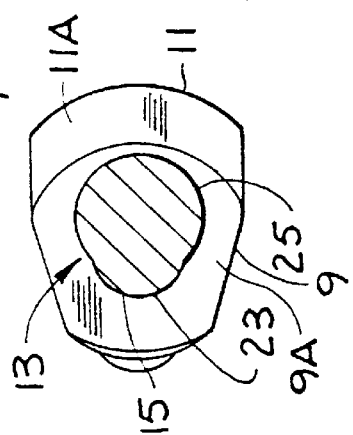
FIG. 5G is a sectional view of the split stem prosthesis taken in the plane of line 5G—5G in FIG. 5B.
Figure 5D:
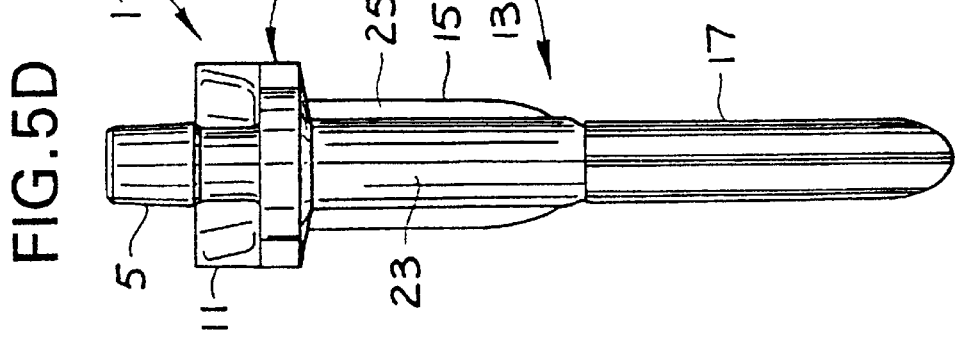
FIG. 5D is a right side elevational view thereof.

Referring to FIG. 4R, the calcar planing guide 75 is inserted into the proximal side of the first bore B1 and through the oblique hole in the posterolateral cortex C. The central longitudinal axis of the trunnion 79 and the stem 77 of the calcar planing guide 75 are collinear with the first bore B1. The calcar planer 81 is then placed on the trunnion 79 and the surface of the femoral neck is planed generally perpendicular to the axis (AX-1) of the first bore B1 while even pressure is applied to the calcar planer to form a seat for the collar 7 of the prosthesis 1. The greater trochanter T is substantially preserved by the calcar planer 81. Only an angled segment of the trochanter T is cut away providing an angled seat for the flange 11 of the collar 7. In this way, a secure engagement of the prosthesis 1 on the cortical bone C of the upper femur is achieved without sacrificing a substantial portion of the trochanter T (FIG. 1).

The bottom 89 of the calcar planer 81 is slightly cupped so that the portion of the seat on the femoral neck N slopes downwardly toward the axis AX-1. The shape of this portion of the seat is complimentary to that of the underside 9A of the prosthesis collar 7. The cup shape of the seat on the femoral neck N helps to locate the prosthesis 1. Moreover, when the underside of the collar 7 and the seat are congruent, the entire area of the seat engages the underside (9A, 11A) of the collar 7 and is subjected to loading by the prosthesis 1. Loading of the bone material of the seat over the entire area of engagement with the collar surface (9A, 11A) prevents resorption (withdrawing) of the bone after the prosthesis 1 is implanted. However, although macroscopic congruence is important, microscopic roughness or porosity of the collar undersurface (9A, 11A) possibly combined with bioactive or chemical coating (e.g., calcium phosphate compound) allows an ingrowth of bone from the seat which facilitates bonding of the collar surface with the seat. Because the collar undersurface (9A, 11A) achieves one hundred percent cortical contact and transmits substantially one hundred percent of the cortical loading, the chemical coating is used only on the underside of the collar 7 and at no locations on the stem 13. After planing, the calcar planer 81 and the calcar planer guide 75 are removed.

The prosthesis 1 (without the ball 3) is then implanted by driving the stem 13 into the first bore B1 as shown in FIG. 4S. The splines 19 of the stem bite into the walls of the first bore B1 and the stem protrudes slightly through the oblique hole so that cortical bone does not later grow over the end of the stem. Growth of bone over the end of the stem 13 would be undesirable since it would impede the ability of the prosthesis 1 to transmit loads from the hip to the upper femur. The upper stem portion 15 fits closely into the first bore B1. The underside 9A of the collar platform 9 is congruent with the portion of the seat which was formed by the bottom 89 of the calcar planer head 83 and the underside 11A of the flange 11 is congruent with the portion of the seat on the trochanter T formed by the side 91 of the calcar planing head.

Once the prosthesis 1 is implanted, an appropriately sized ball 3 is then locked onto the neck.

In a second, lesser preferred embodiment, the procedure is somewhat modified. Referring to FIGS. 4C and 4D, after the femoral neck N is resected, a reamer guide 95 (similar in construction to the calcar miller guide 45) is secured to the guide sleeve 33 of the angle guide 29, which effectively centers the reamer guide over the femoral neck N so that the second bore B2 is formed first. As before, the second bore B2 is formed by a progression of reamers (not shown), with each succeeding reamer having a larger diameter than the preceding reamer. The final reamer 97 has a diameter of 21 mm, so that the femoral neck N is reamed to a diameter of 21 mm. The reamer guide 95 is then removed from the guide sleeve 33, leaving the angle guide 29 attached.

A calcar miller guide 99 having a trunnion 101 is attached to the angle guide 29 and the first bore B1 is formed by milling with a series of calcar millers including final calcar miller 103 (FIGS. 4E and 4F). The angle guide 29 is removed in FIG. 4F to more clearly show the calcar miller guide 99. The calcar miller guide 99 is removed from the angle guide 29 and a drill pin guide 105 is mounted on the angle guide. Referring to FIG. 4G, the upper portion of the drill pin guide 105 has a double cylinder construction similar to the upper portion 15 of the prosthesis stem 13 to fit in the first and second bores, B1 and B2. The angle guide 29 is also not shown in FIG. 4G. The same trocar pin 57 and drill pin 59 in the more preferred embodiment are used with the drill pin guide 105 of the lesser preferred embodiment to start the distal hole in the posterolateral cortex of the femur F. The planing step and instrumentation are substantially the same as described for the method of the first more preferred embodiment.

In a third, most preferred embodiment shown in FIGS. 18A–18P, the procedure and some of the tools are modified. The initial step (FIG. 18A) of determining the angle of the medial trabecular stream TS is carried out exactly as described above in reference to FIG. 4A. Once the angle of the medial trabecular stream with respect to the central longitudinal axis AX-3 of the bone is determined, the angle of the guide sleeve 33 of the angle guide 29 is set as described above. In the most preferred embodiment, this angle is checked using a protractor device indicated generally at 101. The protractor device has a stop 103 against which the bracket 31 of the angle guide 29 is placed. A pivotable arm 105 can be moved, by loosening set screw 107, to the angle corresponding to the angle of the medial trabecular stream TS. The arm 105 is fixed by the screw 107 and the guide sleeve 33 should be in face-to-face engagement with the arm. If not, the sleeve guide 33 is turned until it matches the angle of the arm 105 of the protractor device 101. The larger scale of the protractor device 101 permits a more accurate setting of the angle guide 29.

Figure 18D:
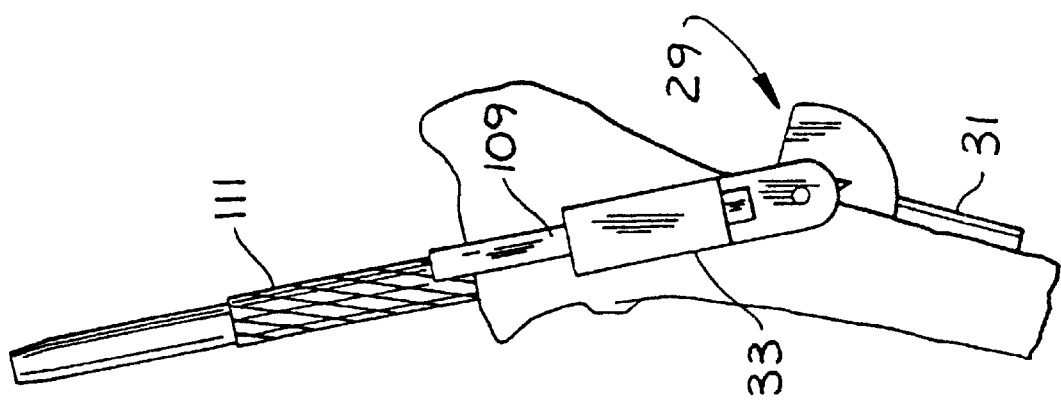
FIG. 18D is a view showing an initial reaming step.
Figure 18C:
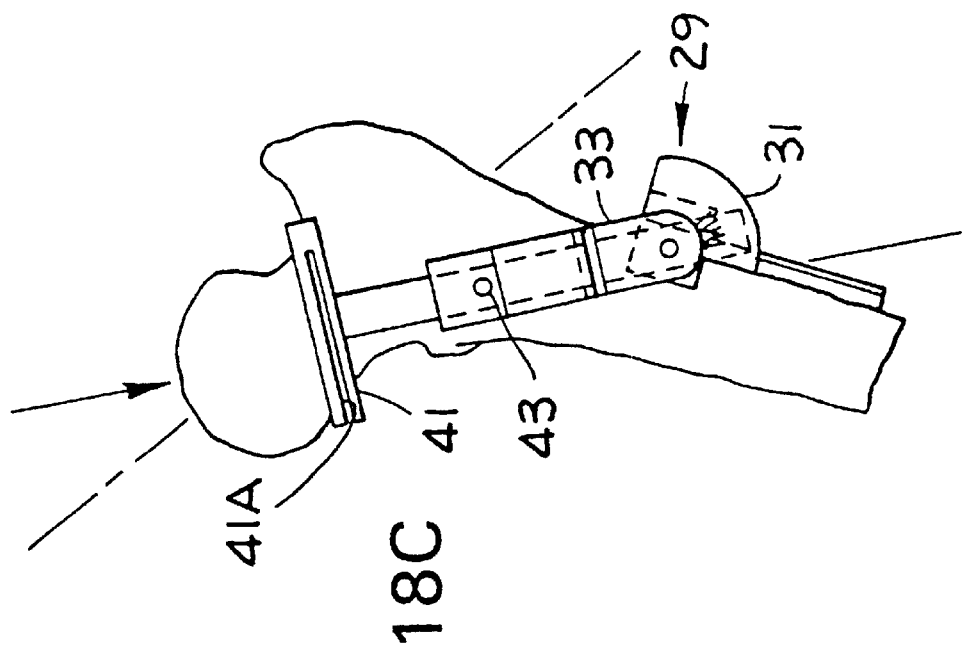
FIG. 18C is a view showing the angle guide and the saw guide around the femur for femoral neck resection.

As illustrated in FIG. 18C, the angle guide 29 is attached to the surgically exposed femur and the saw guide 41 is secured in the angle guide. The procedure for resecting the femoral head is the same as described above in reference to FIG. 4B. The saw guide 41 is removed from the angle bracket and replaced with a visual sighting bar 109 which extends generally upwardly from the guide sleeve 33 and beyond the resected neck N of the femur. As shown in FIGS. 18D and 18E, a reamer 111 is then directed by the surgeon along the angle indicated by the visual sighting bar 109 into the femur to form an initial hole HO in the femur. The hole HO thus formed has a longitudinal axis parallel to the medial trabecular stream TS and with the proper anteversion, both of which are indicated by the bar 109. The reaming may be carried out using a reamer 111 and a number of succeeding reamers of increasingly larger diameter to form the full diameter of the hole. A skilled surgeon can alternatively form the full diameter of the hole HO using only the reamer 111. In that event, the surgeon moves the reamer 11 in progressively larger circles until the full diameter is reached. The final diameter of the hole HO is dictated by the size and shape of the femur of the individual patient.

Figure 18F:
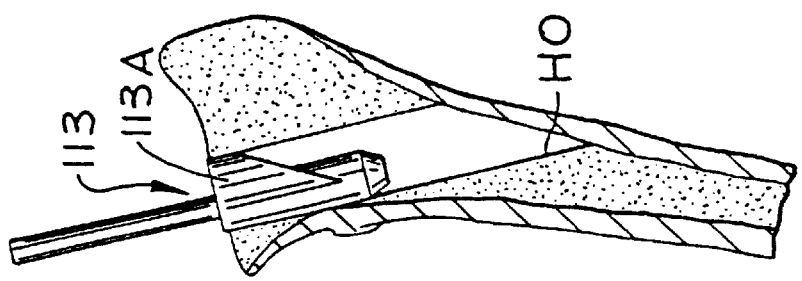
FIG. 18F is a view showing sizing the femur for selection of the appropriate prosthesis.
Figure 18E:
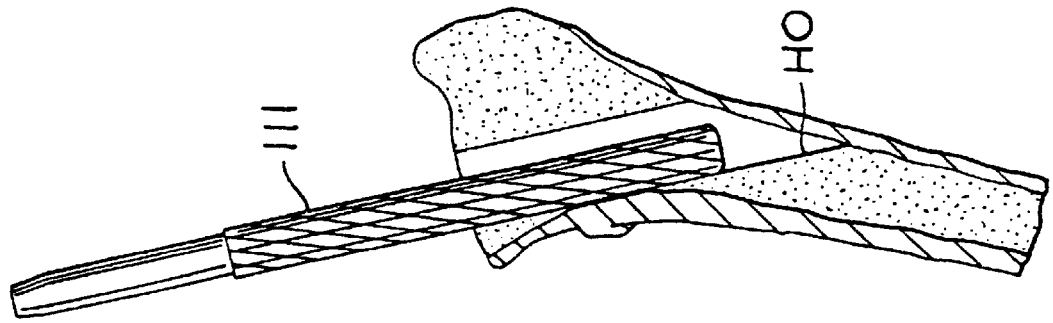
FIG. 18E is the view of FIG. 18D in vertical section with the angle guide removed.
Figure 18H:
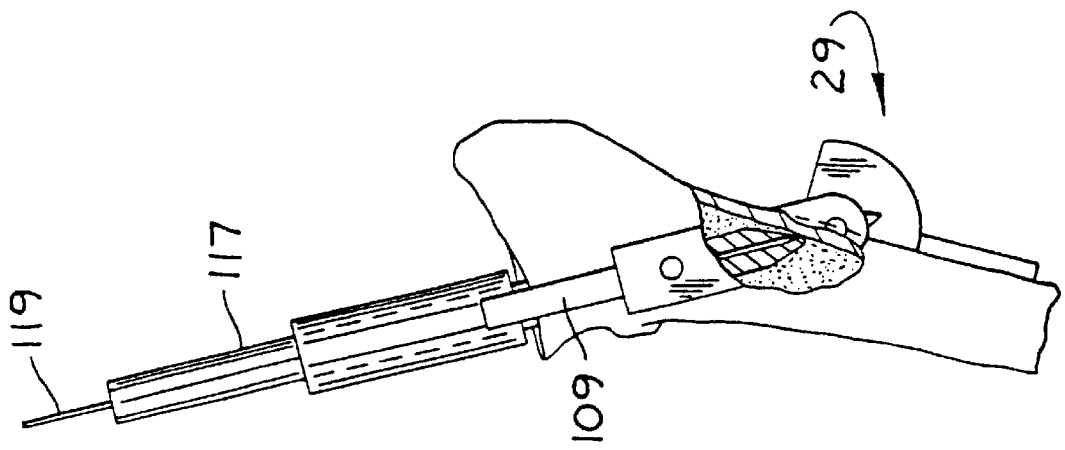
FIG. 18H is a view showing a pin guide and drill point guide pin for use in drilling through the posterolateral femoral cortex.

Sizing of the hole for the best fitting prosthesis is carried out using proximal femoral sizers 113 such as the sizer shown in FIG. 18F. The sizer 113 is substantially identical in shape to the upper portion 15" of the stem 13" of the prosthesis 7" to be implanted. The sizers range in size. For example the larger cylindrical portion 113A of the sizer may range in size from 18 to 26 mm in one millimeter increments. The sizers 113 are inserted into the hole HO parallel to the visual sighting bar 109 (not shown in FIG. 18F). Progressively larger sizers are fitted into the proximal femur to determine the dimensions of the largest prosthesis which will fit in the femur. The surgeon now knows the size of the prosthesis 1" to be implanted and the exact dimension of the bores B1, B2 needed to receive the prosthesis. The prosthesis 1" is selected to be a size larger than the largest sizer 113 which is able to fit in the hole HO. For example, if the largest sizer that would fit had a smaller diameter portion of 14.5 mm a prosthesis having a smaller diameter upper stem portion of 15 mm would be used.

Figure 18G:
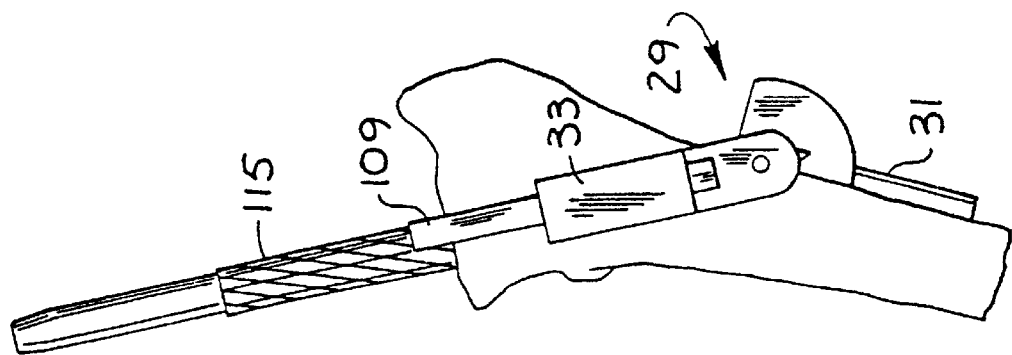
FIG. 18G is a view showing a calcar miller milling the first bore.

A reamer 115 having a diameter corresponding to the final diameter (e.g., 15 mm) of the first bore B1 is selected and used to form the first bore. As shown in FIG. 18G, the reamer is guided freehand using the visual sighting bar 109. The first bore B1 is also formed so that at least a portion of the bore is defined by the endosteum of the medial femoral cortex. Thus, the prosthesis 1" when installed will engage the hard cortical bone at this location in the bore B1. In order to drill a hole in the posterolateral femoral cortex which is precisely parallel to the medial trabecular stream TS and with the proper anteversion, a series of one piece, cannulated outrigger pin guides 117 (only one is shown) of different sizes are provided. The pin guide 117 having a diameter corresponding to that of the newly formed bore B1 is selected and inserted into the bore. The outrigger portion of the pin guide 117 is received in the guide sleeve 33 of the angle guide 29 at the same time it is inserted into the bore B1 for the most precise alignment of the pin guide. The tapered tip of the guide is advanced into the first bore B1 until it makes contact with the endosteum of the lateral femoral cortex.

Figure 18J:
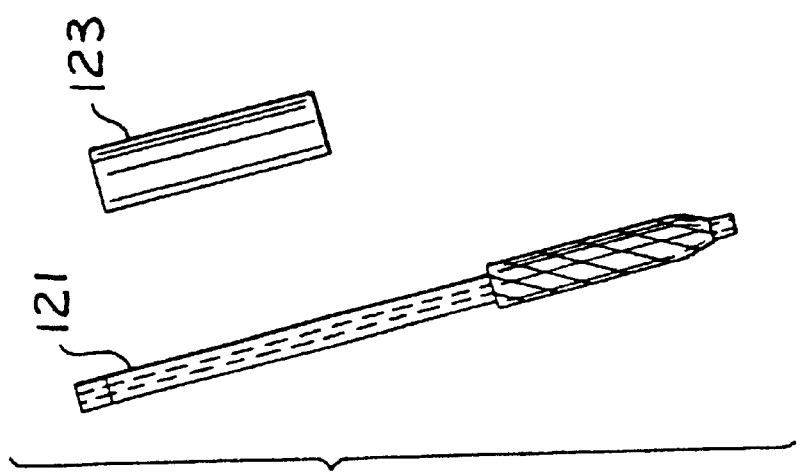
FIG. 18J shows a cortical drill and sleeve used to drill the posterolateral femoral cortex.
Figure 18I:
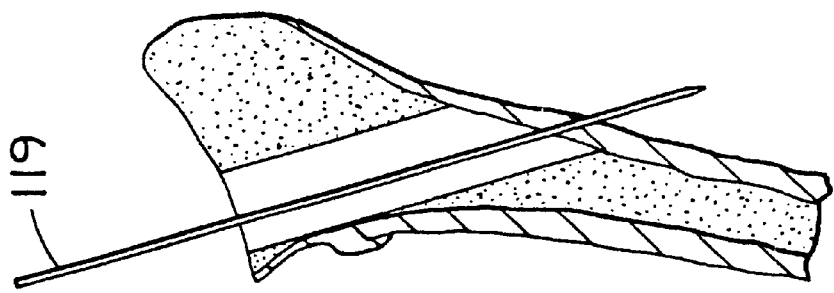
FIG. 18I is a view showing the drill point guide pin after removal of the pin guide.

A drill guide pin 119 is inserted into the pin guide 117. The orientation of the guide pin 119 in the femur is checked by making sure the angle guide 29 is still at the proper angle parallel to the medial trabecular stream TS and with the proper anteversion. Moreover, the pin guide 117 is checked to make sure it is in contact with the endosteal surface of the medial neck cortex. A drill (not shown) is attached to the guide pin 119, and it is drilled through the lateral femoral cortex. As shown in FIG. 18I, the pin guide 117 and the angle bracket 29 are removed from the femur, leaving on the guide pin 119. The next step is to drill the transcortical tunnel through the posterolateral femoral cortex. A cannulated drill 121 is selected which corresponds to the diameter of the lower portion 17" of the prosthesis 1". For example if the diameter of the lower portion 17" is to be 9.5 mm, a 9 mm cannulated drill is selected. As illustrated in FIG. 18J, the cannulated drill 121 comes with a guide ferrule 123 which is sized according to the diameter of the bore B1. Thus as shown in FIG. 18K, the guide ferrule 123 helps (along with the guide pin 119) to align the drill with the longitudinal axis of the bore B1. The cannulated drill 121 slides over the guide pin 119 with the guide ferrule 123 received on the drill and the transcortical tunnel is formed in the posterolateral femoral cortex. Care is taken during drilling to make sure the ferrule 123 remains against the medial endosteal cortex.

Figure 18L:
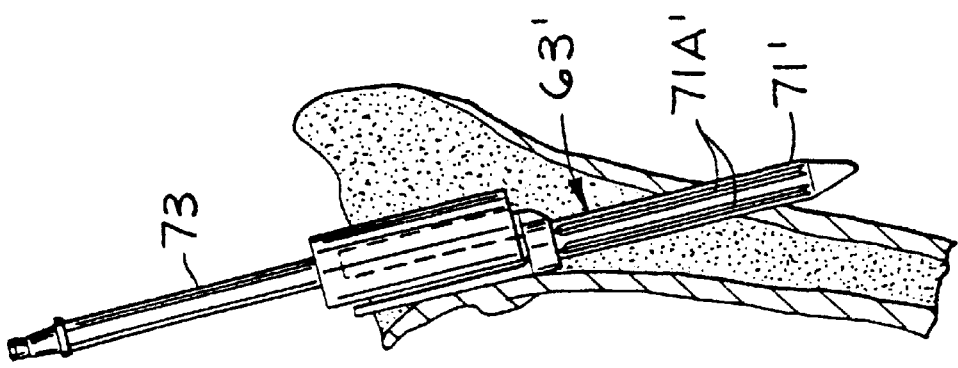
FIG. 18L is a view showing an offset reaming guide and cannulated reamer for reaming the second bore in the femoral neck.
Figure 18K:
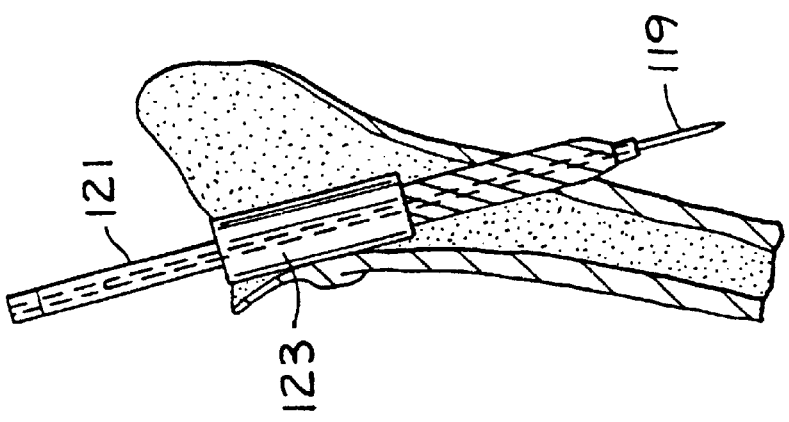
FIG. 18K shows the cortical drill as received on the guide pin after drilling through the posterolateral femoral cortex.

The second bore B2 is formed as shown in FIG. 18L, which is the same procedure as described above in relation to FIG. 4Q. However, an offset reaming guide 63' is shown in FIG. 18L which has splines 71A' for more precise orientation of the reaming guide in the femur.

As shown in FIG. 18M, the calcar planing guide 75' inserted into the bores B1, B2 is virtually identical in shape to the prosthesis 1". The planing guide 75' has splines 77C' on its lower stem portion 77B' like those of the prosthesis. The calcar planer 81' is received on the trunnion 79' of the planing guide 75' and a flat seat is formed on the femoral neck N. There is preferably a very close tolerance between the trunnion 79' and the planer 81' to avoid wobble as the planer is rotated to form the seat.

Referring to FIG. 18N the prosthesis 1" is inserted into the femur using a guide tip 125 which is attached to the end of the prosthesis. More particularly, the guide tip 125 has a stem (not shown) which is received in a hole (not shown) in the distal end of the prosthesis 1". The tip 125 is held by a friction fit in the hole. The bullet nosed shape of the tip 125 helps to keep the prosthesis from hanging up on the bone before it passes through the posterolateral femoral cortex. Once implanted, the tip 125 can be pulled off of the prosthesis 1" as shown in FIG. 18P. The prosthesis 7" is checked to make certain that the collar 7" is fully seated on the seat of the femur neck N, and checked for the appropriate amount of stem protrusion from the femur.

FIGS. 19A–19D illustrate an additional step which may be performed to make absolutely certain that the a collar 7''' of a prosthesis 1''' of still another embodiment has seated fully against the femoral neck N. The prosthesis 1''' differs from the prosthesis 1" only in that the underside 11A''' of its flange 11''' is composed of two intersecting planes. The underside 11A" of the prothesis flange 11" has the shape of a conical section. A saw template, generally indicated at 127, includes a cap 128 capable of fitting on the neck 5''' of the prosthesis 1'''. The cap 128 precisely locates slots 129 just under the collar 7''' and to the medial side of the flange 11'''.

A saw (e.g., oscillating saw SW) may then be used to cut away additional portions of the femoral neck N under the collar 7'''. The saw template 127 guides the saw SW and a reciprocating saw (not shown) for making cuts which are closely congruent with the shape of the underside (9A''', 11A''') of the collar 7'''. The planer shape of the underside 11A''' permits linear cuts to be made (e.g., as by the blade B' of the reciprocating saw in FIG. 19D) adjacent to the flange while achieving a high degree of congruency between the cut surface and the flange underside. After removal of these portions, the underside of the collar 7" is irrigated of remaining debris and the area is checked for completeness of the removal. The prosthesis 1''' is then driven downwardly (e.g., 1 or 2 mm) after the portions are removed for a more congruent seating against the neck N.

Figure 19D:
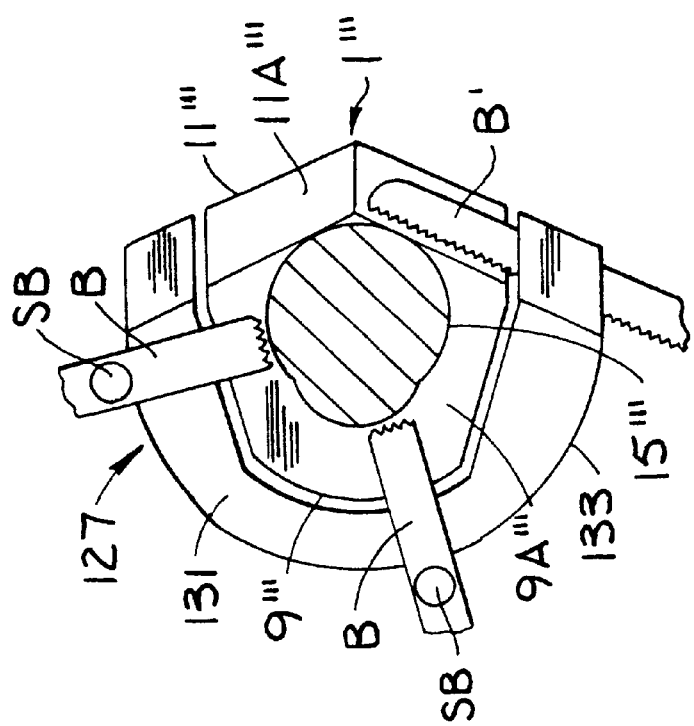
FIG. 19D is a section taken in a plane including line 19D—19D of FIG. 19A.
Figure 19C:
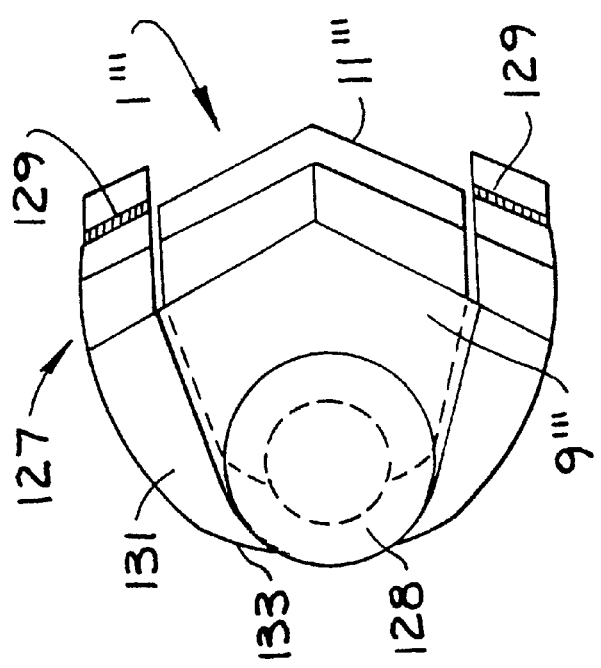
FIG. 19C is a top plan view of the femur and saw template.
Figure 20:
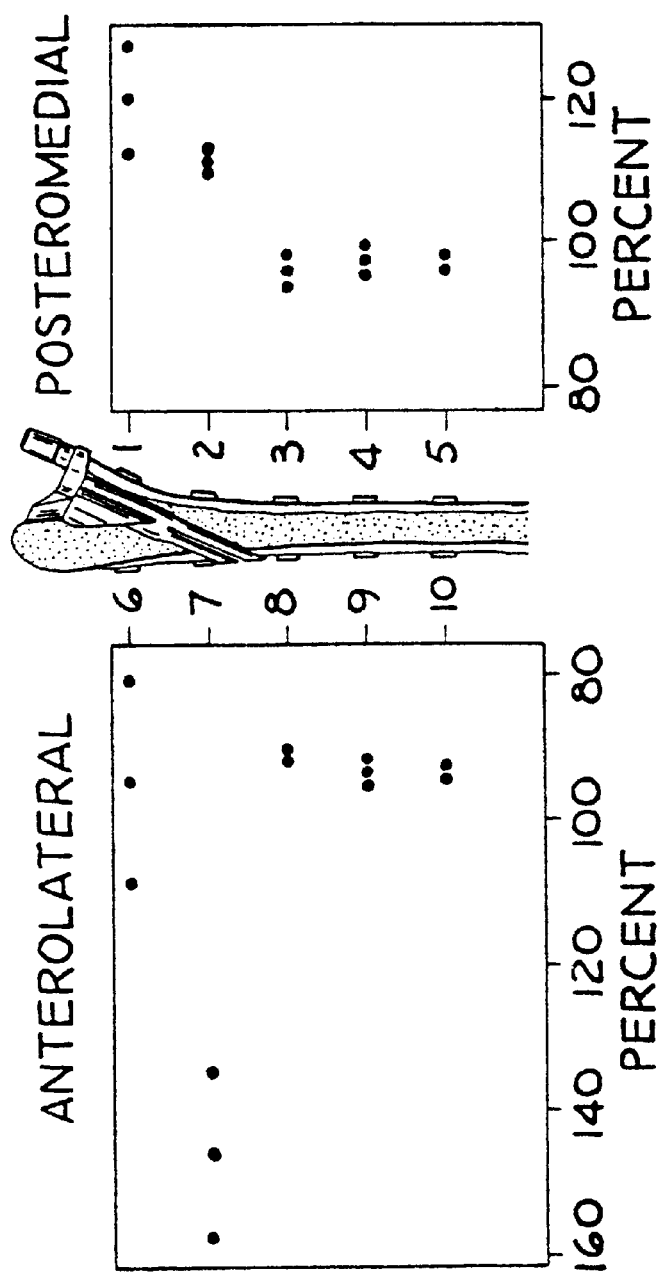
FIG. 20 is a plot of test results on the prosthesis of the present invention.

The slots 129 are disposed in a rim 131 of the saw template 127. Referring to FIG. 19D, the rim 131 has a peripheral edge 133 which is shaped so that the distance of the edge to the upper portion 15''' of the stem 13''' of the prosthesis 1''' is everywhere constant. The peripheral edge 133 is engaged by stop bolts SB on blades B of the saw SW to limit the inward travel of the saw blade. Thus, the shape of the rim 131 assures that the blades B of the saw SW will not contact the upper portion 15''' of the stem 13'''.

It is envisioned that the saw template 127 could be used in place of the planing guide (75, 75') and calcar planer (81, 81'). The other steps for implantation of the prosthesis 1''' would be the same as shown in described above for the lesser preferred, more preferred and most preferred methods. However, there is no planing of the neck N after the femoral head H is resected to form a seat for the collar 7'''. The prosthesis 1''' is driven into the femur F until the underside (9A''', 11A''') of the collar 7''' engages the neck. The saw template 127 is attached to the prosthesis 1''' and the bone is cut under the collar 7''' to form the seat for the collar. The saw template 127 may also be used beneficially in the removal of a previously implanted prosthesis 1'''. Bone ingrowth into the prosthesis 1''' is promoted (as described above) only on the underside (9A''', 1A''') of the collar 7'''. Minimal amounts of bone would be removed using the saw template 127 to separate the underside (9A''', 11A''') of the collar 7''' from the femur F.

(d) Study Regarding Present Invention

In total hip arthroplasty (THA), intramedullary stem femoral components decrease strain levels in the proximal femur resulting in periprosthetic bone loss. This study evaluates the strain pattern of the femoral stem design of the present invention in comparison to a normal femur and to conventional femur head-neck prostheses.

Attempts to eliminate strain deprivation bone loss in THA by means of reduced stiffness intramedullary stems have been unsuccessful(1). A human study of an instrumented femoral prosthesis found the load trajectory of the hip to fall within a relatively narrow range of angles(2). An alternative approach to improve proximal femoral loading is to align the femoral stem parallel to the average resultant loading vector of the individual hip. In theory, unimpeded loading of the femoral neck through a stable interface should generate strain levels equivalent to the intact femur. To enable unrestricted collar-neck loading, it is necessary for the implant stem to go through the bone in line with the resultant vector. The purpose of this study was to determine the strain distribution of a transosseous THA prosthesis.

Twelve synthetic femurs were bonded with twelve triaxial rosette strain gages (e.g., strain gages 109 shown in FIG. 1), five each along the posteromedial and anterolateral aspect and one each proximal-anterior and proximal posterior. The femurs were mounted in a single limb stance jig. Spinal loads of 1068 and 2135 Newtons were applied with simulated abductor force of 712 and 1423 Newtons creating a resultant 21° from the femoral shaft axis. Strain data were acquired with a computerized multi-channel system which converted the readings to microstrain.

Prototype cobalt-chrome transosseous femoral stems constructed according to the principles of the present invention were installed and loaded under the same conditions as the intact femurs. The collar was 10° conical and perpendicular to the stem. The proximal stem consisted of two cylindrical elements 23, 25 of 15 and 21 mm diameter, respectively, and achieved tangential contact with the endosteal cortex. The distal stem, which was fluted and 12 mm in diameter, was press-fit through an 11.5 mm hole in the posterolateral cortex. Two distal stem variations were tested in each femur: slotted (n=11) and solid (n=12). Radiographs of each femur were obtained. The angle of implantation varied from 146° to 158° in relation to the lateral shaft cortex.

Eight non-cemented and cemented cobalt-chrome intramedullary stems (Replica, 16.5-LG and Response, 13.5, manufactured by DePuy, Inc. of Warsaw, Ind.) were installed and tested. Analysis of variance was performed on all data.

Comparable strain patterns were noted at each of the two loading conditions. The following results are from the higher load condition. A graphic representation of the results appears as FIG. 18.

The non-cemented and cemented intramedullary stems resulted in proximal posteromedial compression strain levels of 42.7±4.6% (mean±SEM, p=0.0007) and 32.3±2.6% (p=0.0001) compared with the intact condition.

The slotted and solid transosseous stems produced proximal posteromedial compression strain levels of 119.0±7.4% (p=0.36) and 101.1±16.6% (p=0.66). Compression, tension and shear strain levels were generally not significantly different from intact levels. Exceptions included increased tension strain at the most proximal posteromedial gage with the slotted stem, 128.9±2.7% (p=0.029). Significantly increased compression strain was noted at the gage nearest the stem exit site with the slotted and solid stems (146.1±11.2%, p=0.0096 and 188.6±11.9%, p=0.0006). A trend was noted of higher proximal strain levels with a more horizontal angle of implantation, however this was not significant on linear regression analysis.

The diminished strain levels noted with the intramedullary stem femoral components were consistent with those previously reported(3). Although significant effort has been expended attempting to resolve the "modulus mismatch" of intramedullary stems, the results of this study suggest that a trajectory mismatch may be a more significant factor in strain reduction. The compression trabeculae of the hip were found to be 10 to 40° more horizontal than the axis of the femoral shaft(4). The consequent bending moment on intramedullary stem components impedes proximal interface loading. The loading trajectory of the hip is more horizontal than intramedullary stem insertion trajectory (femoral shaft axis) which creates a bending moment.

A trajectory matched femoral component (stem aligned with loading vector) incurs a smaller bending moment and receives a more axial load transmission. The cylindrical machining and corresponding stem of this transosseous design seeks to resist rotation and toggle with proximal and distal cortical contact/macrointerlock, but accommodates collar-neck interface compression. Although proximal femoral strain levels were restored with this prototype, high strain levels near the distal stem would raise concern for potential thigh pain.

Within a synthetic femur strain model, transosseous THA femoral components demonstrated higher proximal femoral strain levels than intramedullary stems.

(e) Embodiments for Reducing Fluid Pressure

Generally, fluid is produced by the joint lining, or synovium, for lubricating the joint. After implantation of a prosthesis, pressure in the joint created by walking or other activity may force the synovial fluid into the implant-bone interface IB. The unnatural presence of this fluid in the interface can cause high fluid pressure resulting in damage to the bone, as described above. Additionally, the presence of joint wear debris, which is carried by the fluid, in the joint space JS and in the implant-bone interface causes damage to the bone. The fluid and joint wear debris is believed to be satisfactorily vented by a bone prosthesis of a fourth embodiment (indicated generally at 401 and shown in FIGS. 21–25). As will be further described, fluid and debris entering into the interface adjacent the upper portion 415 of the stem 413 is forced by the fluid pressure to enter an opening 430 in the periphery of the upper portion, flow through a secondary channel 435 and a primary channel 414 of the stem and exit at an aperture 418 in the stem tip external to the bone. The vastus lateralis VL (muscle tissue) on the outside of the bone absorbs the fluid and wear debris because of the relatively good blood supply in the muscle, as compared to the bone. Joint fluid pressure is thereby reduced at the implant-bone interface IB and osteolysis is inhibited.

Figure 21:
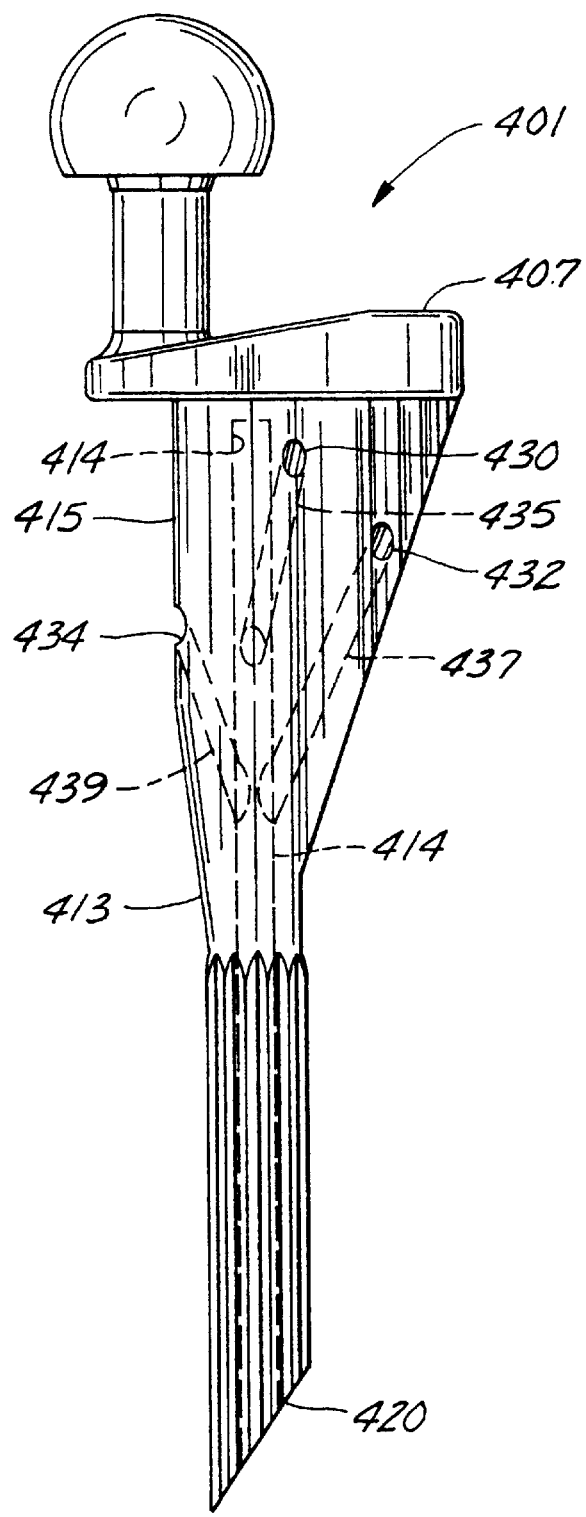
FIG. 21 is a front elevation of a prosthesis of a fourth embodiment.
Figure 22:
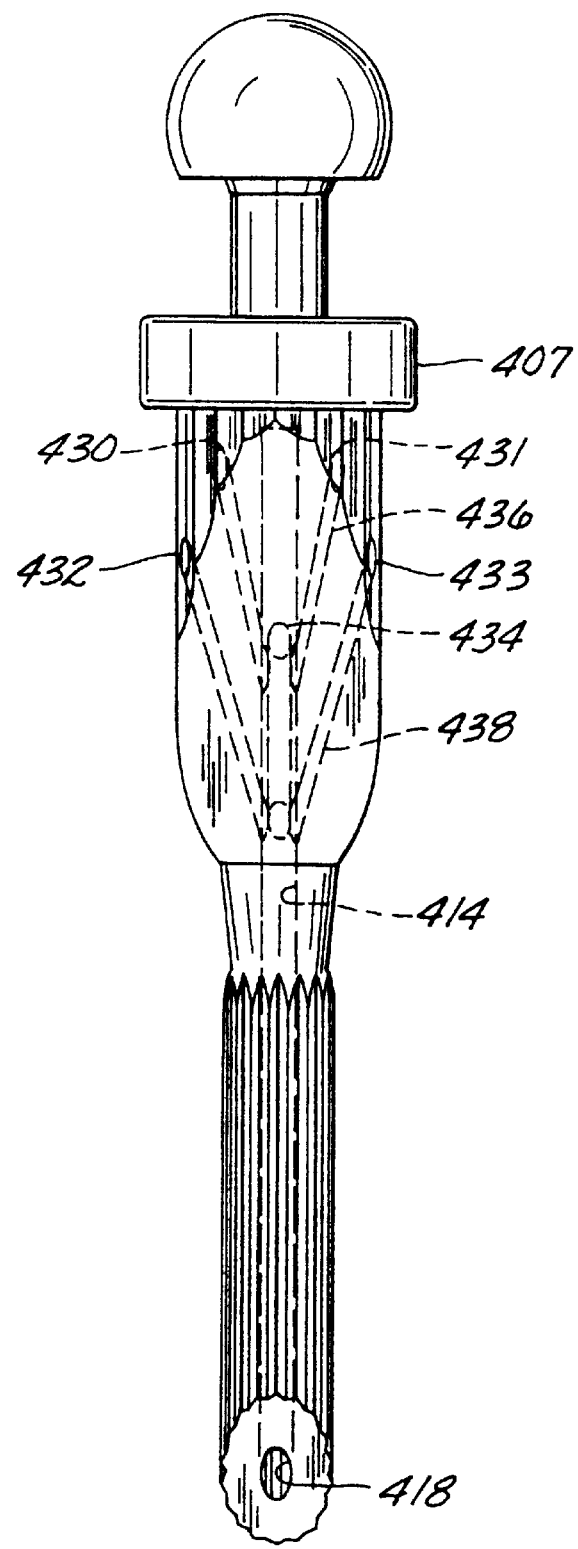
FIG. 22 is a right side elevation thereof.
Figure 23:
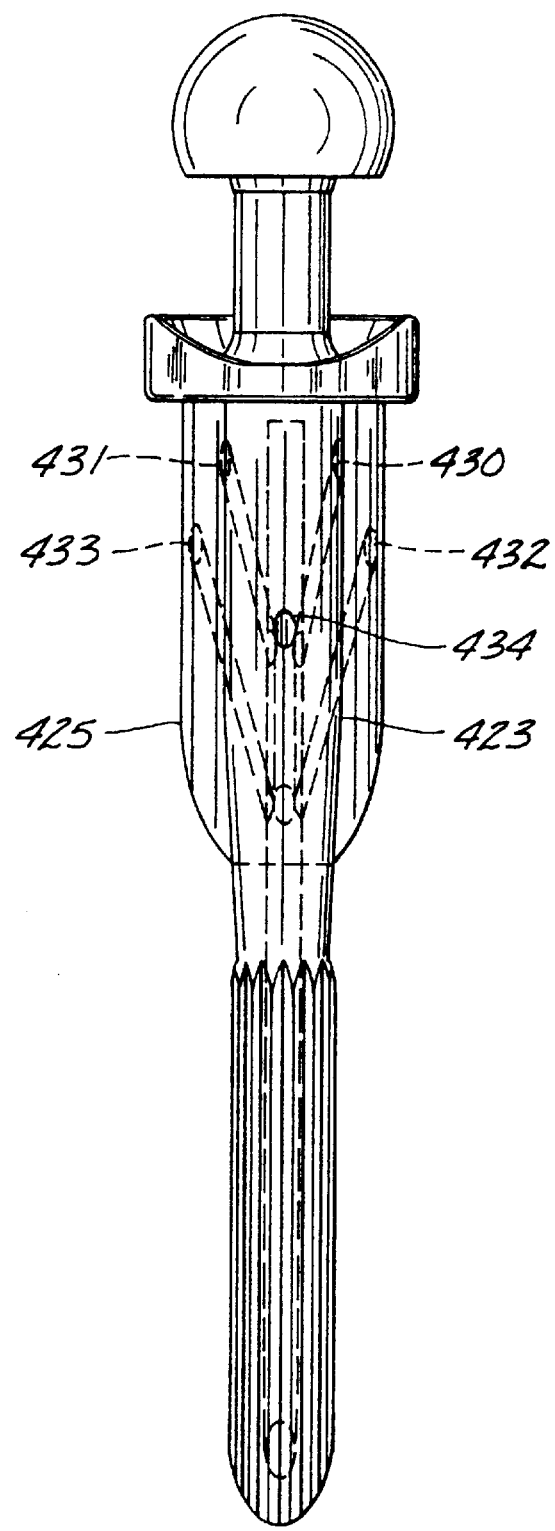
FIG. 23 is a left side elevation thereof.
Figure 24:
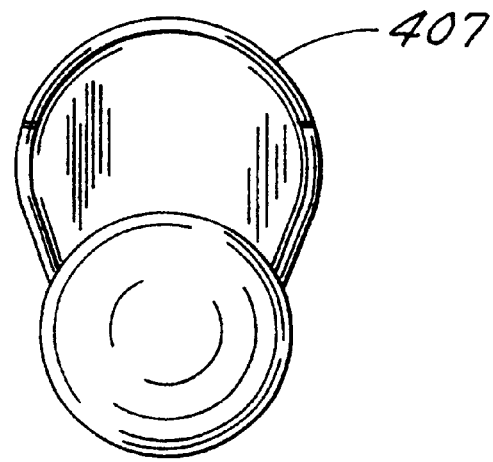
FIG. 24 is a top plan view of the prosthesis of the fourth embodiment.
Figure 25:
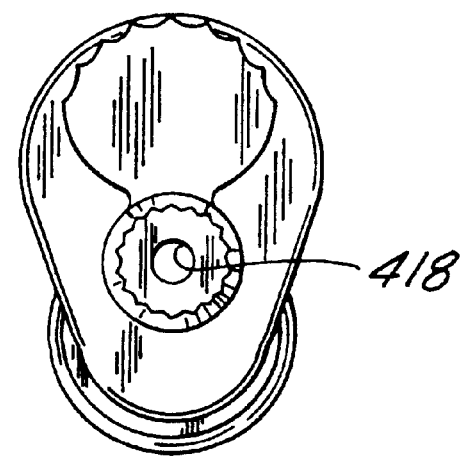
FIG. 25 is a bottom plan view thereof.

The prosthesis 401 of this fourth embodiment is generally constructed as described with reference to prosthesis 1' shown in FIG. 6. Referring to FIGS. 21–23, the stem 413 further includes a central longitudinal bore or primary channel 414 for venting fluid pressure from generally adjacent the upper portion 415 of the stem 413 to an area external to the femur F. The primary channel extends from near the top of the stem 413 to the aperture 418 in the stem tip 420 which is positioned external to the bone when the prosthesis is implanted. Fluid entering the primary channel 414 thereby exits the aperture 418 external to the bone. Preferably, the primary channel 414 does not extend through the collar 407 in this embodiment.

Preferably, the upper portion 415 includes multiple openings 430–434 and secondary channels 435–439 through which fluid flows to the primary channel. The primary channel 414 and the secondary channels 435–439 are collectively considered to be a "passageway". Multiple openings are preferred to effectively vent the fluid surrounding the upper portion. However, the number of openings should not be so great as to weaken the stem. The upper portion 415 of the stem 413 also includes splines 440 extending longitudinally along its periphery. In this embodiment, five secondary channels and openings are shown but it is within the scope of the invention to include any number of secondary channels, including only one. Each secondary channel 435–439 extends from the primary channel to its associated opening 430–434 in the periphery of the upper portion 415. The openings 430–434 are positioned at various elevations on the upper portion 415 and are staggered circumferentially around the upper portion so that fluid surrounding the upper portion is effectively vented. The openings 432, 433 are preferably positioned at the lateral side of the implant and in a groove between adjacent splines, openings 430, 431 are positioned at opposite sides of the stem 413 at the intersection of the overlapping cylindrical elements 423, 425. It is noted that the openings are not positioned immediately adjacent the collar 407 so that the hard layer of cortical bone C adjacent the undersurface of the collar does not grow into the openings. Another opening 434 is positioned at the medial side of the implant at a lower elevation on the stem than openings 432 and 433. All of the openings 430–434 and secondary channels 435–439 are drilled at oblique angles to the outer periphery of the stem. The angles are chosen to prevent bone from growing into the openings and causing axial fixation of the prosthesis 401 after implantation in the femur. As discussed above, such axial fixation is undesirable. It is believed that this configuration will relieve any high fluid pressures encountered in the implant-bone interface IB.

Figure 26:
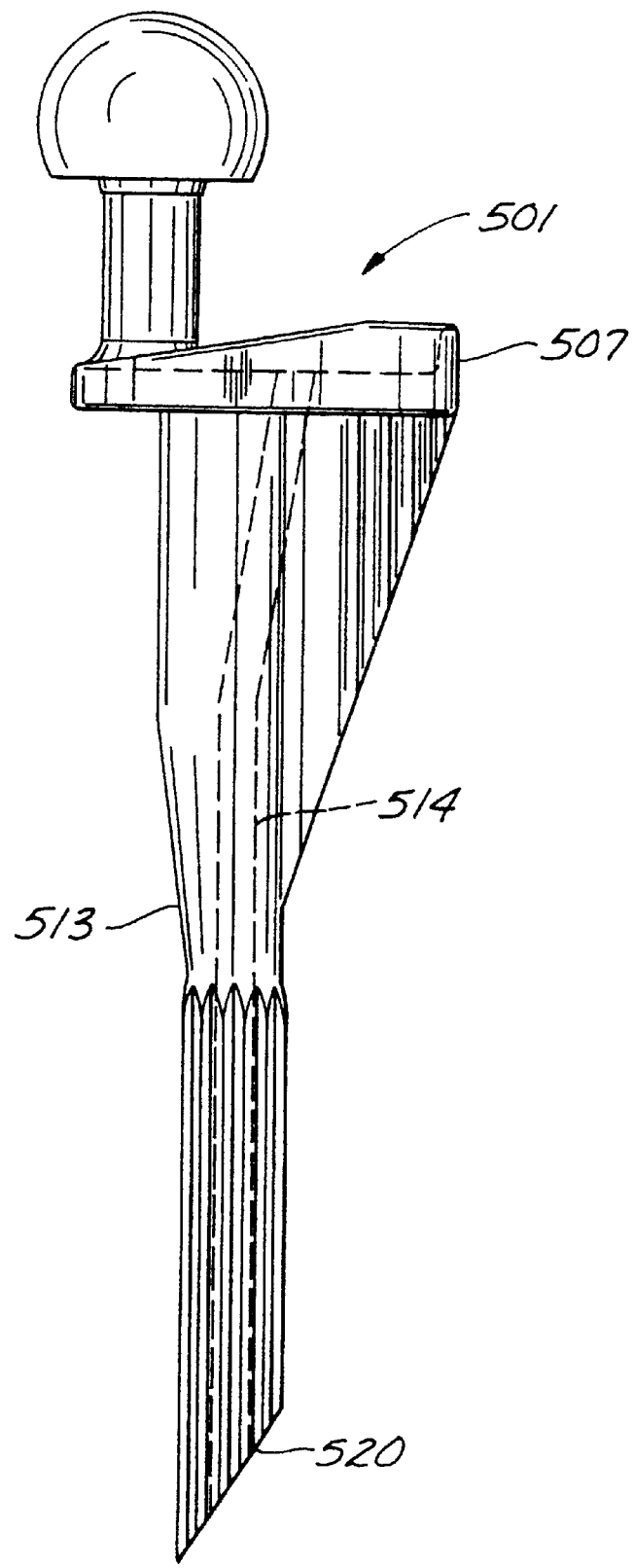
FIG. 26 is a front elevation of a prosthesis of a fifth embodiment.
Figure 27:
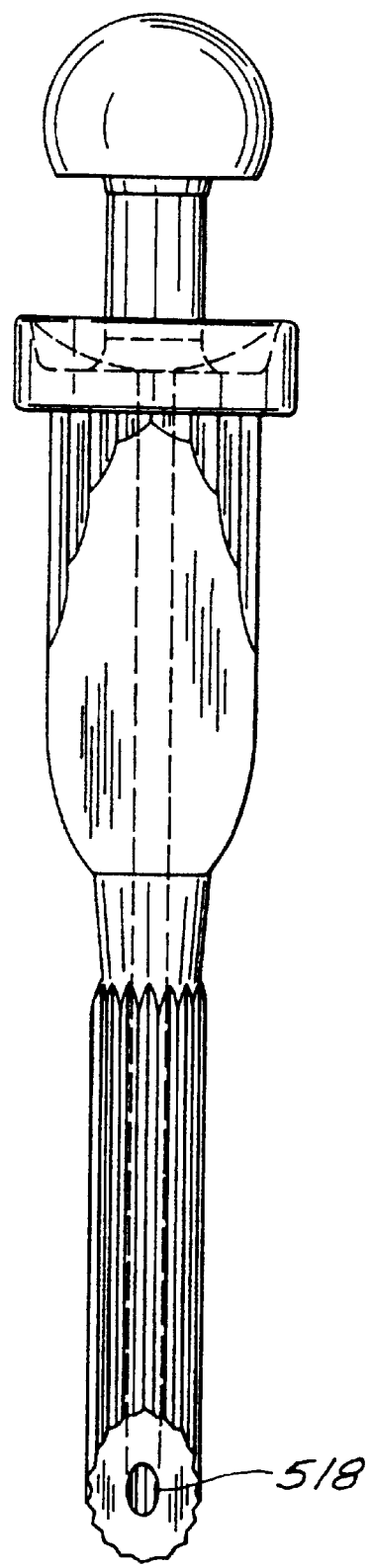
FIG. 27 is a right side elevation thereof.
Figure 28:
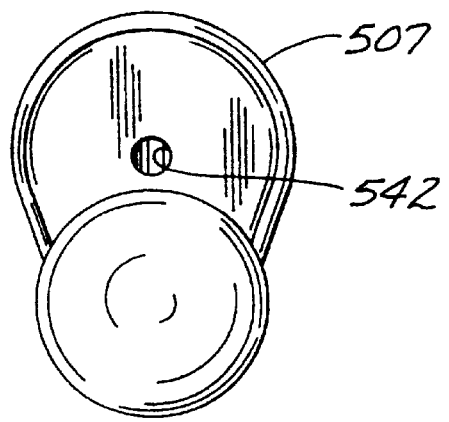
FIG. 28 is a top plan view thereof.

Referring to FIGS. 26–28, a prosthesis 501 of a fifth embodiment has a primary channel 514 extending from an opening 542 in the upper side of the collar 507 through the collar and downward the length of the stem 513 to an aperture 518 in the stem tip 520 positioned external to the femur as implanted. The primary channel 514 may include an angle as shown in FIG. 26. The primary channel 514 is effective to vent fluid pressure from the joint space JS above the collar 507 to an area adjacent the stem tip 520 which is external to the femur, thereby relieving joint fluid pressure in the joint space. This may inhibit the occurrence of acetabular osteolysis.

Figure 31:
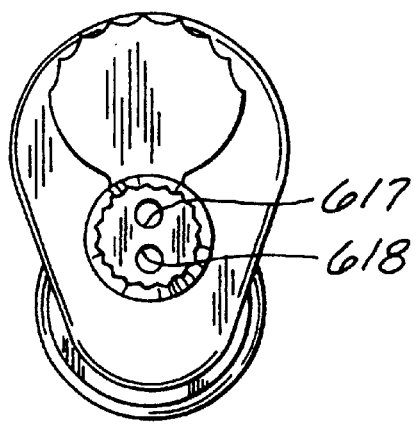
FIG. 31 is a bottom plan view of the prosthesis of the sixth embodiment.
Figure 29:
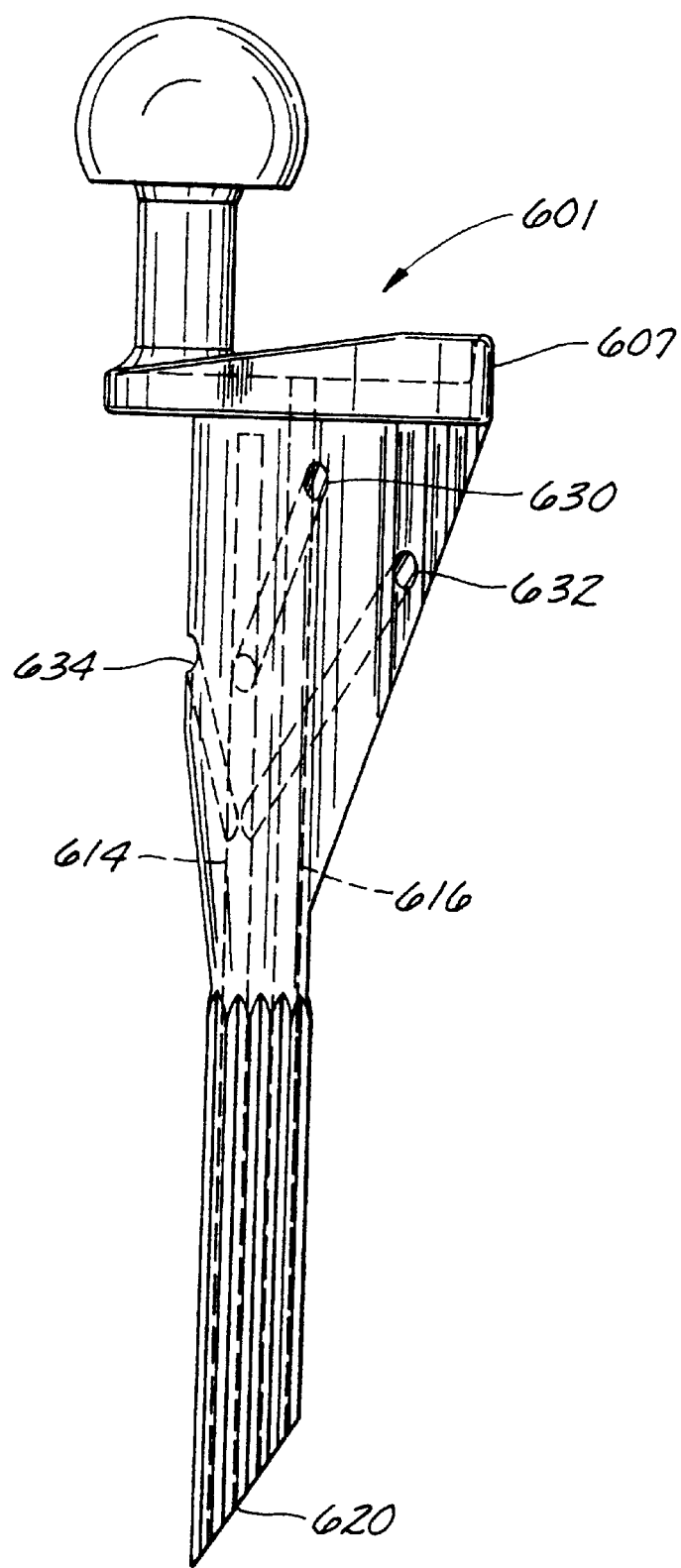
FIG. 29 is a front elevation of a prosthesis of a sixth embodiment.
Figure 30:
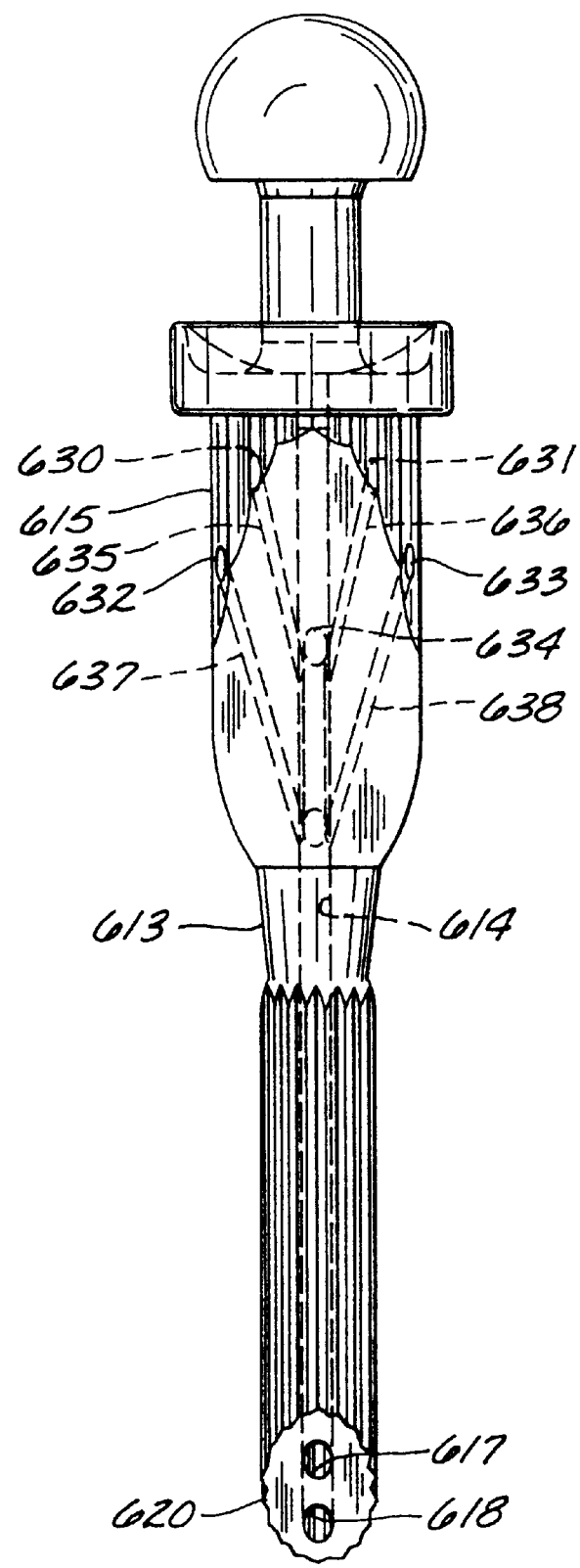
FIG. 30 is a right side elevation thereof.

Referring to FIGS. 29–31, a prosthesis 601 of a sixth embodiment includes the features of the fourth and fifth embodiments in a single prosthesis. That is, the prosthesis 601 includes openings 630–634 in the periphery of the upper portion 615 of the stem 613 and associated secondary channels 635–639 which are connected to a first primary channel 614 and first aperture 618 at the stem tip 620 for venting the implant-bone interface IB at the upper portion. The prosthesis 601 further includes a second primary channel 616 extending from the upper side of the collar 607 and downward through the stem 613 to a second aperture 617 at the stem tip 620 to vent the joint space JS above the collar. In this embodiment, the second primary channel 616 is not connected to the first primary channel 614 or to the secondary channels so that the fluids vented from the upper side of the collar 607 cannot enter the secondary channels 635–639 and exit at the upper stem. Likewise, the fluids vented from adjacent the upper portion of the stem 613 cannot enter the second primary channel and exit at the upper side of the collar.

Figure 32:
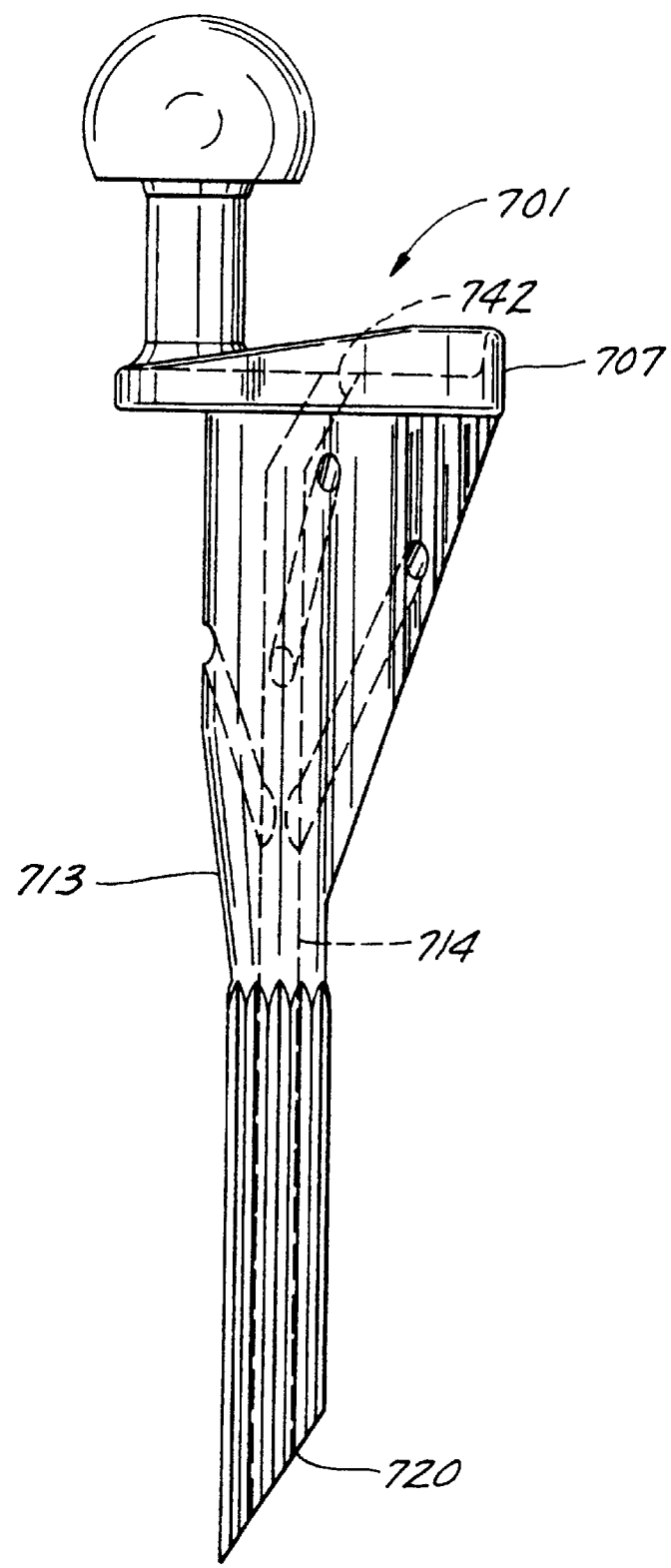
FIG. 32 is a front elevation of a prosthesis of a seventh embodiment.
Figure 33:
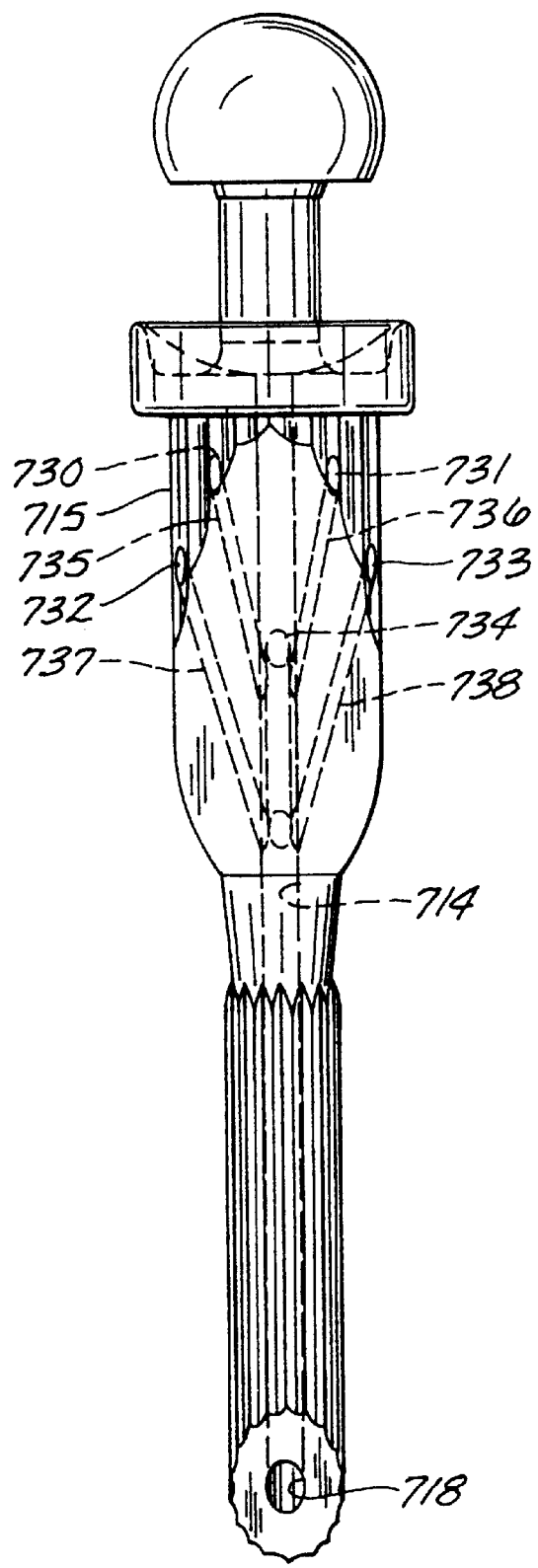
FIG. 33 is a right side elevation thereof.
Figure 34:
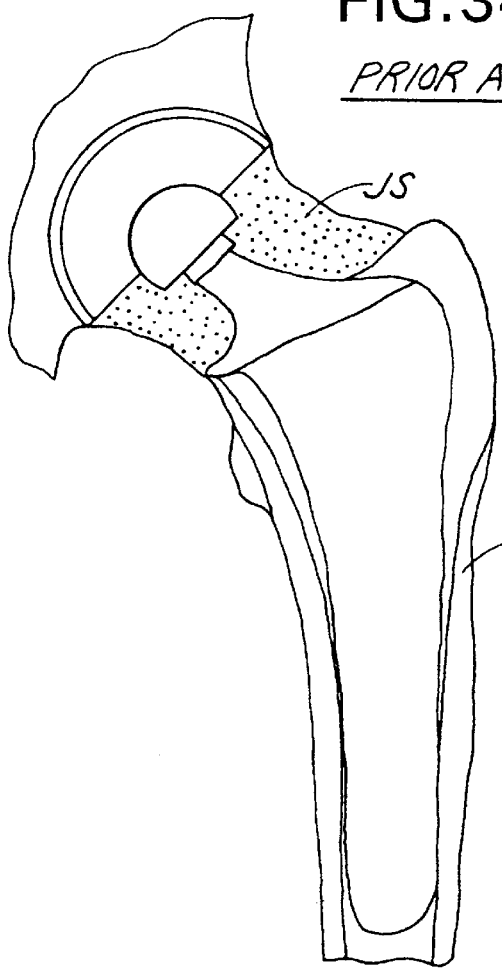
FIG. 34 is a schematic, fragmentary cross section of an upper femur showing a prior art femoral head-neck prosthesis implanted in the femur (the prosthesis being shown in full lines)

Referring to FIGS. 32–33, a prosthesis 701 of a seventh embodiment includes the features of the sixth embodiment, except that only one primary channel 714 is included to vent both the implant-bone interface IB and the joint space JS upward of the collar 707. The primary channel 714 extends from an opening 742 (see FIG. 28) in the upper side of the collar 707 and down through the stem 713 to an aperture 718 at the stem tip 720. As in the fourth embodiment the secondary channels 735–739 connect to the primary channel 714. As is apparent, in this seventh embodiment the fluids vented from the implant-bone interface IB and from the joint space JS will be intermixed in the primary channel 714 before being vented at the aperture.

The method of implanting the prosthesis of the fourth through seventh embodiments is the same as the method disclosed above. Preferably, the guide tip 125 is mounted at the tip of the stem when the prosthesis is inserted, as discussed above with respect to FIG. 18N. The guide tip prevents the aperture at the stem tip from becoming occluded as the prosthesis is inserted in the femur. As described above, the guide tip is removed after the prosthesis is inserted.

It is to be understood that the prosthesis of the present invention may be other than a femoral prosthesis. That is, the invention of the fourth through seventh embodiments is directed to venting fluid pressure adjacent a bone prosthesis to relieve fluid pressure and is not limited to femoral prostheses.

Figure 35:
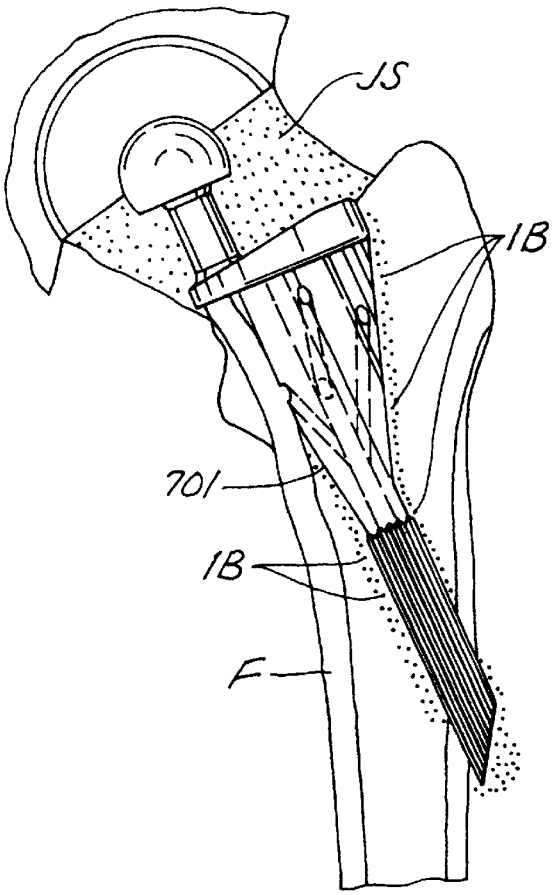
FIG. 35 is a schematic, fragmentary cross section of an upper femur showing a femoral head-neck prosthesis of the present invention implanted in the femur (the prosthesis being shown in full lines)

(f) Embodiment for Diagnosing and Treating Ailments Associated with the Prosthesis The structure of the prostheses of the fourth through seventh embodiments facilitates improved diagnosis and treatment methods without removal of the prosthesis. In particular, these embodiments permit improved diagnosis and treatment of infections which may occur at the joint around the implant. The present invention enables improved diagnosis by allowing a needle, brush, probe or other instrument to be inserted into the primary channel 714 and into the joint space JS. Improved treatment of the infection is accomplished primarily by introducing medication, such as an antibiotic solution, upward through the primary channel 714 and secondary channels 735–739 into the implant-bone interface IB and joint space JS (see FIG. 35). It is to be noted that this is accomplished by causing medicine to flow upward into the secondary channels and out the respective openings, in other words, the medicine flows in the reverse direction of the synovial fluid vented from the prosthesis. Hereinafter, the primary channel 714 secondary channels 735–739, joint space JS and the implant-bone interface IB will be referred to collectively as the "joint region". It is also to be noted that the term "instrument" includes needles, brushes, pins and arthroscopic probes, among others. While any of the prostheses of the fourth through seventh embodiments may be advantageously used with the methods described below, the prosthesis 701 of the seventh embodiment is illustrated and discussed. Preferably, the prosthesis 701 is modified to include internal threads in the primary channel 714 immediately adjacent the aperture 718.

In the minimally invasive method of this embodiment, the patient is first placed under general, regional (spinal or epidural) or local anesthesia. The patient is placed in the lateral decubitus position (side-lying position) with the affected hip facing upward (FIG. 36A). The skin of the thigh region TH is prepared with antiseptic solution and isolated with sterile adhesive drapes. Referring to FIG. 36B, a fluoroscope FL and monitor MO are used to view the stem 713 of the implanted prosthesis 701 and to locate the axis of the stem. The fluoroscope FL is a radiographic instrument that provides a real time X-ray image of the bone and the prosthesis 701 on a video monitor. The fluoroscope FL is well known to those in the art. The fluoroscope FL is positioned to view the femur F from the front looking toward the posterior of the femur (anteroposterior view). The femur F is internally rotated inward so that the viewing plane of the fluoroscope FL is approximately parallel to the longitudinal axis of the stem 713 and the primary channel 714 so that the stem and, importantly, the portion of the stem protruding from the femur, is seen in elevation. The femur F is held in this position while a metal rod (not shown) is placed in front of the thigh TH to locate the axis of the stem 713. The thigh TH is then palpated to determine the location of the bone and the position of the prosthesis. The location for an incision is then determined by extrapolating the intersection of the axis and the skin evidenced by the metal rod rearwardly to a position in the plane of the rod overlying the bone, and a mark is made. Alternatively, the fluoroscope may be rotated 90 degrees to determine the location of the bone and the position of the prosthesis. As a second alternative, a dual plane fluoroscope, which includes two fluoroscopes operating simultaneously, may be used to view the prosthesis and femur F in elevation and in plan to determine the axis and the position of the prosthesis. Also, the patient may be placed on a "fracture table" in the supine or lateral decubitus position. The fracture table allows improved access to the legs and permits the fluoroscope to be more easily rotated around the legs of the patient. After marking the intersection, a small (approximately one cm) incision is made in the skin at the mark.

Figure 37:
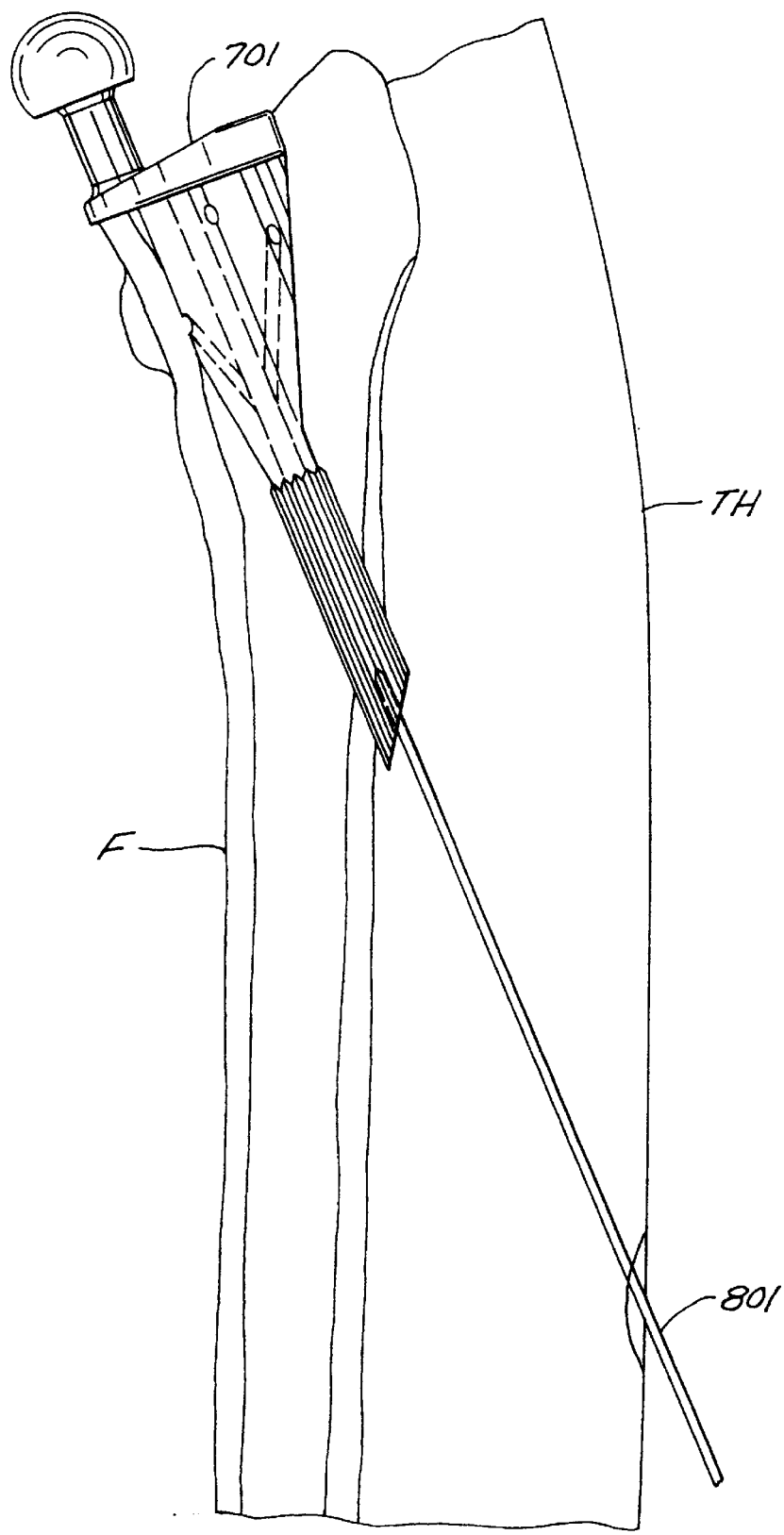
FIG. 37 is an enlarged fragmentary cross section similar to FIG. 35 illustrating insertion of a pin in the prosthesis (the single line to the right of the femur and prosthesis is intended to represent the surface of the skin of the thigh through which the pin extends)

Referring to FIG. 37, a straight elongate pin 801 is inserted in the incision and slid through the underlying tissue along the axis. The underlying tissue includes subcutaneous fat, the fascia lata FA, the vastus lateralis VL. Care must be exercised to avoid the sciatic nerve and other vital structures. The fluoroscope FL is used to visualize the pin 801 and the prosthesis 701 to help in locating the stem tip 720 and the aperture 718 of the primary channel 714 located at the stem tip. To ensure engagement of the pin 801 with the stem tip 720, the pin may be used to palpate the stem tip. Alternatively, a guide wire (not shown) may be used in place of the elongate pin 801.

Figure 38A:
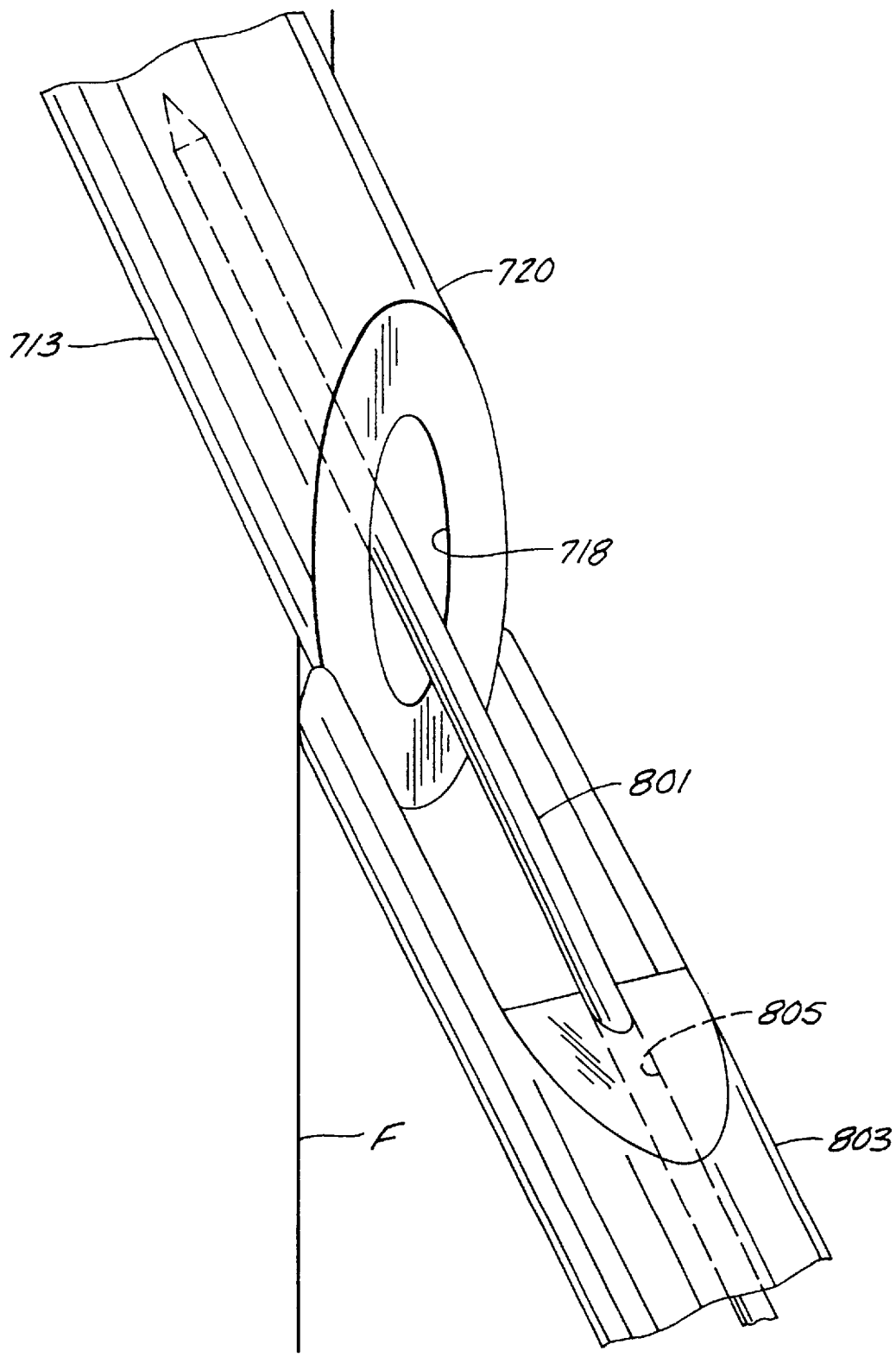
FIGS. 38A–B illustrate insertion of the pin in the prosthesis using a centering guide (the single line to the left of the centering guide is intended to represent the femur through which the prosthesis projects)
Figure 38B:
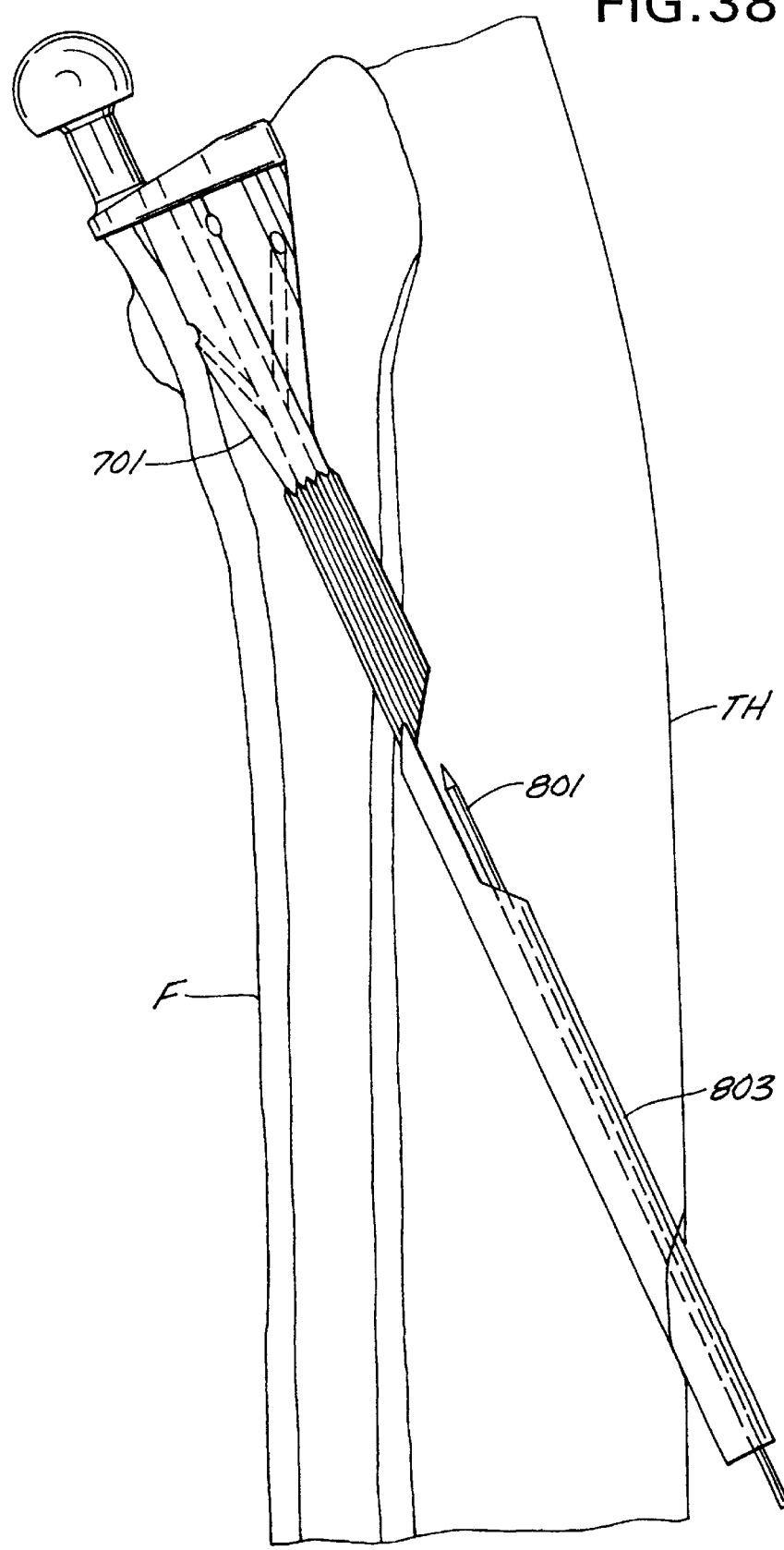

If the attempt to locate the stem tip 720 and/or place the pin 801 in the primary channel 714 is unsuccessful, a centering guide 803 may be used to help guide the pin. Referring to FIGS. 38A and 38B, the centering guide is an elongate tube having a bore 805 therethrough sized to receive the pin 801 and a trough-shaped end corresponding to a segment of the cylindrical exterior shape of the stem 713 at the tip 720. The guide may also include a second bore (not shown) for inserting a pin into the prosthesis 601 of the sixth embodiment wherein the stem 613 includes a second primary channel 616. The pin 801 is removed from the incision and then the centering guide 803 is inserted into the incision and slid through the tissue along the axis until the periphery of the stem tip 720 is partially received in the trough-shaped end of the centering guide. The bore 805 of the centering guide is thereby centered on the longitudinal axis of the primary channel 714 of the stem 713. The pin 801 is passed through the bore of the guide and is guided into the primary channel 714 of the stem 713 because the bore 805 and primary channel are substantially concentric. Once the pin 801 is inserted in the primary channel 714 of the stem 713, the centering guide 803 is removed from the incision.

Fluid is drawn from the joint region using an elongate needle and syringe (not shown). The fluid samples may be used to confirm the existence of an infection or the fluid may be removed simply to clean the joint region and prepare the site for subsequent procedures. The elongate needle is received over the pin 801 and passed into the primary channel 714 of the stem 713. The pin 801 is removed and a syringe is attached to the end of the needle outside the thigh TH to draw a vacuum through the joint region. The tip of the needle may be positioned anywhere along the length of the primary channel 714 and in the joint space JS to withdraw fluid therefrom. The tip of the needle may also be positioned immediately adjacent each of the secondary channels 735–739 to withdraw fluid from each secondary channel. It will be apparent in regard to the prosthesis 601 that a second needle (not shown) may be inserted in the second primary channel 616 to access the joint space JS. Preferably, the internal diameter of the needle is sufficiently large so that small bits of fibrous tissue may also be withdrawn through the needle. After fluid removal is complete, the syringe is removed and the pin 801 is passed through the needle into the primary channel 714 of the stem 713. The needle is removed leaving the pin 801 in the primary channel.

Figure 39:
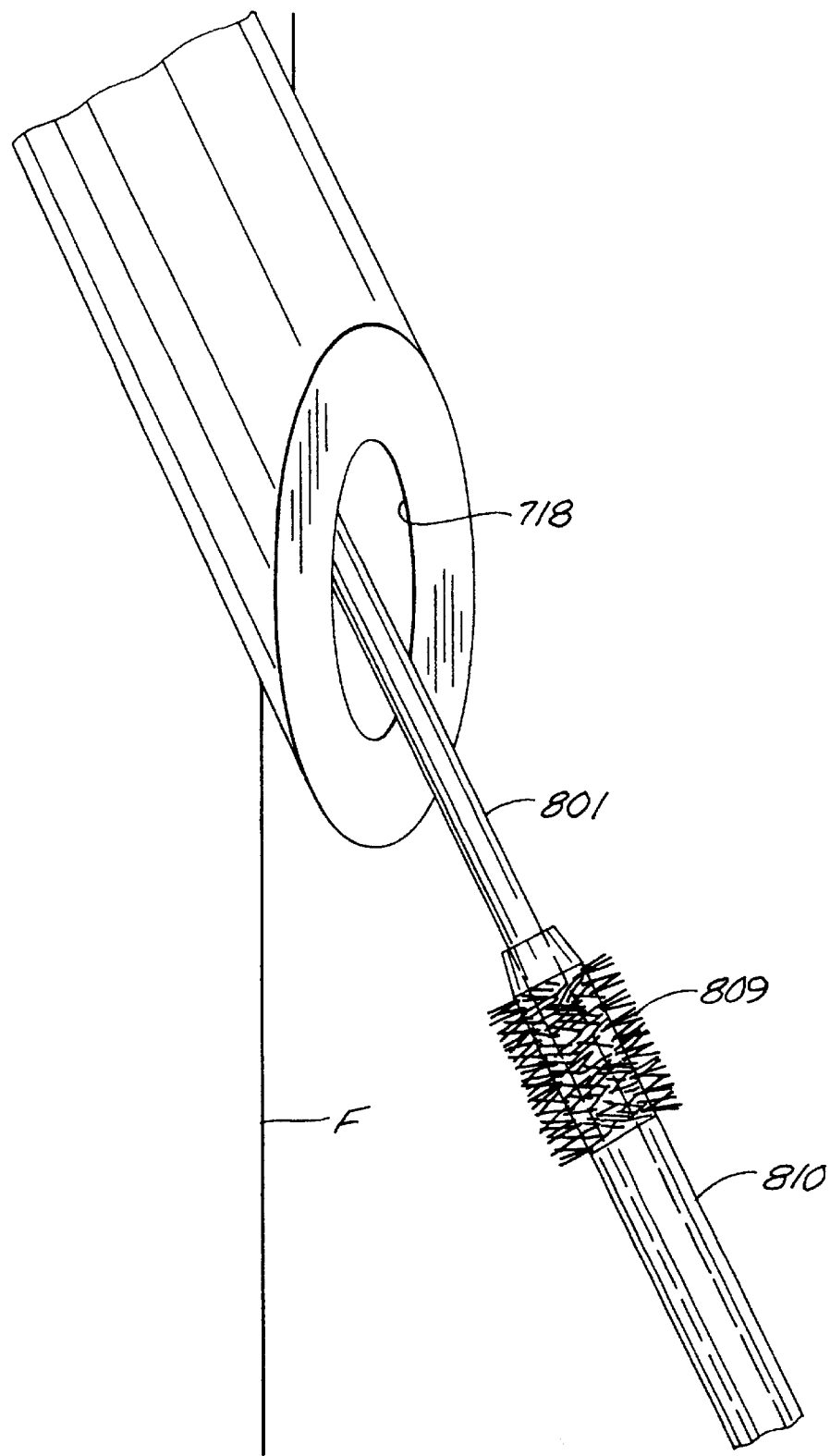
FIG. 39 is an enlarged, schematic perspective view of a cannulated brush prior to insertion in the prosthesis.

Referring to FIG. 39, a cannulated brush 809 having stiff bristles is mounted on an elongate shaft 810. The brush 809 is passed over the pin 801 and into the primary channel 714 and the joint space JS. The bristles of the brush 809 simultaneously clean the joint region and collect fibrous tissue specimens from the joint region. The brush 809 is withdrawn from the primary channel 714 of the stem 713 leaving the pin 801 in the primary channel. The tissue on the brush bristles are sent for culture of organisms and histologic examination (microscopic study). A second brush (not shown) may also be used to enter the secondary channels 735–739 for cleaning and collecting tissue samples. The second brush preferably has a smaller diameter than the cannulated brush 809 and has a bent tip so that it can enter the secondary channels 735–739.

Arthroscopic viewing of the joint space JS may be accomplished by inserting an arthroscope (not shown) through the primary channel 714 of the prosthesis 701 into the joint space JS. The arthroscope is inserted into the primary channel 714 as described above in relation to the needle. The arthroscope is connected to a digital video camera which allows viewing of the joint space JS and prosthesis 701. Such viewing enables assessment of the prosthesis 701 for stability of fixation and for wear of the joint surfaces.

Figure 40A:
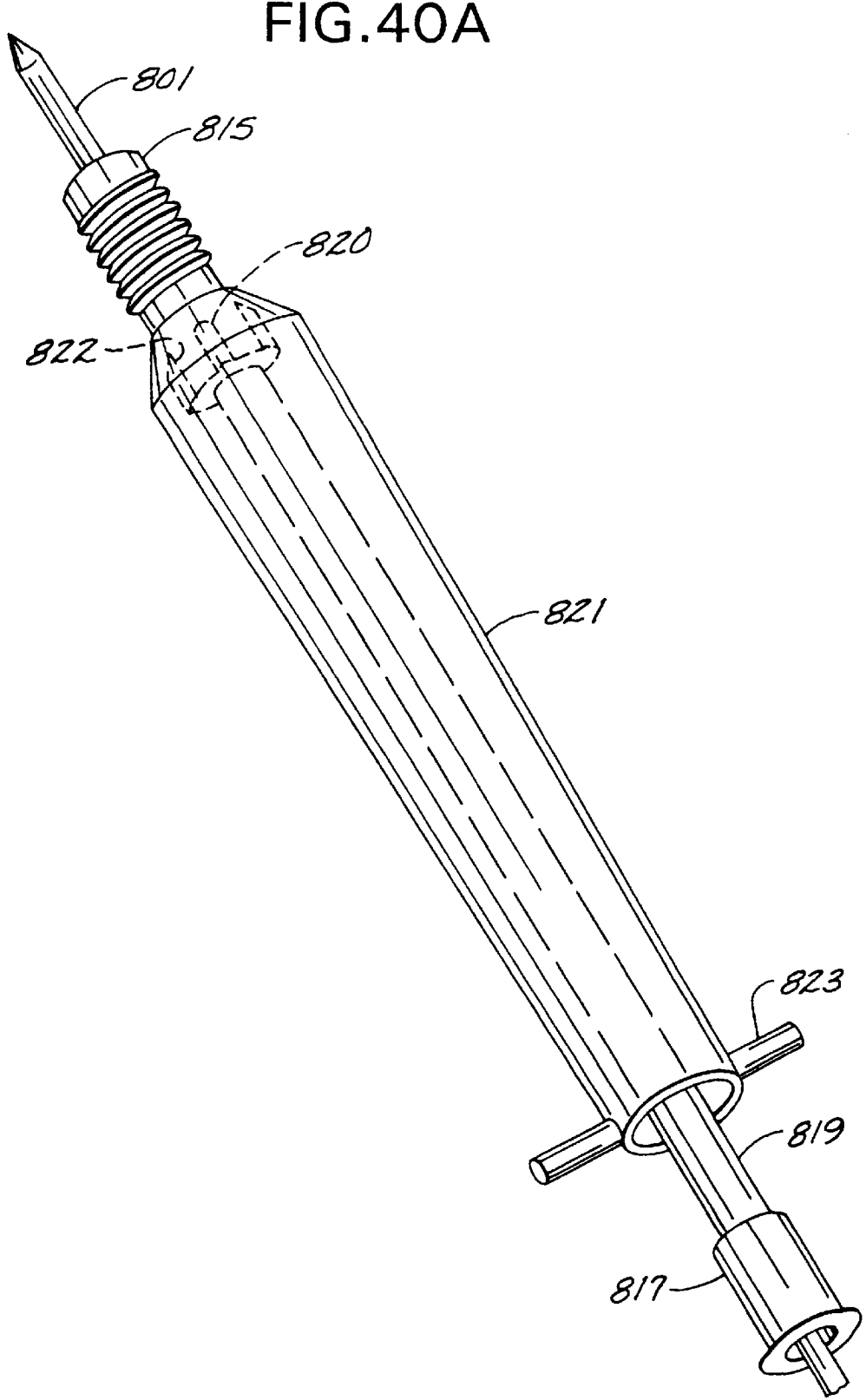
FIGS. 40A–D illustrate a method of attaching an infusion assembly to the prosthesis
Figure 40B:
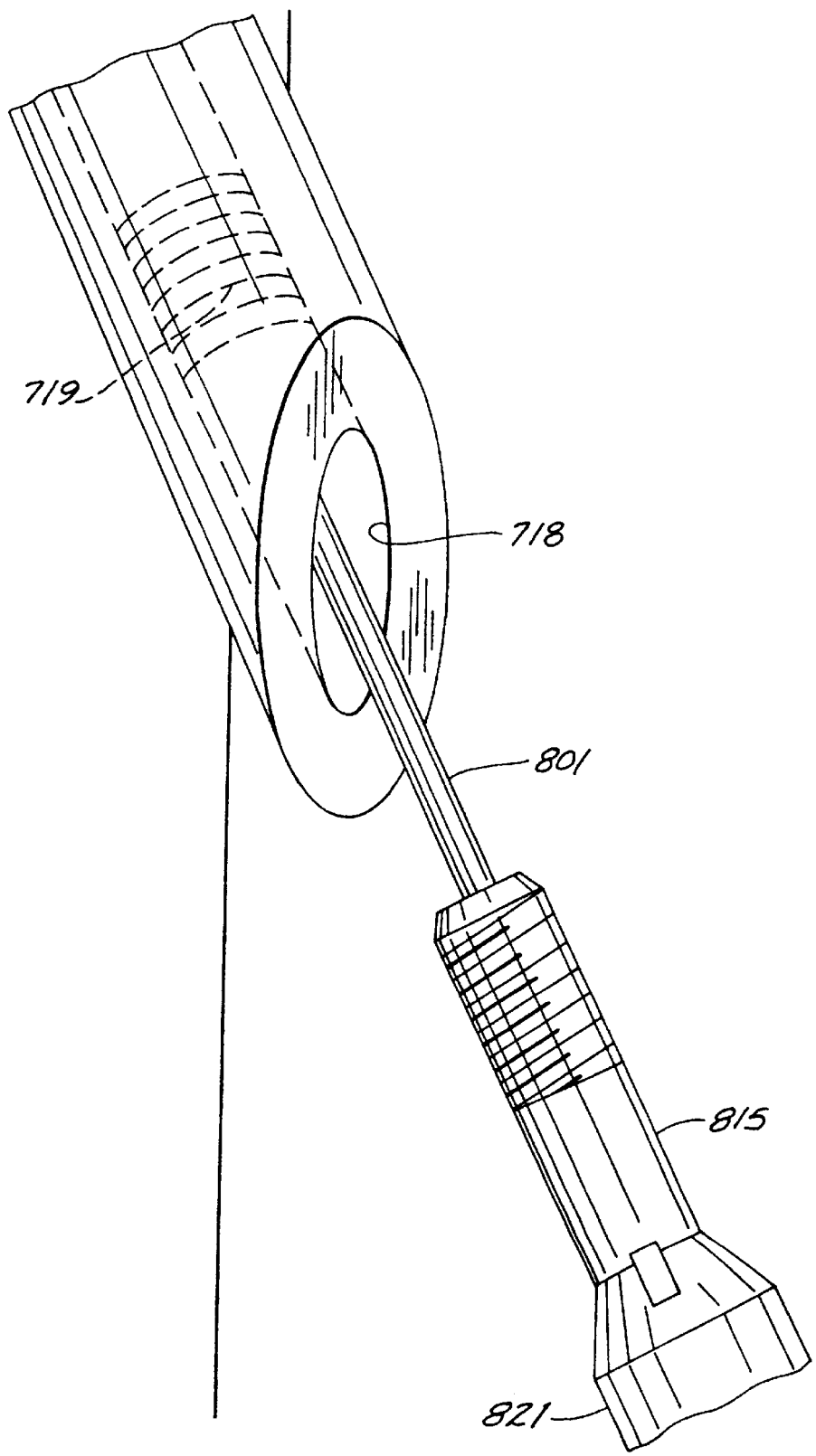

Referring to FIGS. 40A and 40B, an infusion assembly includes a threaded connector 815 (broadly, "infusion element") for insertion in the primary channel 714 of the stem tip 720, a luer connector 817 and an infusion tube 819 connecting the threaded connector to the luer connector. The threaded connector 815 is tubular, has external threads on its periphery sized to engage threads 719 in the primary channel 714 immediately adjacent the aperture 718 and fins 820 or protrusions on the periphery of an end opposite the threads. The infusion tube 819 is received at one end in the threaded connector 815 and at its opposite end in a first end of the luer connector 817. The luer connector has a "luer lock" at a second end opposite the infusion tube 819 for receiving a syringe or a second tube. An elongate, tubular wrench 821 is adapted to receive the assembly and to install the threaded connector 815 in the aperture 718. The wrench 821 has a socket 822 that receives the fins 820 of the threaded connector 815. The socket 822 has a shape corresponding to the shape of the exterior of the threaded connector 815 so that when the connector is received in the socket it is held for conjoint rotation with the wrench 821. The wrench has finger grips 823 at an end opposite the socket.

The infusion assembly is placed in the wrench 821 so that the threaded end of the threaded connector 815 protrudes from the socket 822 of the wrench and the infusion tube 819 extends through the bore of the wrench. The infusion assembly and the wrench 821 are passed over the pin 801 until the threaded connector 815 contacts the aperture 718 of the primary channel 714. The wrench 821 is turned to screw the threaded connector 815 into the threads of the primary channel 714. If difficulty is encountered in engaging the threads, the infusion assembly and wrench 821 are withdrawn from the incision. The cannulated brush 809 is passed over the pin 801 and the threads 719 of the aperture 718 are again cleaned of fibrous tissue. The wrench 821 and pin 801 are then removed leaving the infusion assembly attached to the prosthesis 701.

Figure 40C:
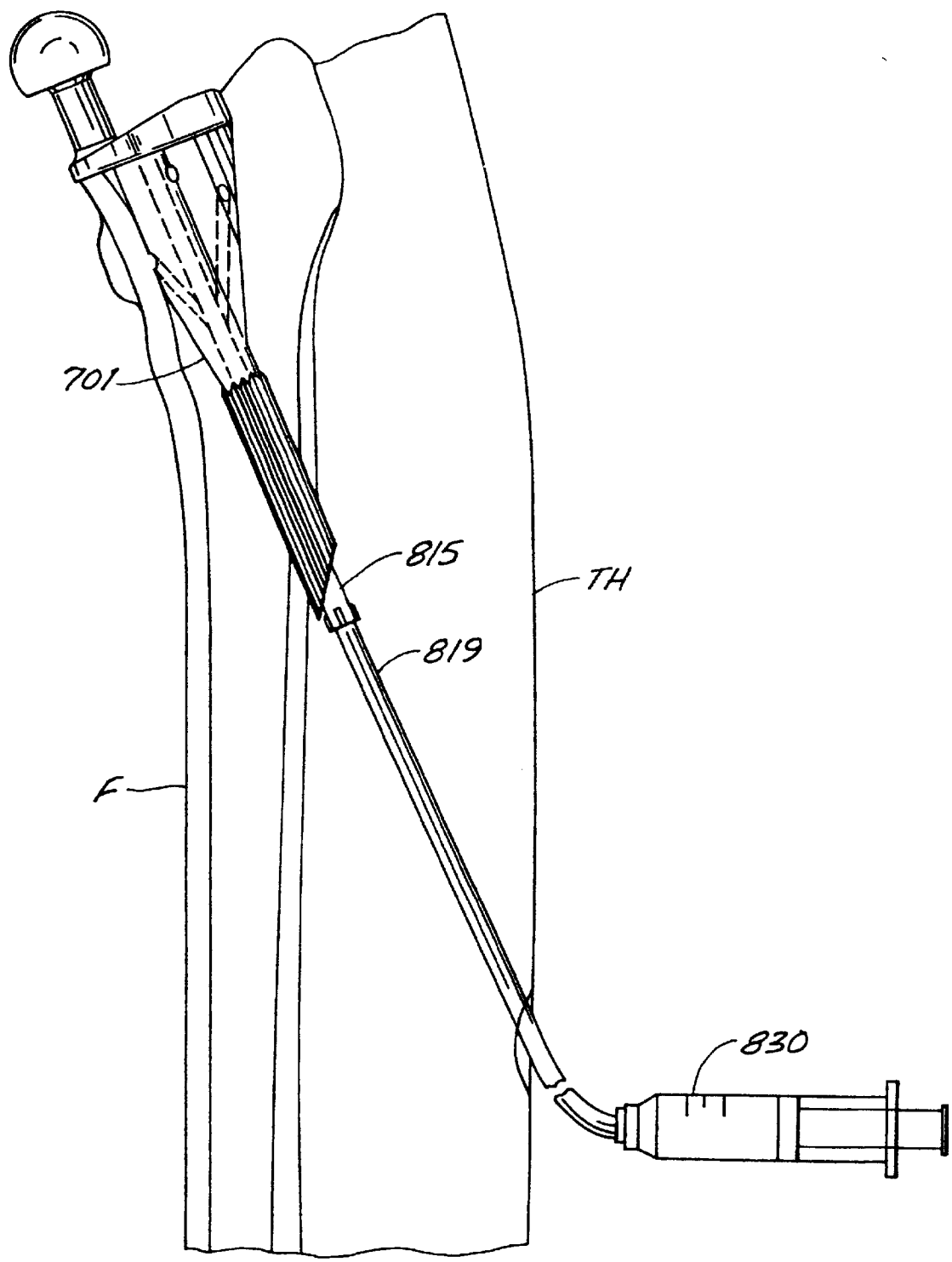

Referring to FIG. 40C, bacteria and debris in the joint region may be flushed out using the infusion assembly. A syringe 830 filled with saline or lactated Ringer's solution is attached to the luer connector 817 of the infusion assembly. The saline or Ringer's solution is infused under pressure into the infusion assembly. The solution passes through the primary channel 714 and secondary channels 735–739, exiting at the openings 742, 730–34 of the channels so that the solution washes out the implant-bone interface IB within the bone and the joint space JS above the collar, as well as the channels. The solution is thereafter withdrawn by the syringe. This process is preferably repeated several times to thoroughly wash out the prosthesis 701, implant-bone interface IB and joint space JS.

Sometimes it may be desirable to infuse a contrast medium (radiographically opaque sterile fluid, or more simply "dye") to perform an arthrogram. A syringe filled with the contrast medium is attached to the luer connector 817 and infused into the joint region. The fluoroscope FL is used to visualize the dye, which enhances radiographs and gives information regarding the relationship of the prosthesis 701 and bone. Relevant information obtained from the arthrogram in cases of infection includes the extent to which the dye pervades the joint region. The latter information gives an indication of the extent to which the antibiotic solution will infuse the joint region. Additionally, contrast medium injected through the joint region may be used to radiographically confirm that the infusion assembly is not blocked and that the connections do not leak. If a leak in the assembly is detected, the threaded connector 815 can be tightened using the wrench 821 or, if necessary, the assembly can be removed and replaced.

The contrast medium is irrigated from the joint region with saline through the infusion assembly as described above. An initial loading dose of antibiotic solution is then infused into the joint region through the infusion assembly without removal of the prosthesis. The antibiotic solution passes through the primary channel 714 and secondary channels 735–739, exiting at the openings 742, 730–34 of the channels and pervading the implant-bone interface IB within the bone and the joint space JS above the collar.

Figure 40D:
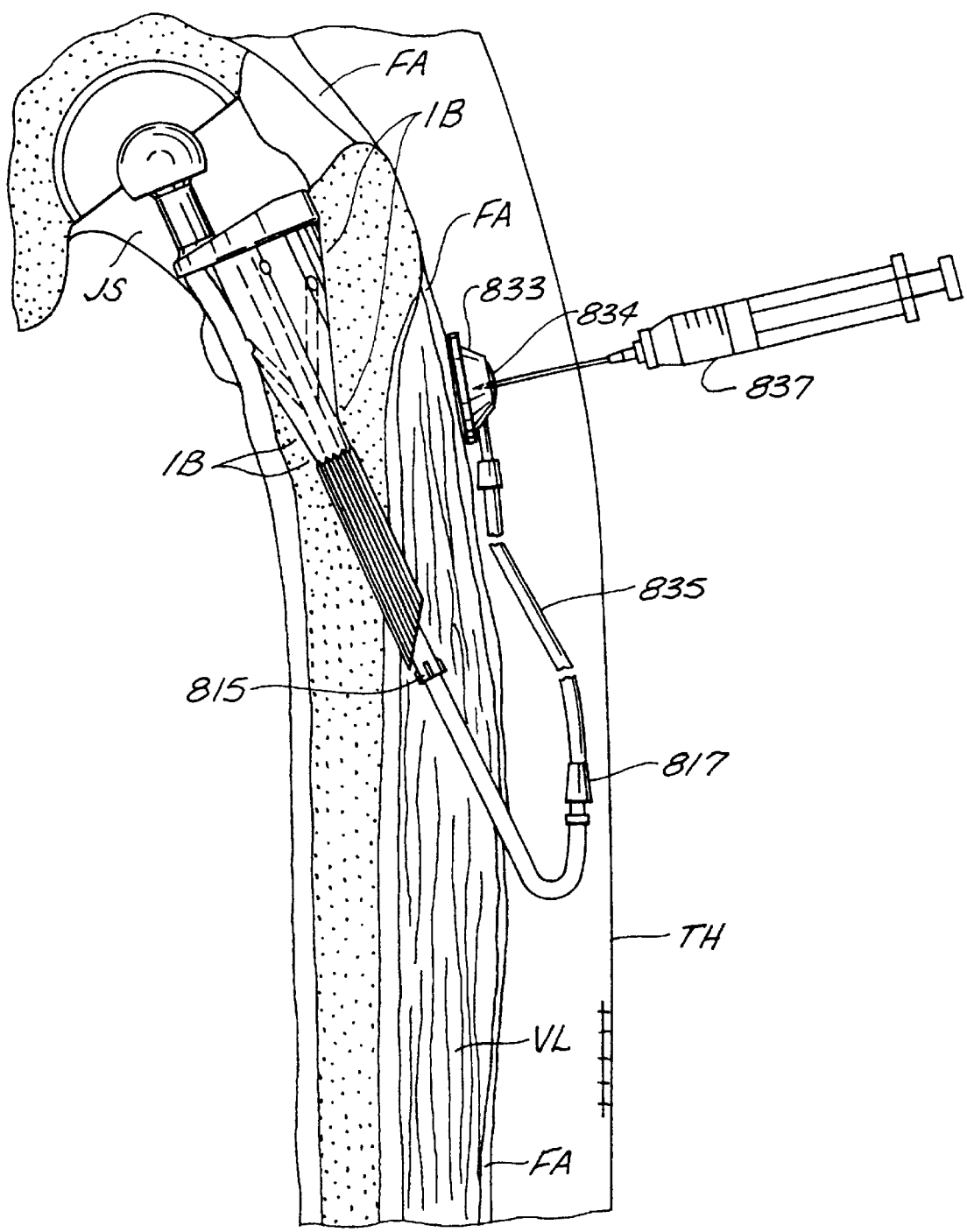

The present invention provides for repeated administration of antibiotics to the joint. Referring to FIG. 40D, an infusion port assembly includes an infusion port 833 for infusing liquid medicine into the joint region on a regular basis. The port 833 has a self-sealing membrane cover 834 penetrable by a needle for injecting the medicine. The port 833 is connected via tubing 835 to the luer connector 817 of the infusion assembly. The port 833 is placed in a location spaced from the infected area and is anchored with sutures to fascia lata FA under the skin. The infusion port 833 is located so that it is easily accessed through the skin by a hypodermic needle. The incision is then closed. The port 833 is thereafter used, typically once a day, to infuse the joint region with antibiotic solution that flows through the tubing into the joint region. The infusion assembly permits extremely high local concentrations of antibiotics directly to the joint region that should eradicate the infection and decrease or eliminate the need for systemic antibiotics. These concentrations can be maintained indefinitely by repeatedly supplying antibiotics through the port 833. The antibiotic solution is injected into the port 833 using a syringe 837 with a non-coring (Huber) needle to enter the skin over the port. "Non-coring" means that the shape of the needle prevents it from taking a cylindrical core of plastic out of the membrane 834 which would cause leakage through the membrane. Instead, the non-coring needle cuts a slit through the membrane 834 which seals when the needle is removed.

In addition to infusion of antibiotics or contrast dye, other medications can be infused through the infusion assembly during surgery or through the port 833 thereafter. For example, one treatment used for prevention of osteoporosis is a class of medications termed "bisphosphonates." These medications have been investigated as a possible treatment for osteolysis in the bone adjacent total hip replacements. One of these, pamidronate, comes in a liquid form for intravenous use. Although the invention provides means of avoiding osteolysis, if osteolysis were to occur, consideration could be given to the infusion of pamidronate. This could provide higher local concentrations of the medication where it is needed. This medication is typically administered every three or four months when used intravenously.

If difficulty is encountered with the minimally invasive method described above, a "mini-open" procedure can be used in which an incision is made which is large enough to directly visualize the tip 720 of the stem 713 protruding from the femur F. Alternatively, the above technique may be combined with an open procedure, e.g., a procedure in which the entire incision is utilized to open the joint and change prostheses.

References (1) Bobyn, J. D. et al.: CORR 261:196, 1990
(2) Davy, D. T. et al.: JBJS 70A:45, 1988
(3) Oh, I. and Harris, W. H.: JBJS 60A:75, 1978
(4) Clark, J. M. et al.: J Arthr 2:99, 1987
(5) Schmalzried, T. P. et al.: JBJS 79A:447, 1997
(6) Harris, W. H. et al.: Instructional Course Lectures AAOS 45:183–185, 1996
(7) Aspenberg, P. A. et al.: CORR 352:75, 1998

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A bone prosthesis for implantation at a joint the prosthesis comprising:
   a stem sized and shaped for implantation in a bone at the joint such that at least a portion of the stem is received in the bone and a portion is exposed to locations outside the bone, the stem having a first passageway arranged within the stem to vent fluid pressure from a first location which is subject to elevated fluid pressures when the joint is in use after implantation of the prosthesis to a second location for venting fluid from the first location to the second location thereby to inhibit fluid pressure build up between bone located at the joint and the prosthesis, the stem further including a tip adapted to be received through the bone upon implantation of the prosthesis the tip being disposed generally at the second location and the first passageway having an aperture generally at the tip,
   a collar on an end of the stem opposite the tip,
   a neck mounted on the collar,
   a ball mounted on the neck, and
   a second passageway in the stem opening on an upper surface of the collar and extending to the second location, wherein the second passageway is sized and shaped to receive an instrument therethrough to provide access to the first location, and wherein the second passageway has no connection to the first passageway.

2. A bone prosthesis as set forth in claim 1 wherein the first passageway is arranged to vent joint wear debris from the first location which is subject to high concentrations of joint wear debris after implantation of the prosthesis to the second location for venting joint wear debris from the first location to the second location thereby to inhibit wear debris build up between bone located at the joint and the prosthesis.

3. A bone prosthesis as set forth in claim 1 wherein the first passageway includes a primary channel extending generally longitudinally of the stem and secondary channels extending from multiple, spaced apart openings on the exterior of the stem to the primary channel.

4. A bone prosthesis as set forth in claim 3 wherein the stem has side surfaces, the secondary channel openings being located in the side surfaces so that the secondary channels and the primary channel are in fluid communication with a prosthesis-bone interface, the secondary channels extending inwardly from the openings at angles oblique to the side surfaces.

5. A bone prosthesis as set forth in claim 4 wherein the primary channel opens at the aperture an the tip of the stem, the aperture and primary channel being sized and shaped to receive an infusion element for infusing fluid into the channel when the bone prosthesis is installed in the bone, the fluid passing from the primary channel to the secondary channels and the prosthesis-bone interface.

6. The bone prosthesis of claim 1 wherein the first and second passageways extend through the stem to separate apertures at the stem tip.

7. A bone prosthesis for implantation at a joint the prosthesis comprising a stem, the stem having a tip generally at one end thereof, the stem being sized and shaped for reception in a bone at the joint such that the tip of the stem is exposed to locations outside of the bone, the stem having a passageway therein extending from a first location on the bone prosthesis to a second location on the bone prosthesis, the passageway having an aperture at the second Location, an infusion element for infusing fluid into the passageway when the bone prosthesis is installed in the bone, the aperture and passageway being sized and shaped to receive the infusion element, the passageway including a primary channel extending from the aperture at the second location and secondary channels extending from the primary channel to openings in the bone prosthesis, the infused fluid being capable of passing from the primary channel to the secondary channels and thence out of the Secondary channel openings, the infusion element having threads formed thereon, and wherein the primary channel has threads at the aperture adapted to engage the threads of the infusion element for securing the infusion element in the aperture, and wherein the tip of the stem is generally at the second location and the primary channel aperture is located generally at the tip.

8. A bone prosthesis for implantation at a joint, the prosthesis comprising a stem the stem having a tip generally at one end thereof, the stem being sized and shaped for reception in a bone at the joint such that the tip of the stem is exposed to locations outside of the bone, the stem having a Passageway therein extending from a first location the bone prosthesis to a second location on the bone prosthesis, the passageway having an aperture at the second location, an infusion element for infusing fluid into the passageway when the bone prosthesis is installed in the bone, the aperture and passageway being sized and shaped to receive the infusion element, and an infusion port in fluid communication with the infusion element, the infusion port being adapted for implantation under the skin for use in repeated infusion of fluid into the passageway.

9. A bone prosthesis as set forth in claim 8 wherein the passageway comprises a primary channel extending from the aperture at the second location and secondary channels extending from the primary channel to openings in the bone prosthesis, the infused fluid being capable of passing from the primary channel to the secondary channels and thence out of the secondary channel openings.

10. A bone prosthesis as set forth in claim 9 wherein the infusion element has threads formed thereon, and wherein the primary channel has threads at the aperture adapted to engage the threads of the infusion element for securing the infusion element in the aperture.

11. A method of minimally invasive accessing of a femoral head-neck prosthesis transosseously implanted in a femur in a thigh of a patient, the prosthesis comprising a stem having a passageway extending at least partway through the stem along a longitudinal axis and opening at an aperture at a tip of the stem, the passageway being in fluid communication with a prosthesis-bone interface, the stem being implanted such that the aperture of the passageway in the stem is accessible from a location external to the femur, the method comprising the steps of:

examining the prosthesis using an X-ray device while Simultaneously rotating the femur until a viewing plane of the X-ray device is generally parallel with the longitudinal axis of the passageway;

determining an intersection point of the longitudinal axis of the stem with skin of the thigh;

making an incision at the intersection point; and inserting an instrument through the skin generally along the longitudinal axis and into the aperture of the passageway.

12. A method as set forth in claim 11 further comprising the step of withdrawing a fluid sample with the instrument inserted into the passageway of the bone prosthesis.

13. A method as set forth in claim 11 further comprising cleaning the passageway with the instrument inserted therein.

14. A method as set forth in claim 11 further comprising the step of infusing a fluid into the passageway through the instrument.

15. A method as set forth in claim 14 wherein the fluid is a medicine.

16. A method as set forth in claim 14 wherein the fluid is a dye and wherein the method further comprises the step of imaging the dispersion of fluid with the X-ray device.

17. A method as set forth in claim 14 further Comprising the steps of implanting an infusion port under the skin in fluid communication with the instrument inserted in the passageway, and repeatedly infusing fluid into the passageway by injection through the skin and into the infusion port.

* * * * *

UNITED STATES PATENT AND TRADEMARK OFFICE
CERTIFICATE OF CORRECTION

PATENT NO. : 6,740,120 B1
DATED : May 25, 2004
INVENTOR(S) : James B. Grimes

It is certified that error appears in the above-identified patent and that said Letters Patent is hereby corrected as shown below:

Column 28,
Line 66, "an the tip" should read -- in the tip --.

Column 29,
Line 15, "Location" should read -- location --.
Line 25, "Secondary" should read -- secondary --.
Line 38, "Passageway therein extending from a first locating the" should read
-- passageway therein extending from a first location on the --.

Column 30,
Line 22, "Simultaneously" should read -- simultaneously --.
Line 46, "Comprising" should read -- comprising --.

Signed and Sealed this

Tenth Day of August, 2004

JON W. DUDAS
*Acting Director of the United States Patent and Trademark Office*